United States Patent [19]
Carter et al.

[11] Patent Number: 5,169,956
[45] Date of Patent: Dec. 8, 1992

[54] MACROLIDE ANTIBIOTIC COMPOUNDS

[75] Inventors: Guy T. Carter; Margaret J. Torrey; Michael Greenstein, all of Suffern, N.Y.

[73] Assignee: American Cyanamid Company, Stamford, Conn.

[21] Appl. No.: 543,290

[22] Filed: Jun. 25, 1990

Related U.S. Application Data

[63] Continuation of Ser. No. 732,252, May 10, 1985, Pat. No. 5,106,994, which is a continuation-in-part of Ser. No. 617,650, Jun. 5, 1984, abandoned.

[51] Int. Cl.$^5$ .................. C07D 493/22; A61K 35/00; C12B 17/18; C12N 1/20
[52] U.S. Cl. ................................. 549/264; 424/120; 424/121; 424/122; 435/119; 435/252.1; 435/253.5
[58] Field of Search ............... 549/264, 265; 424/120, 424/121, 122; 435/119, 252.1, 253.5

[56] References Cited

PUBLICATIONS

Carter, G. T., *J. Org. Chem*, 1986, vol. 51, pp. 4264–4271.
Lardy, et al., *Arch. Biochem. Biophys.* vol. 78, 1958, pp. 487–497.

*Primary Examiner*—Irene Marx
*Attorney, Agent, or Firm*—Estelle J. Tsevdos

[57] ABSTRACT

This invention relates to new agents designated LL-F28249α, LL-F28249β, LL-F28249γ, LL-F28249δ, LL-F28249ε, LL-F28249ζ, LL-F28249η, LL-F28249θ, LL-F28249ι, LL-F28249κ, LL-F28249λ, LL-F28249μ, LL-F28249ν, and LL-F2924ω, to their production by fermentation, to methods for their recovery and concentration from crude solutions, to processes for their purification and to pharmaceutically and pharmacologically-acceptable salts thereof. The present invention includes within its scope the biologically pure culture which produces there agents, derived from a newly-discovered and previously uncultured microorganism, *Streptomyces cyaneogriseus* subsp. *noncyanogenus*, NRRL 15773.

5 Claims, 56 Drawing Sheets

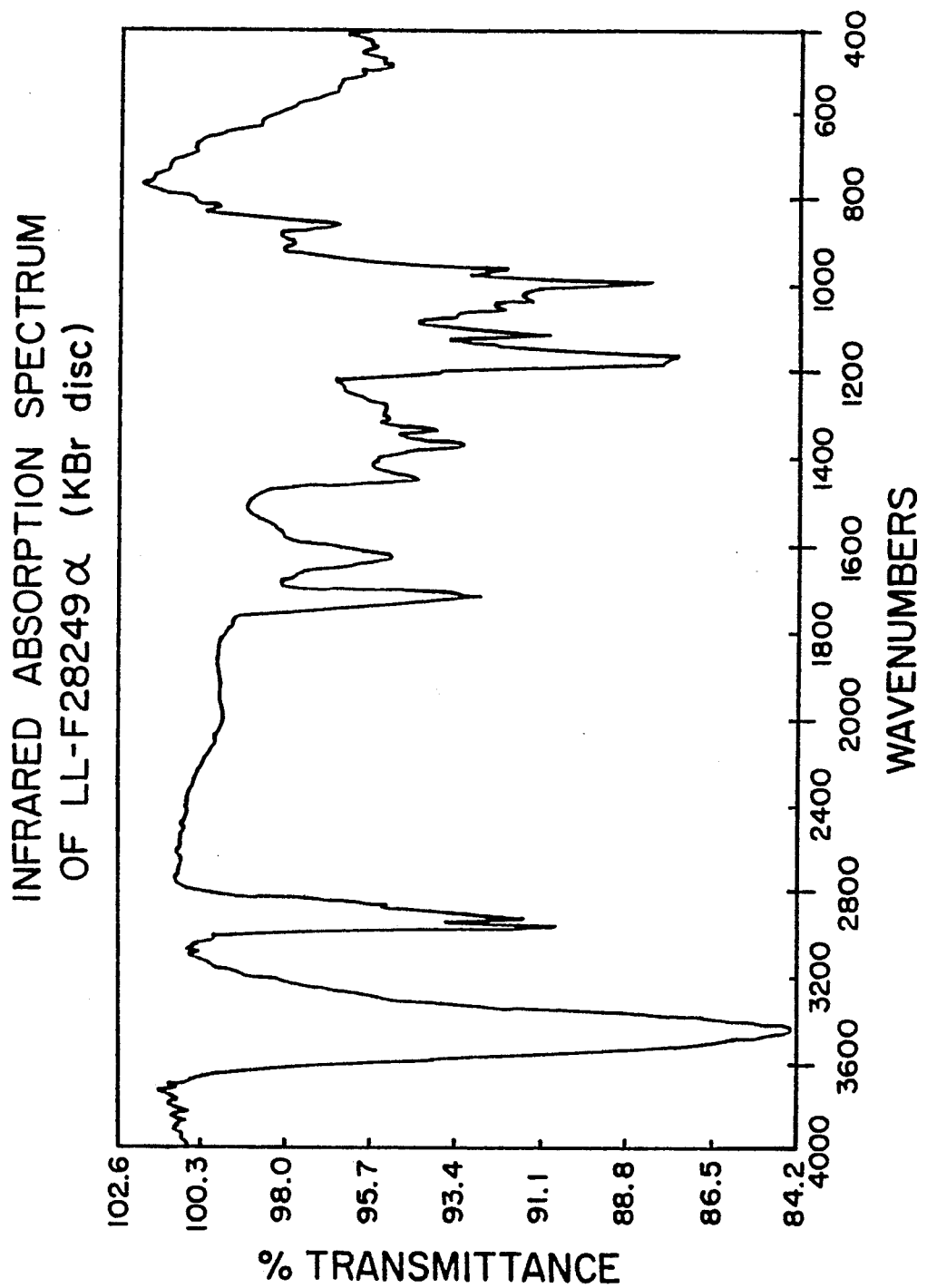
FIG. II

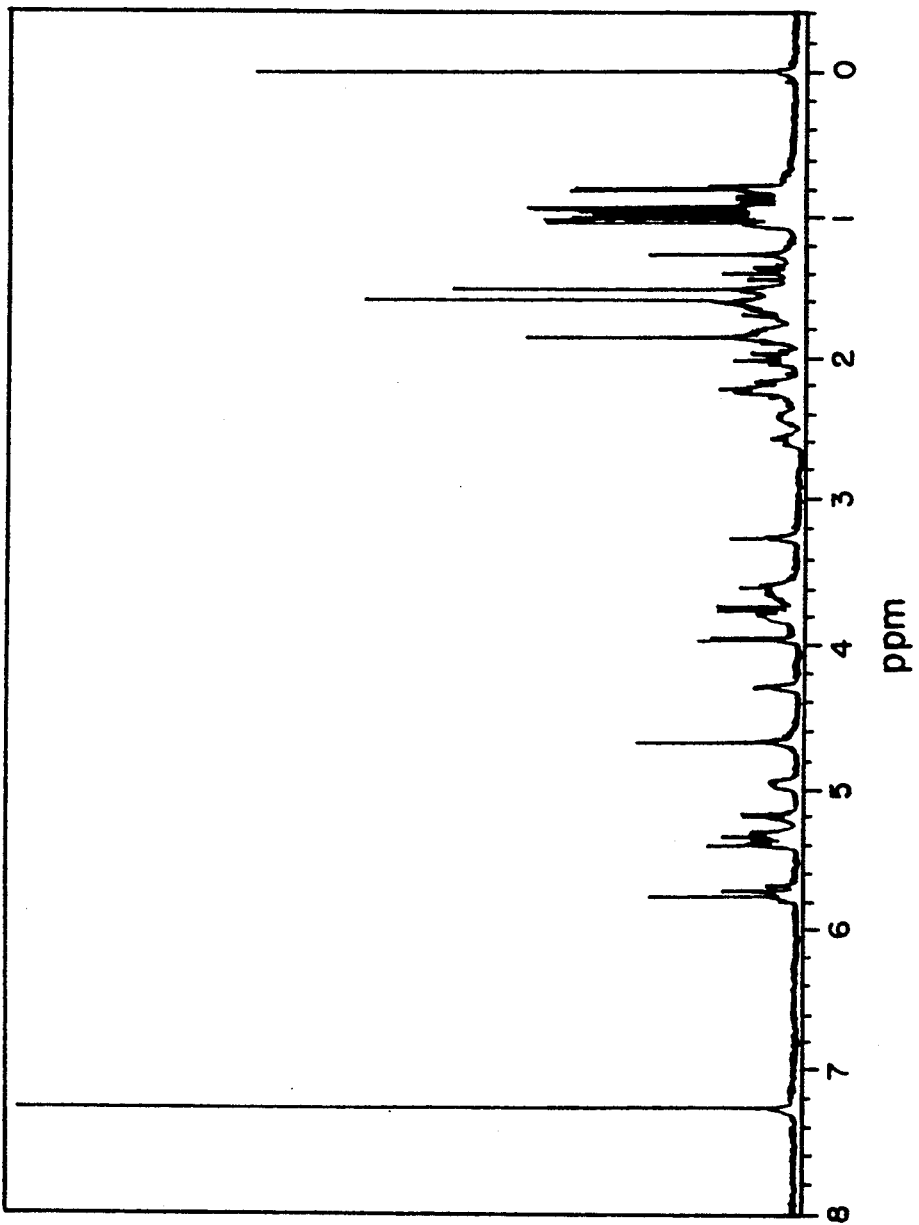
FIG. III

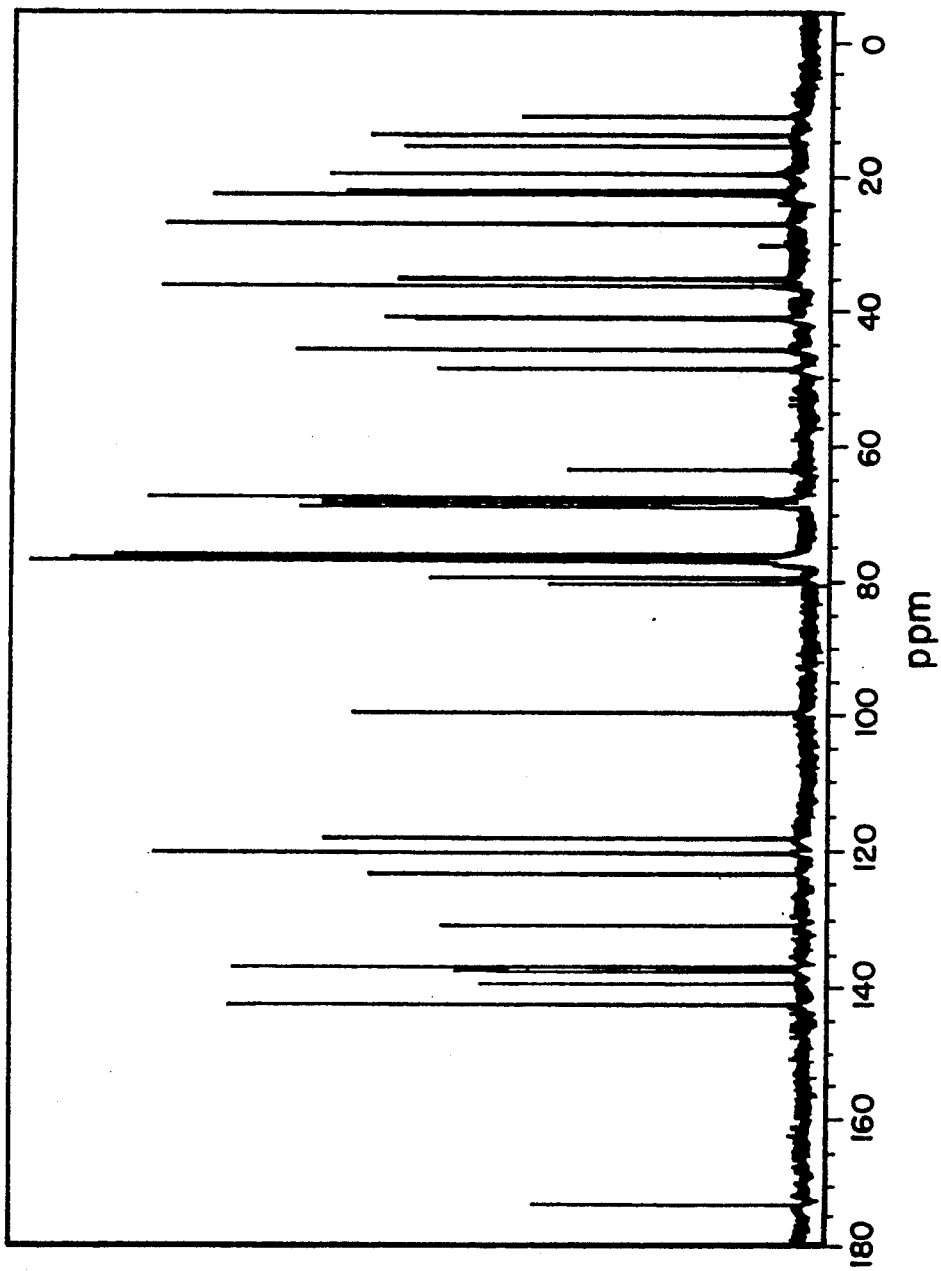
FIG. IV

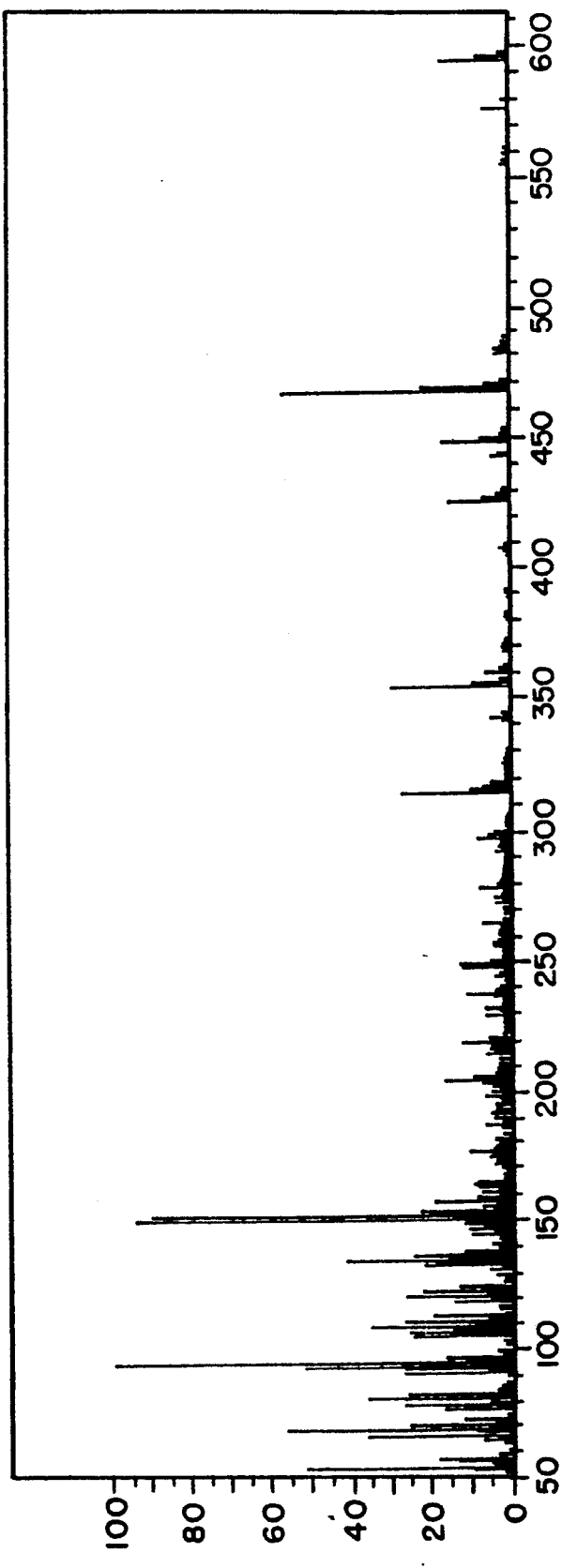
FIG. V

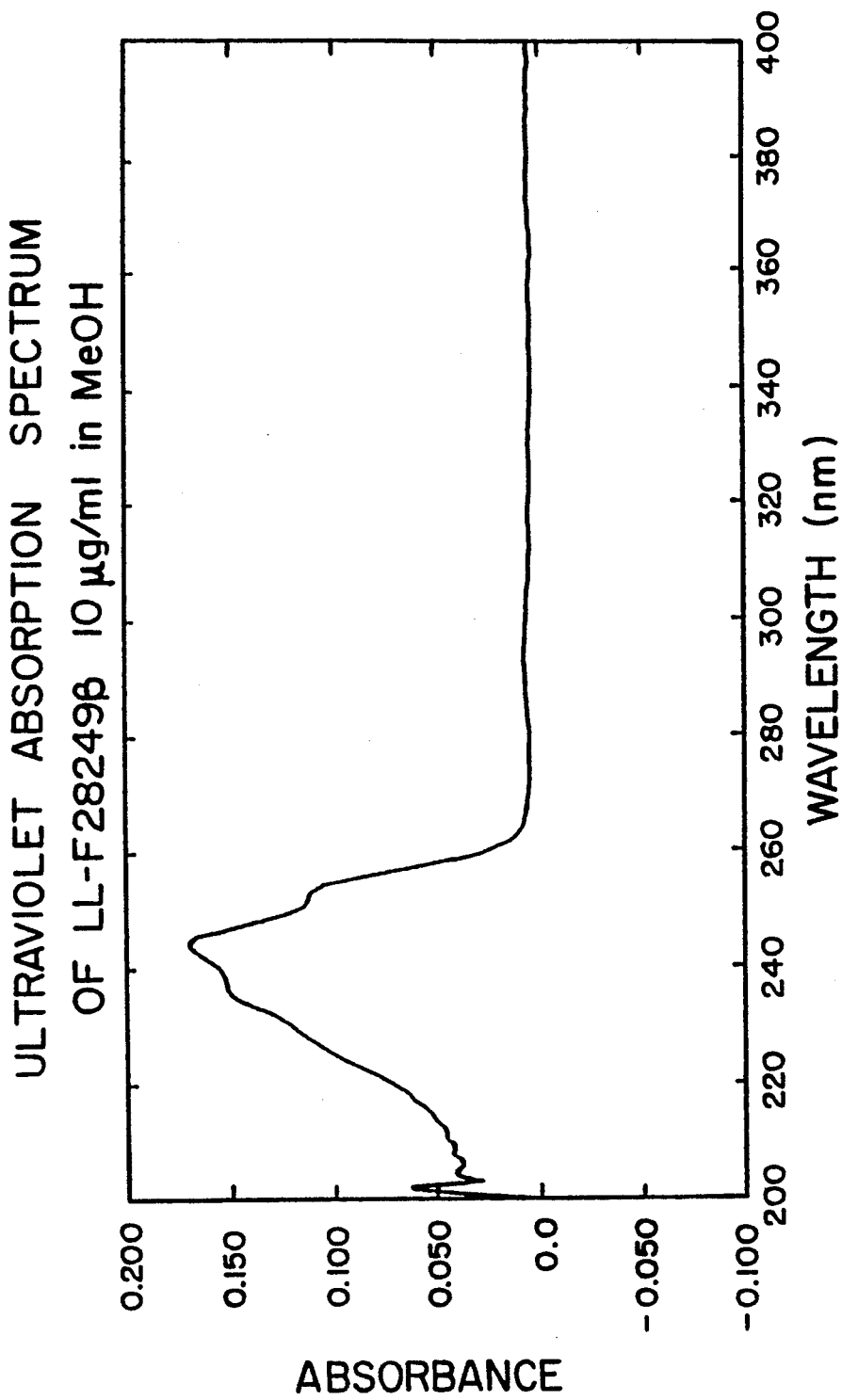
FIG. VI

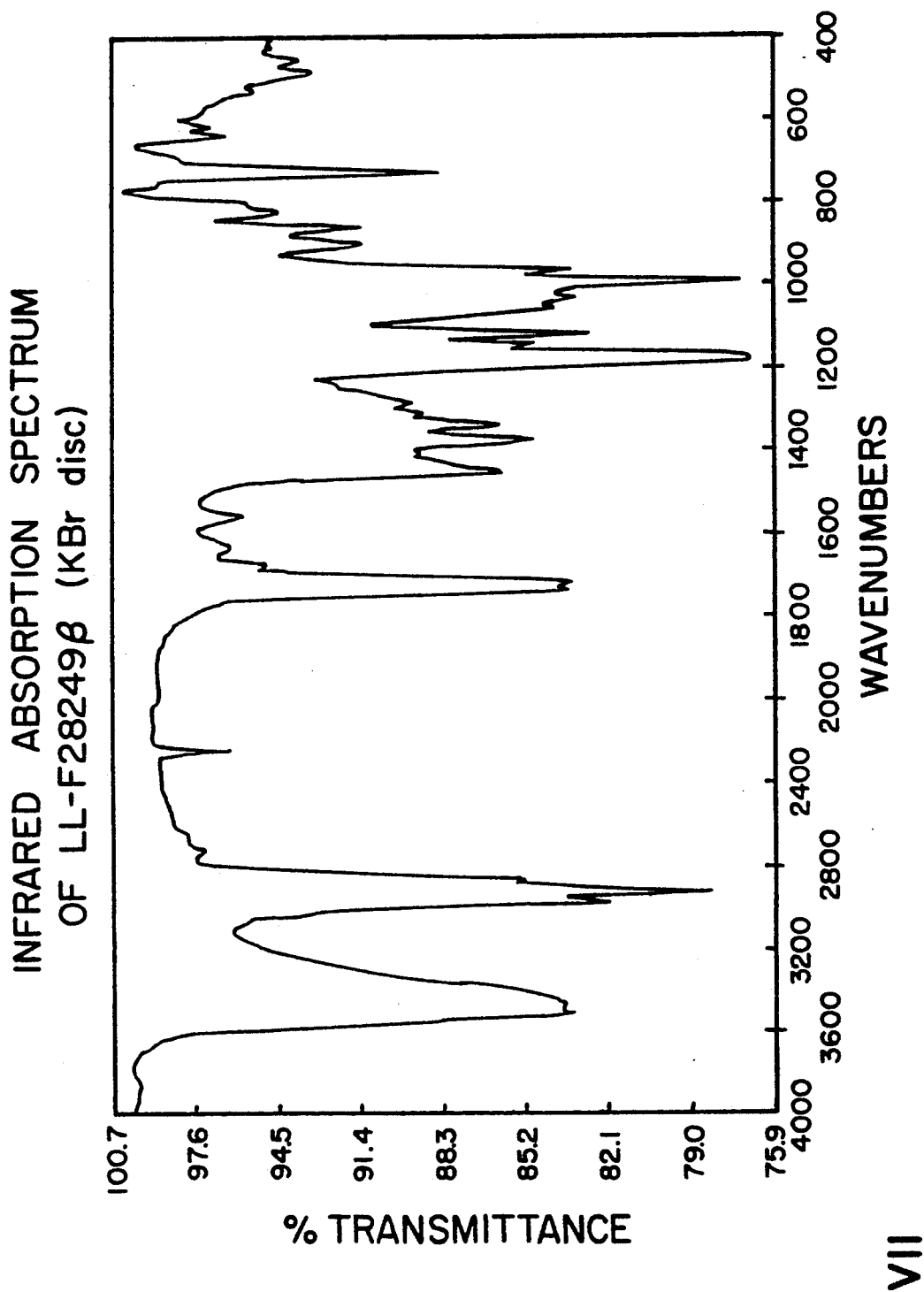
FIG. VII

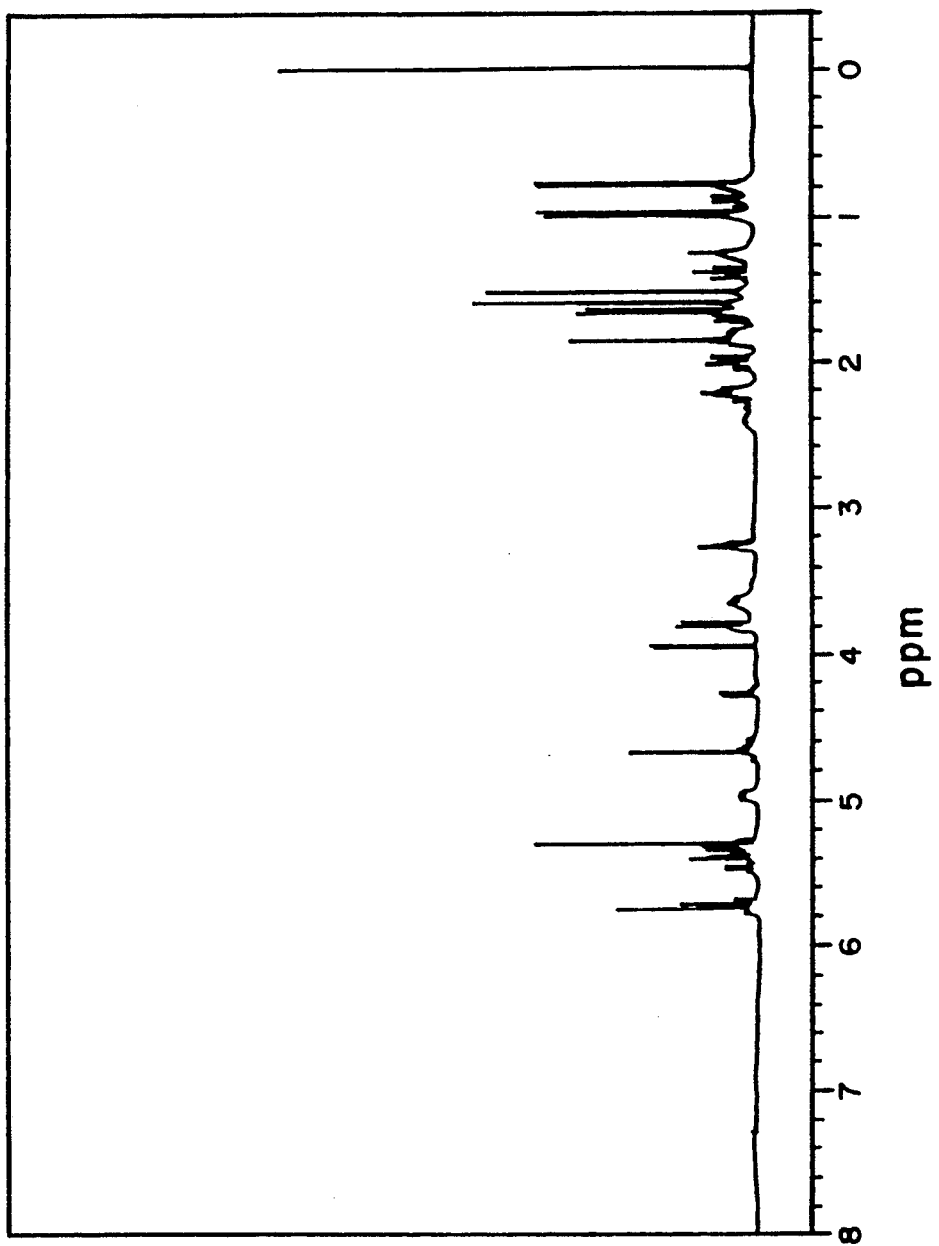

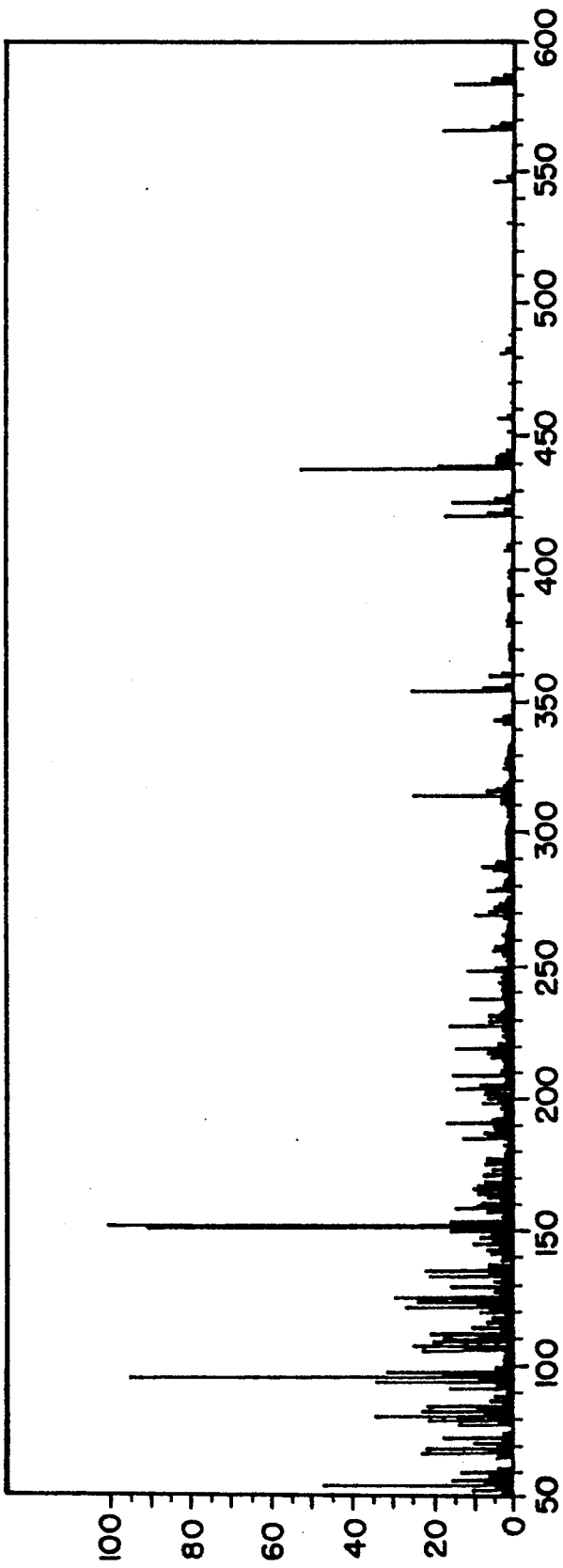
FIG. IX

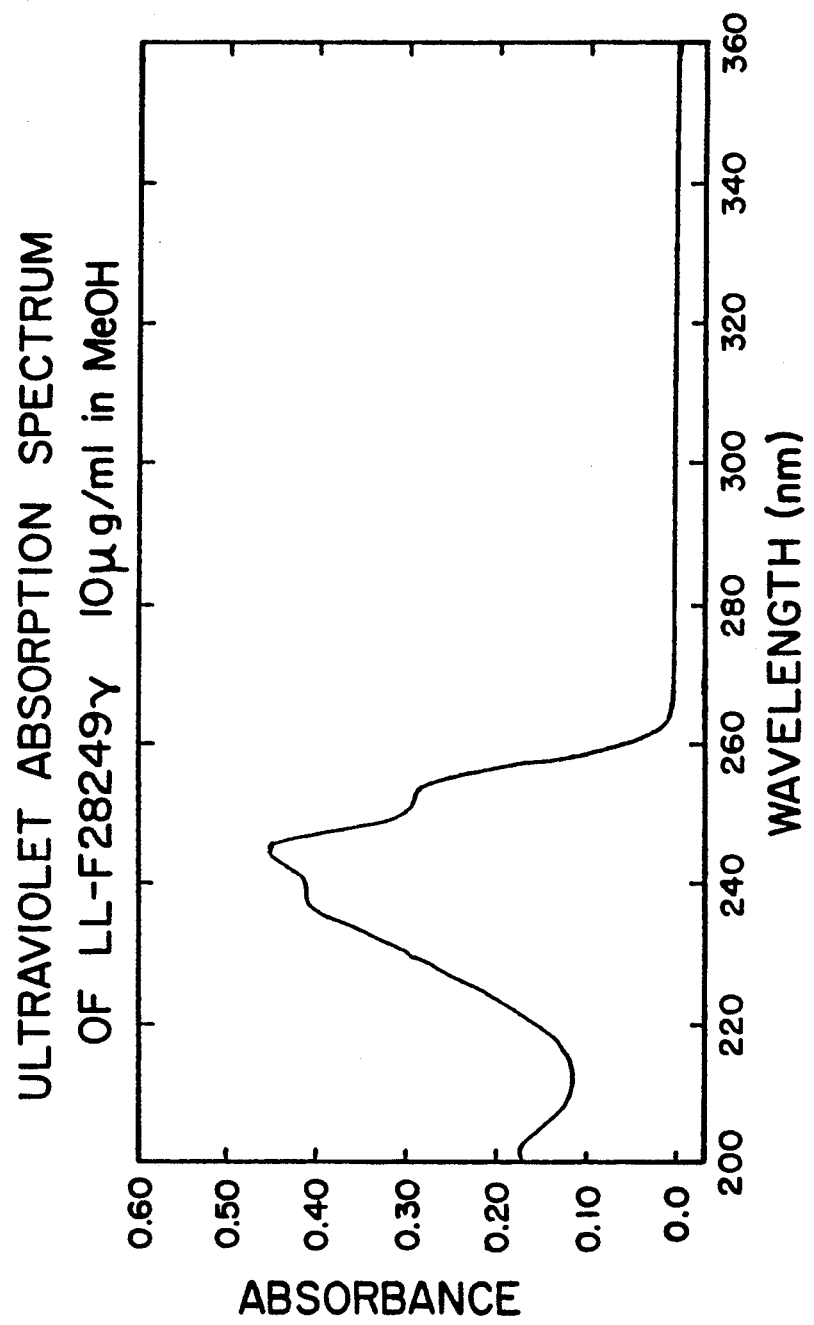
FIG. X

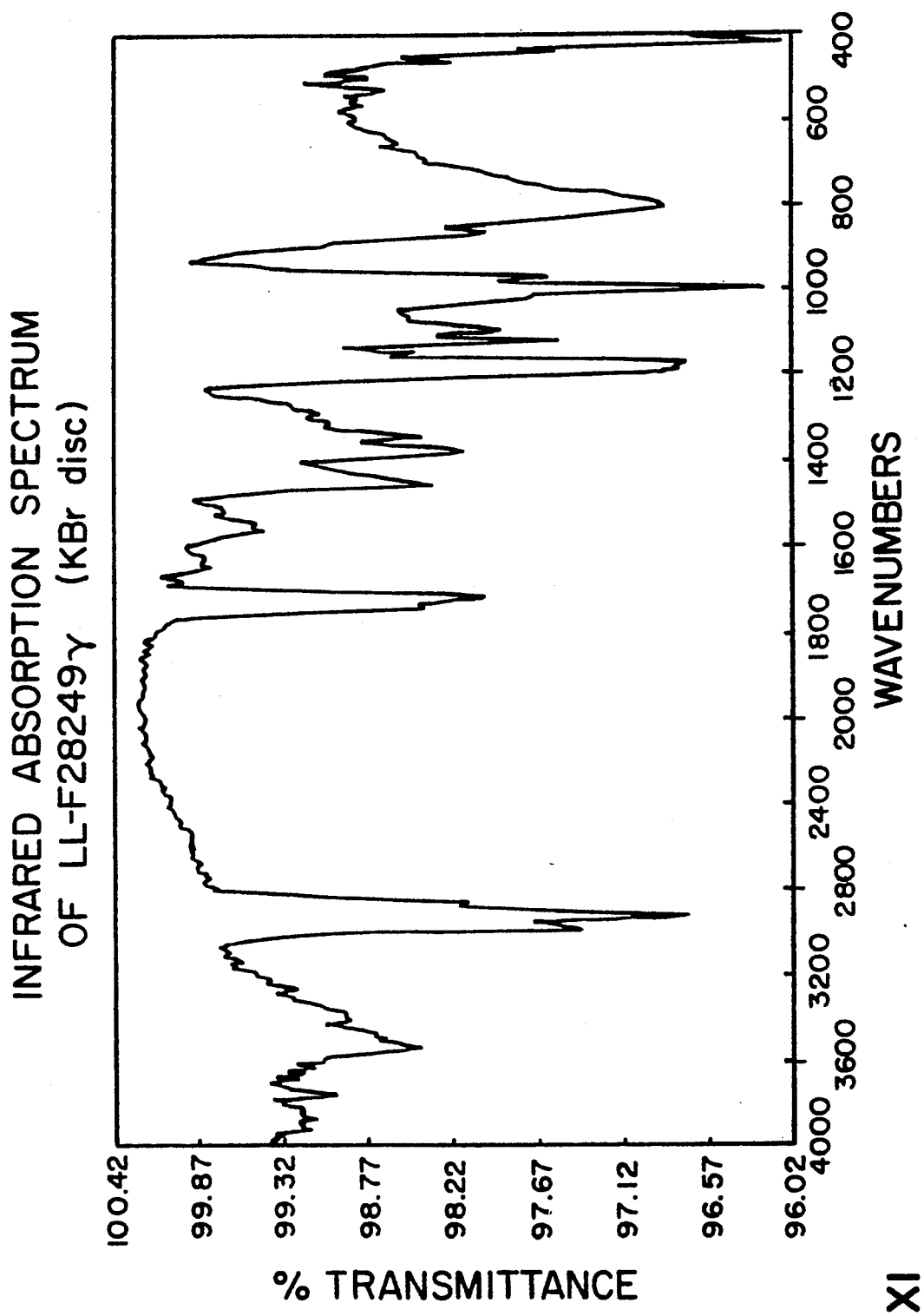
FIG. XI

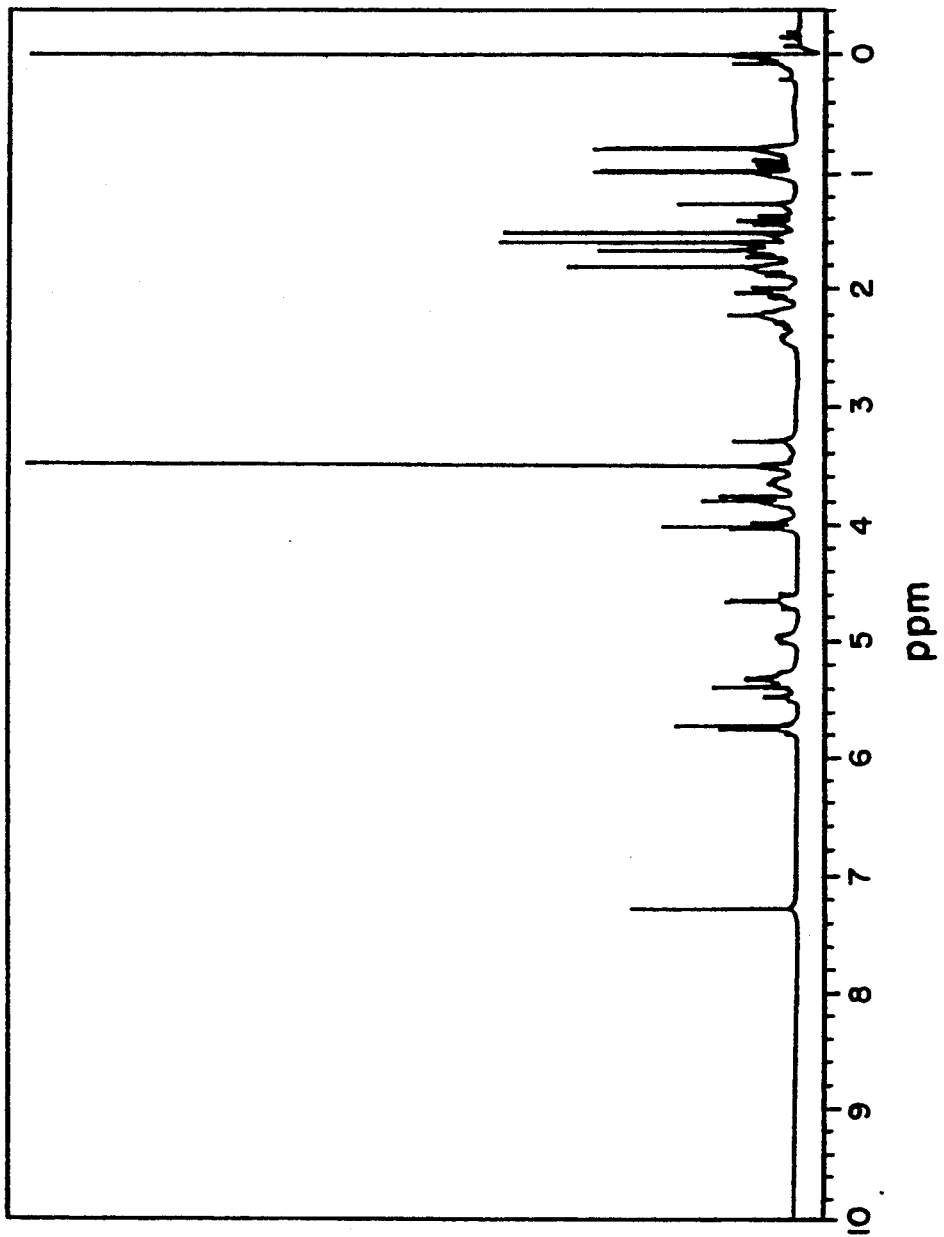
FIG. XII

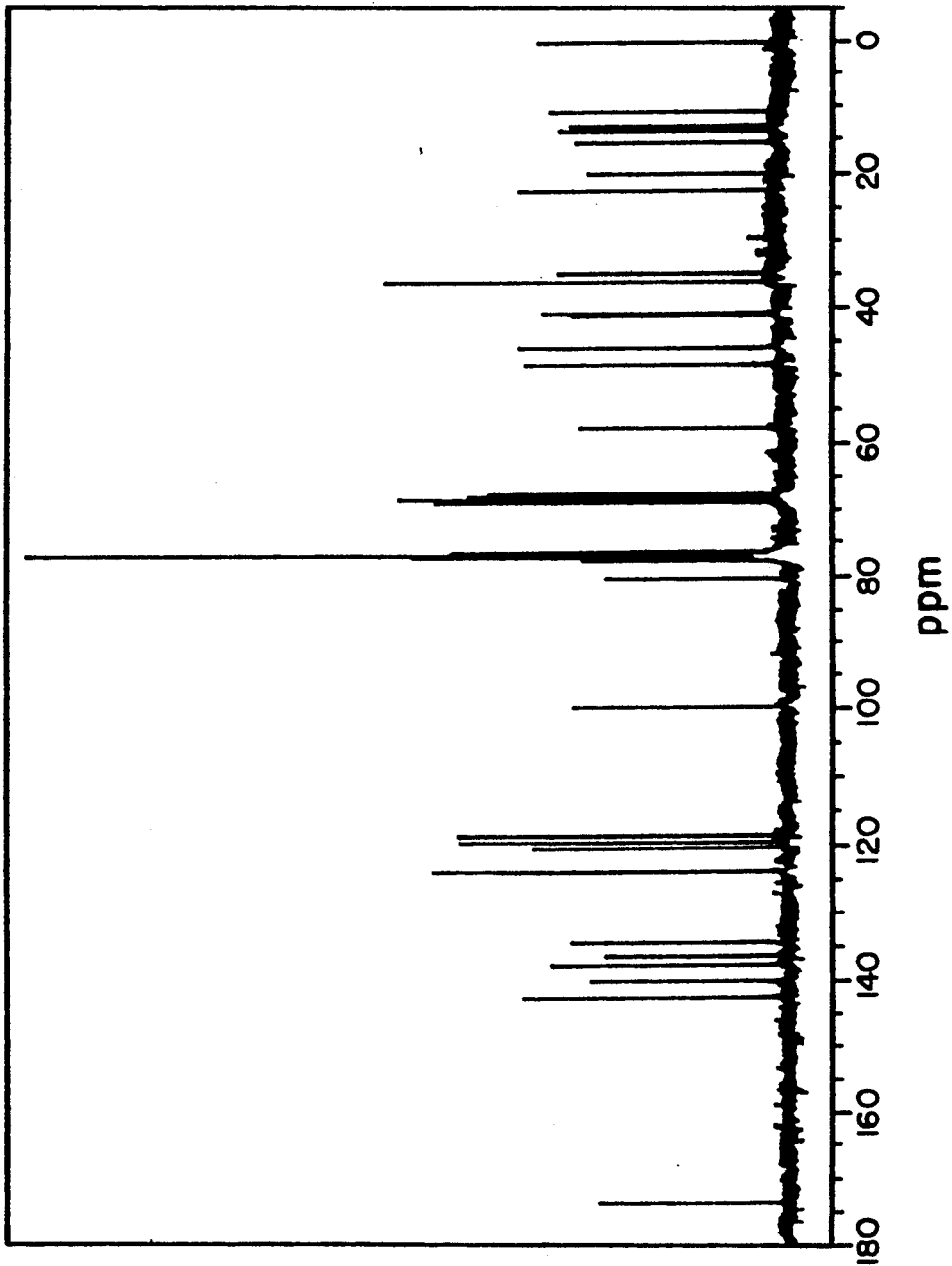
FIG. XIII

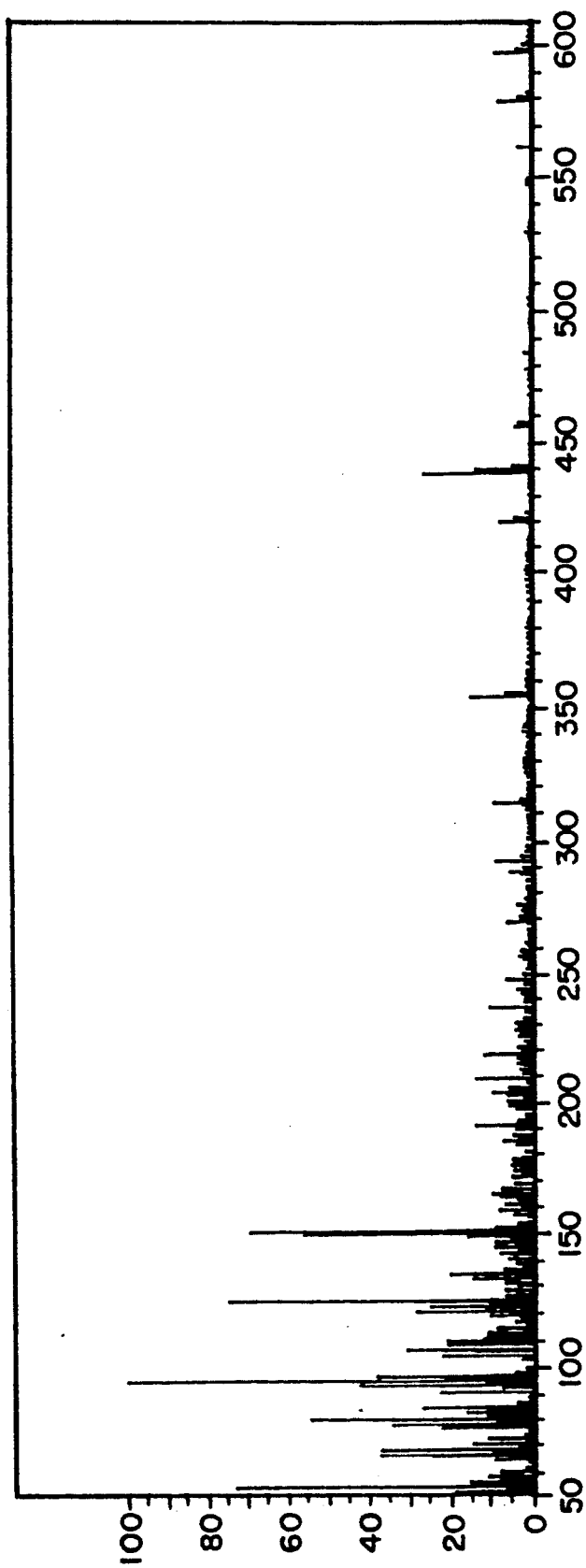
FIG. XIV

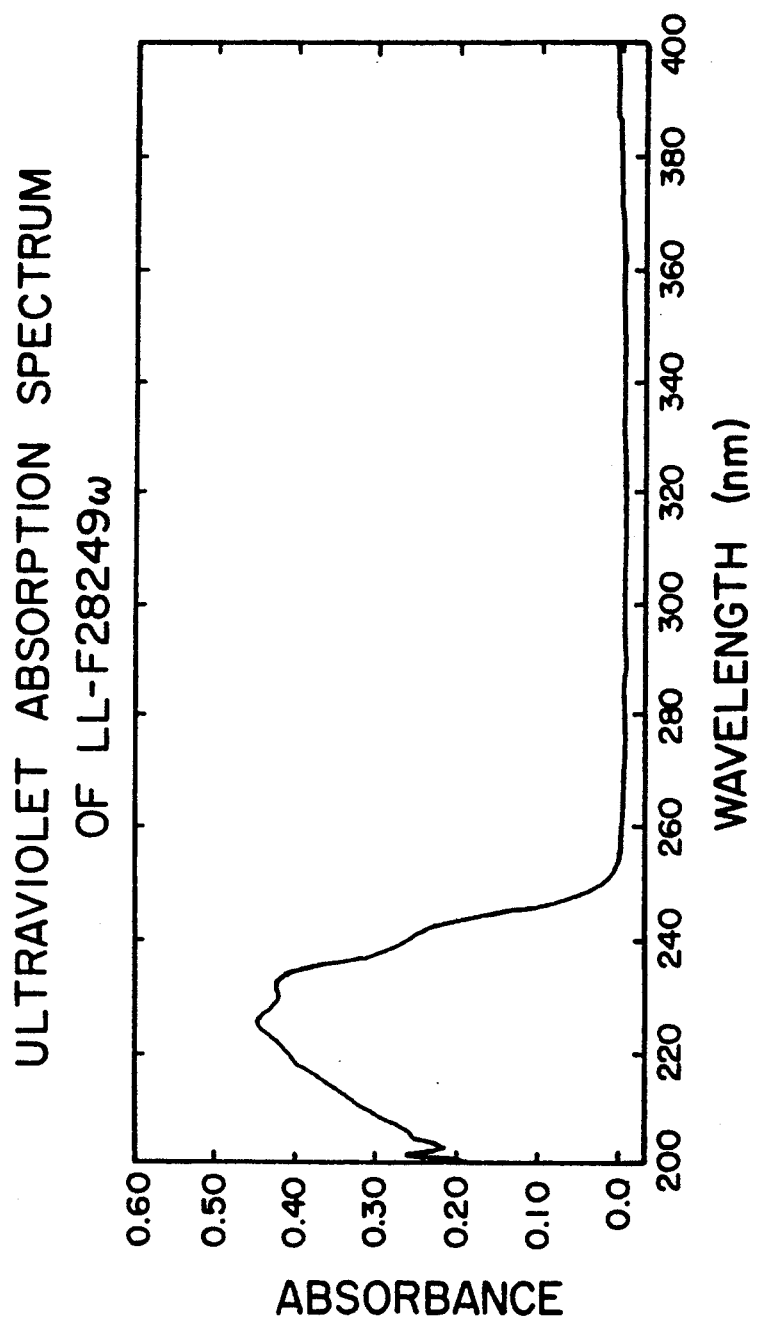
FIG. XV

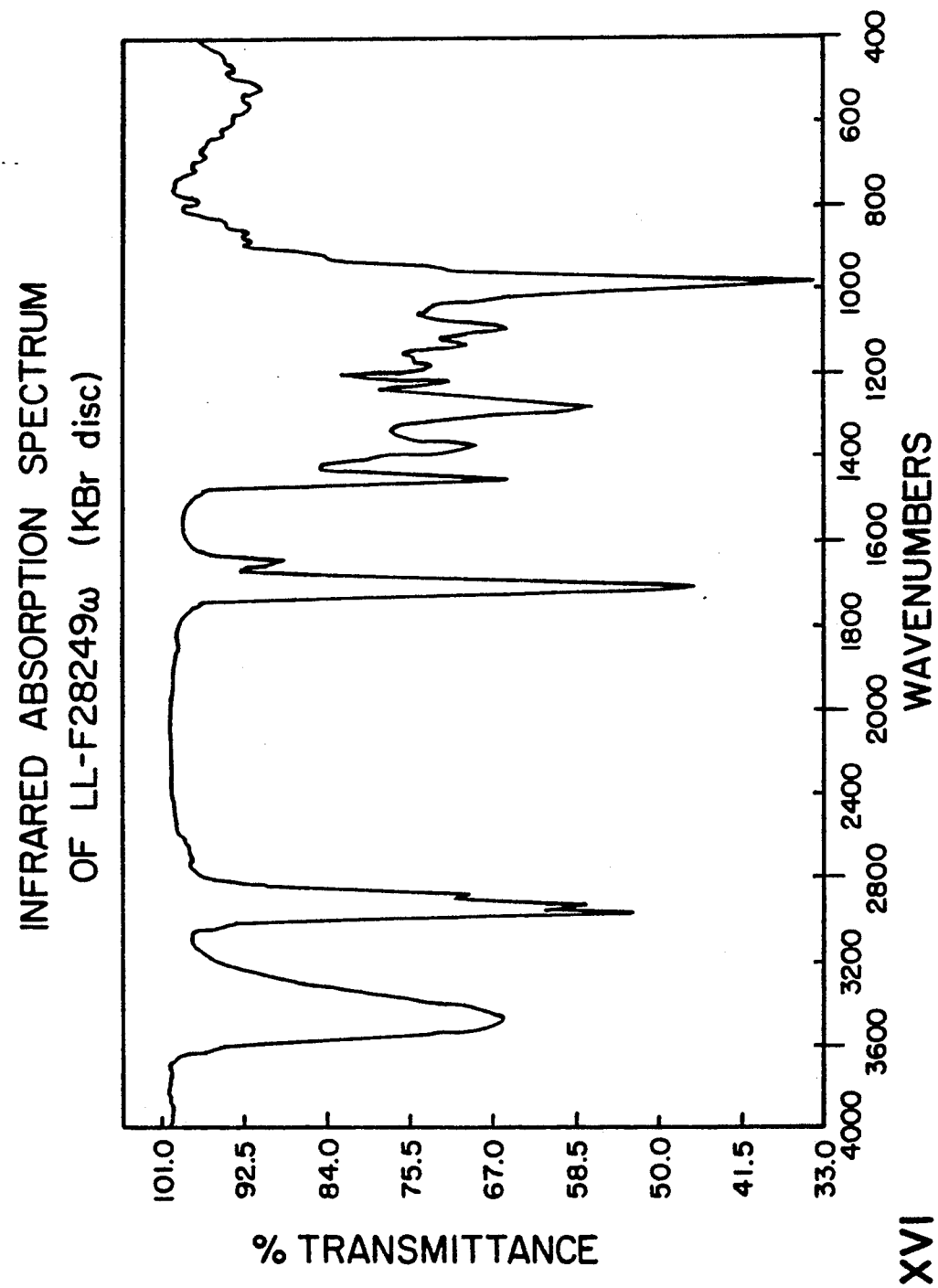
FIG. XVI

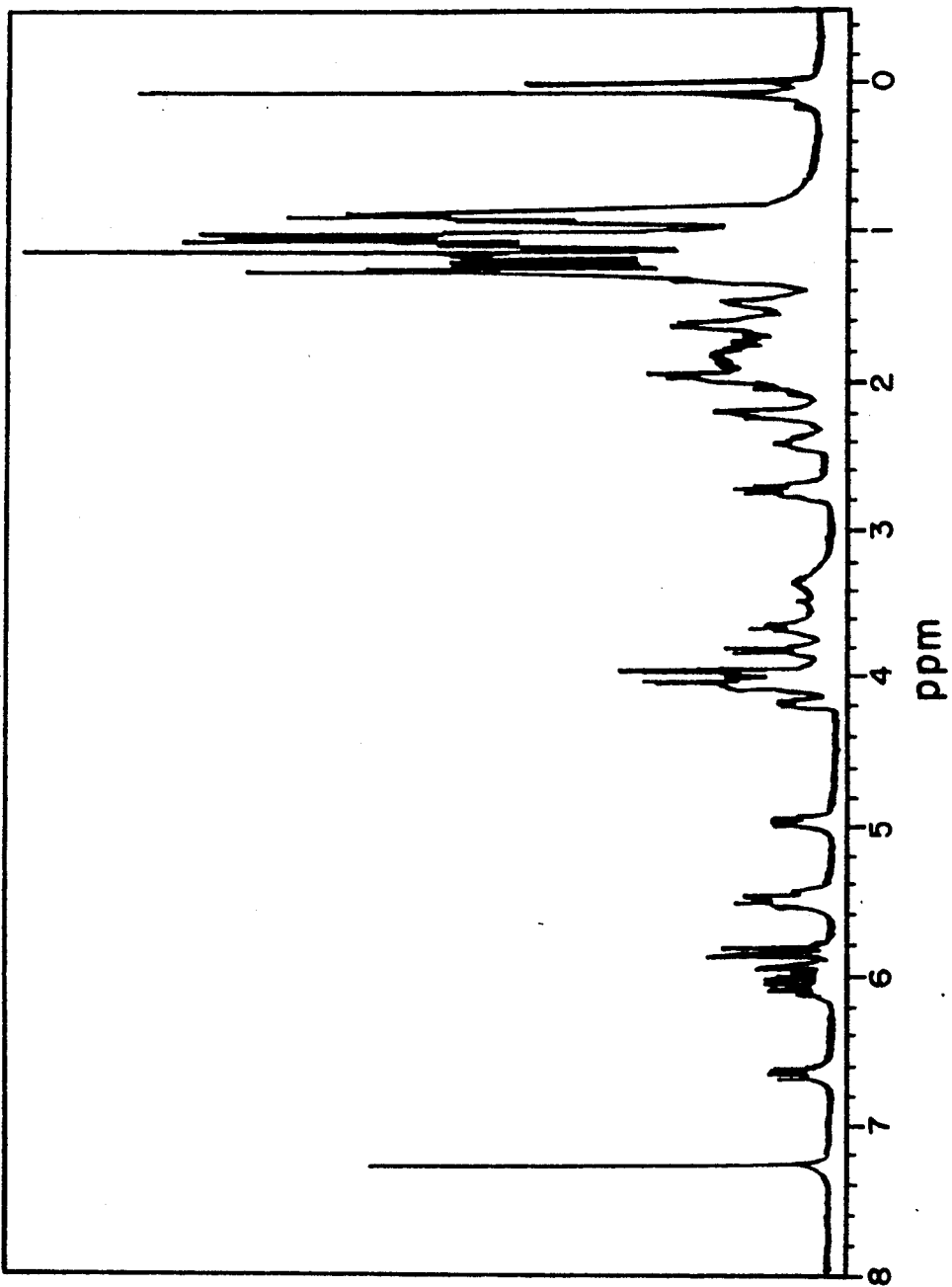
FIG. XVII

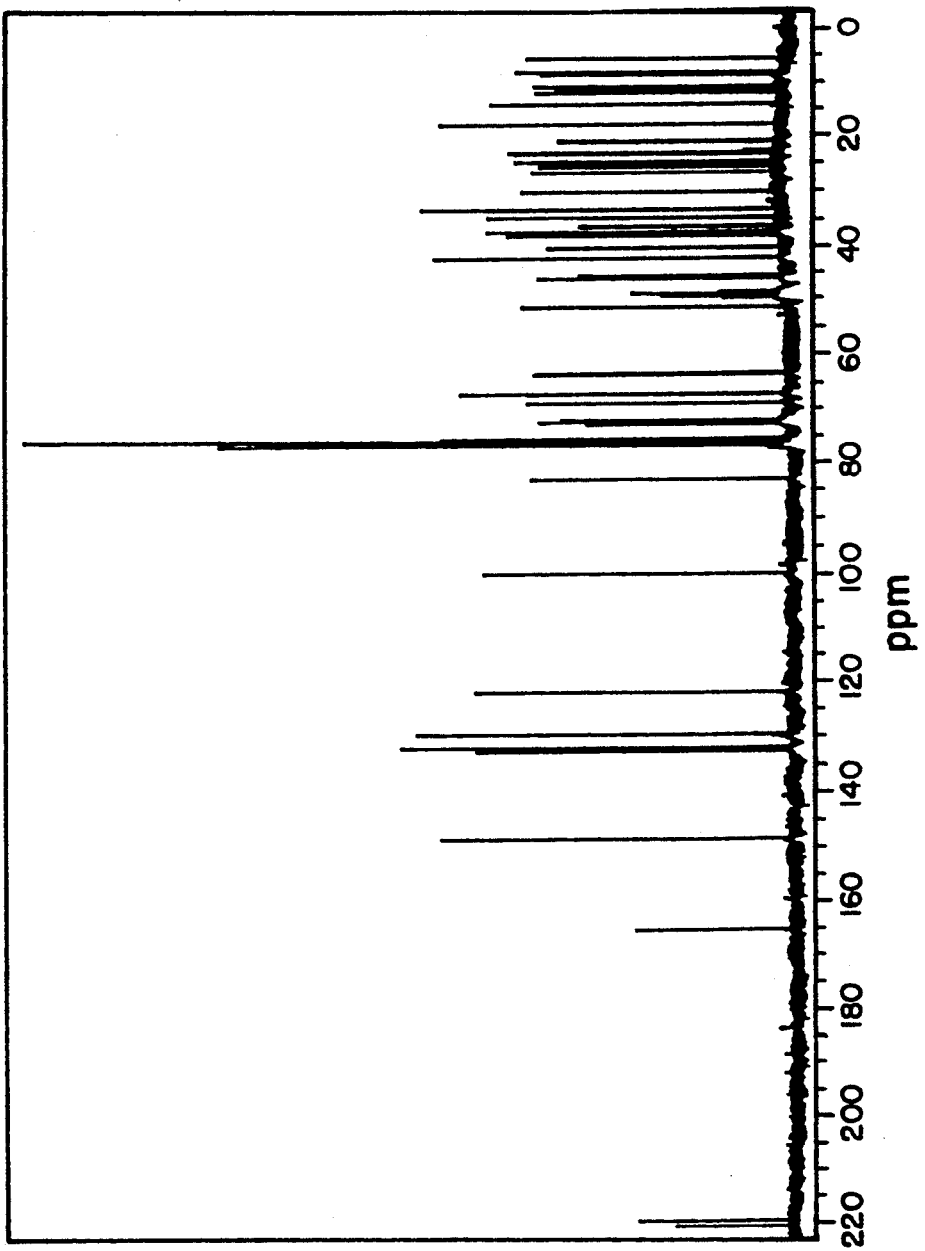
FIG. XVIII

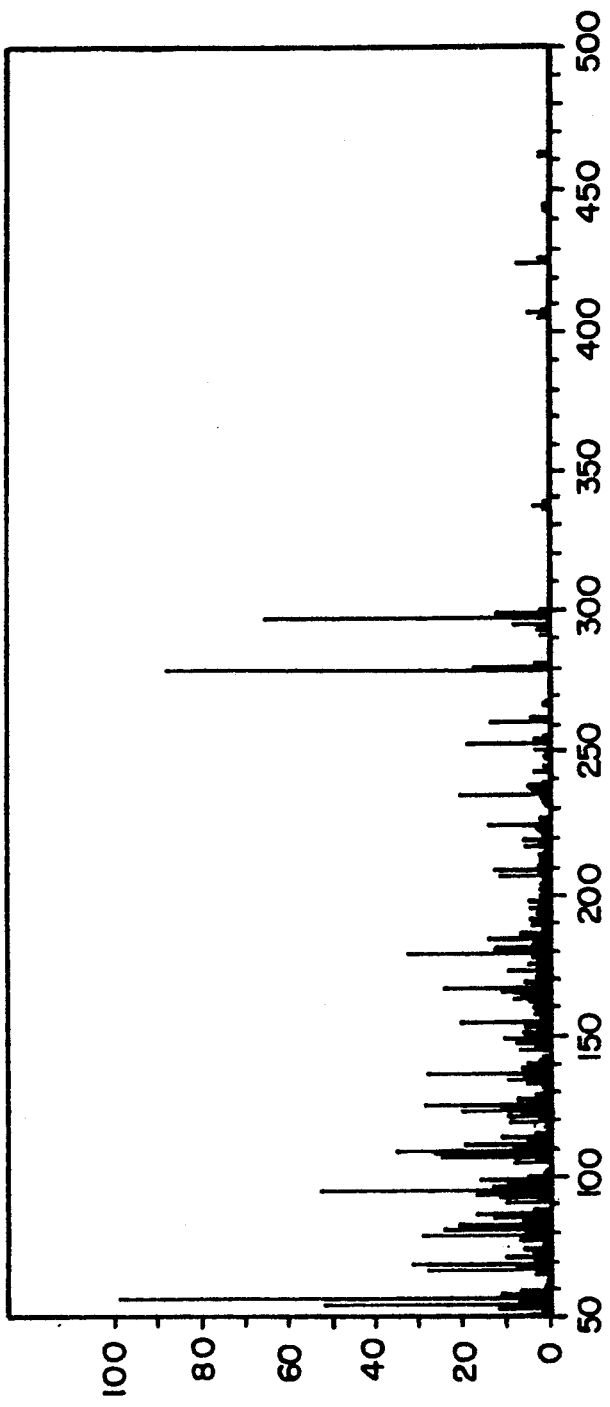
FIG. XIX

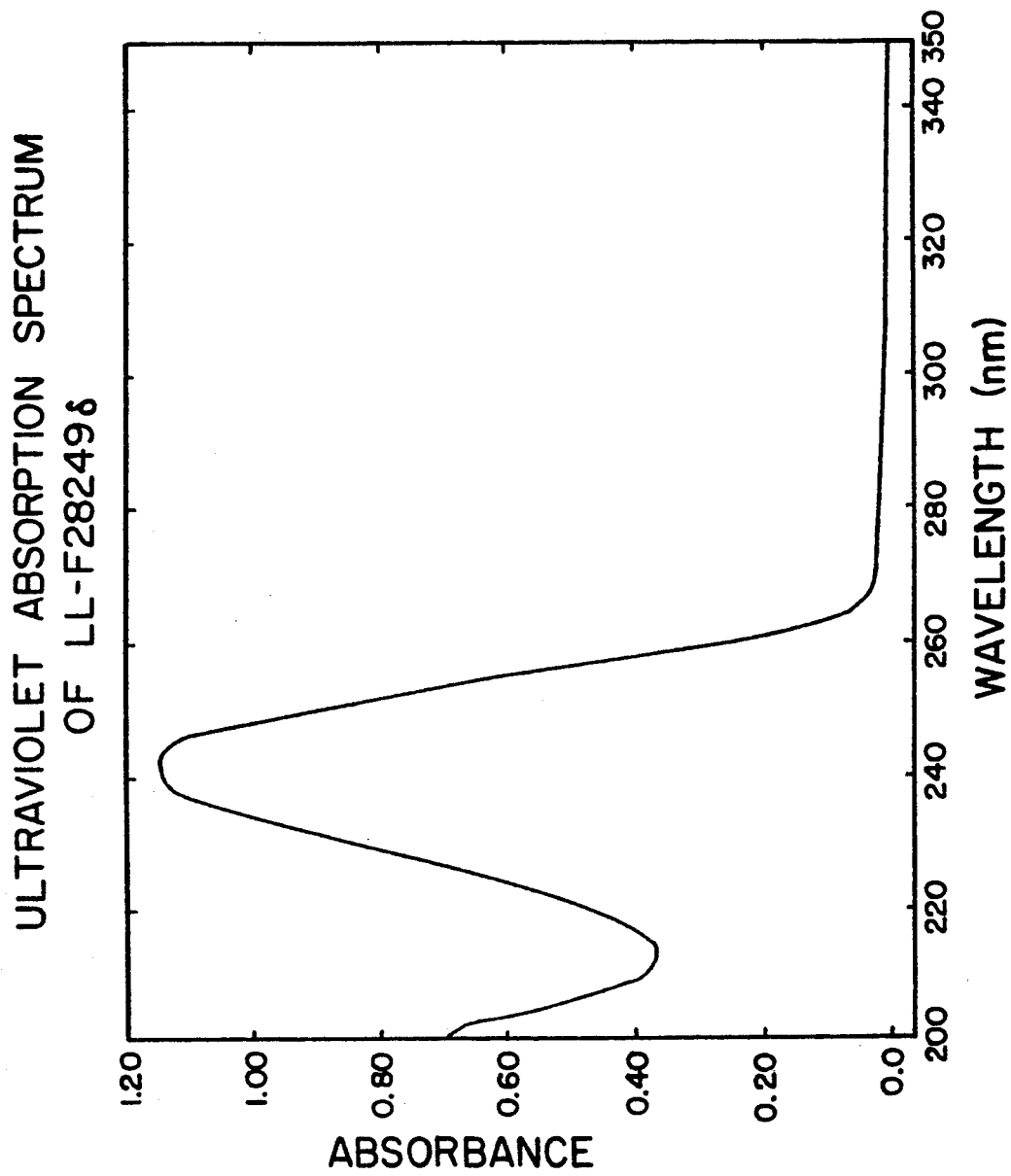
FIG. XX

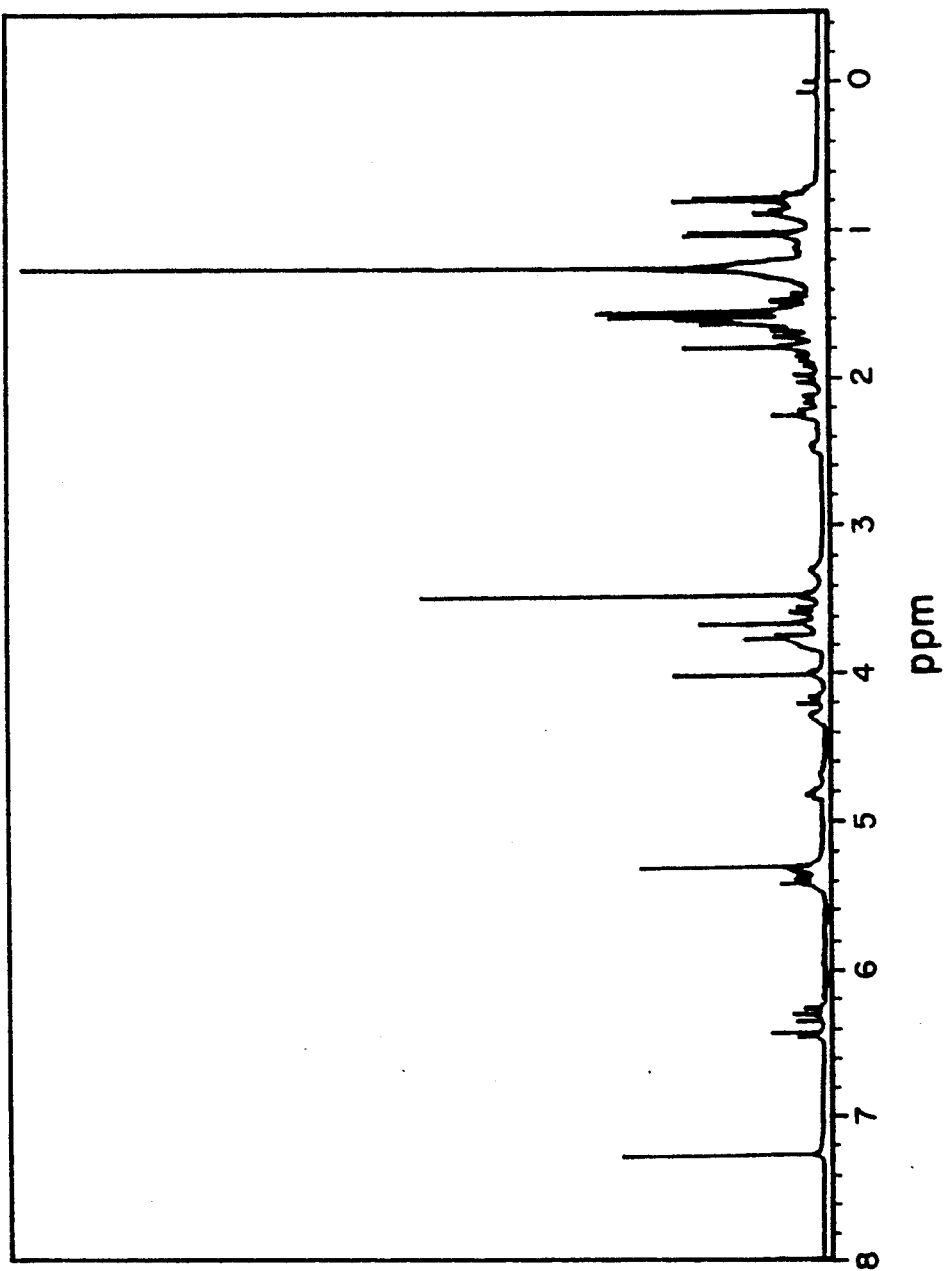
FIG. XXI

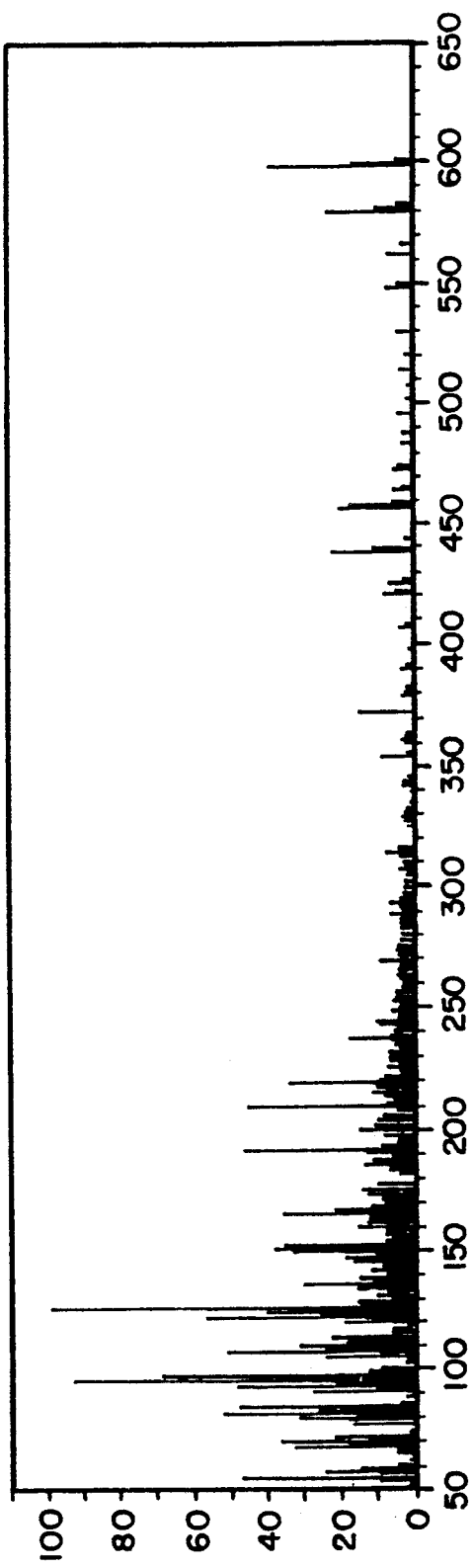
FIG. XXII

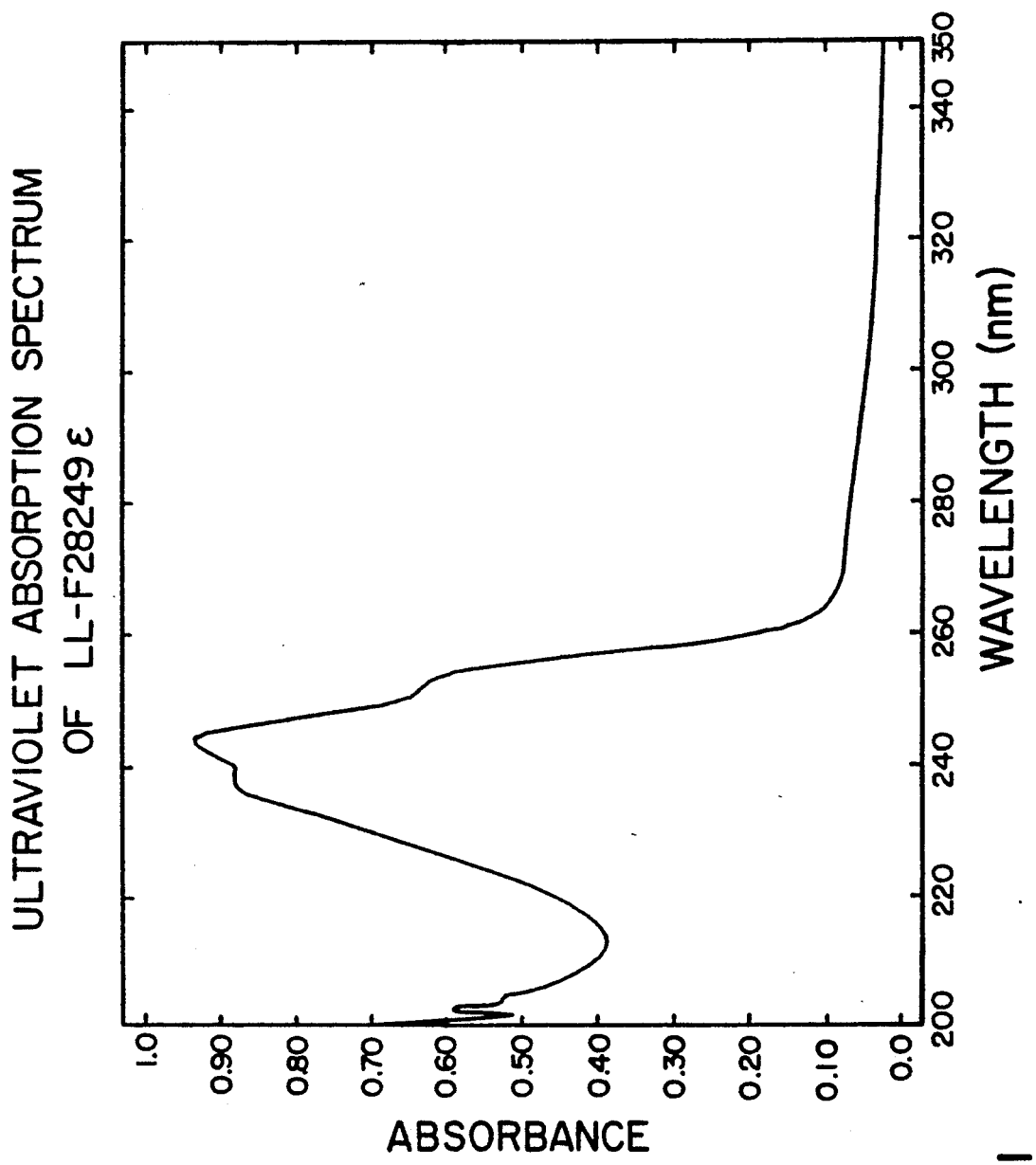
FIG. XXIII

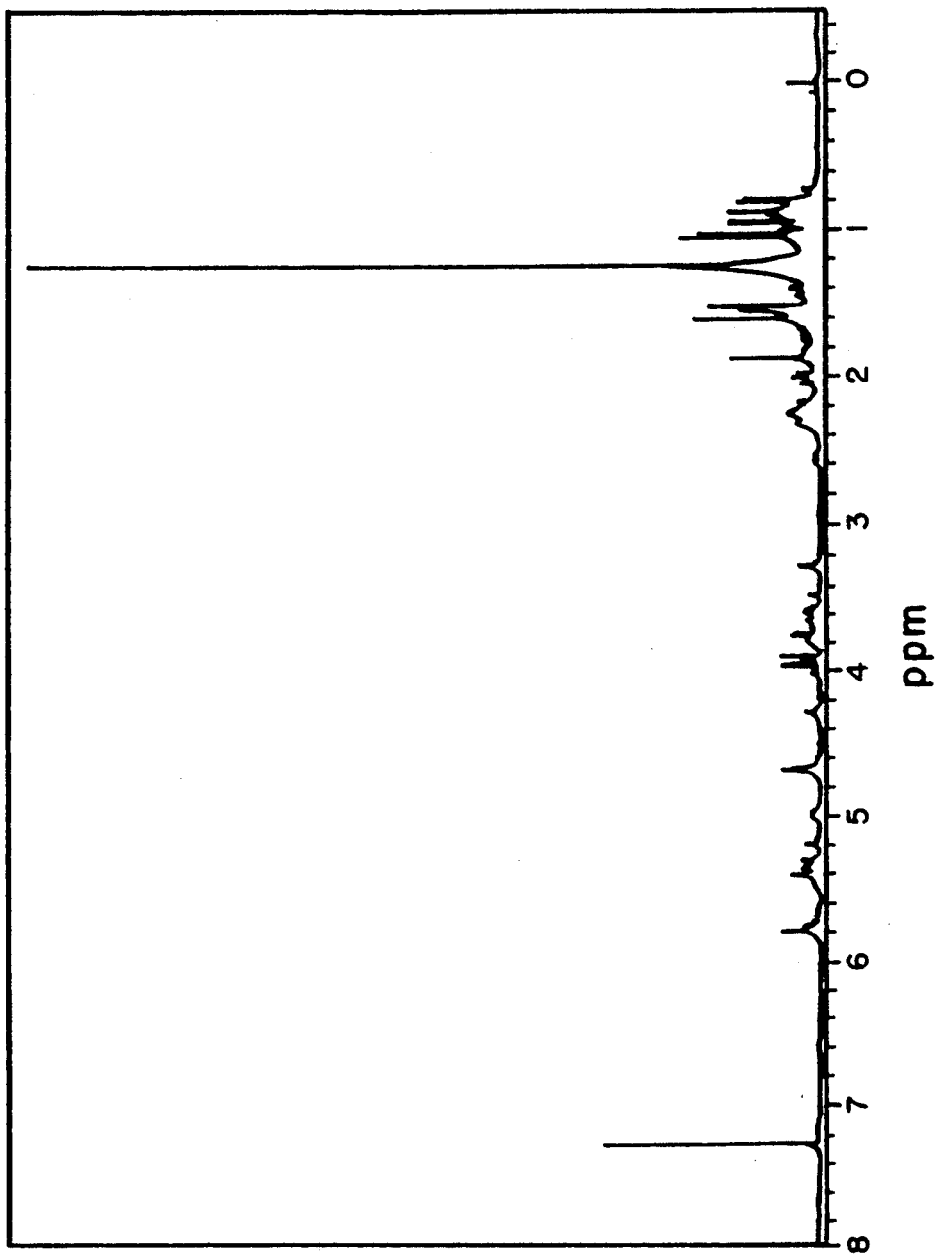
FIG. XXIV

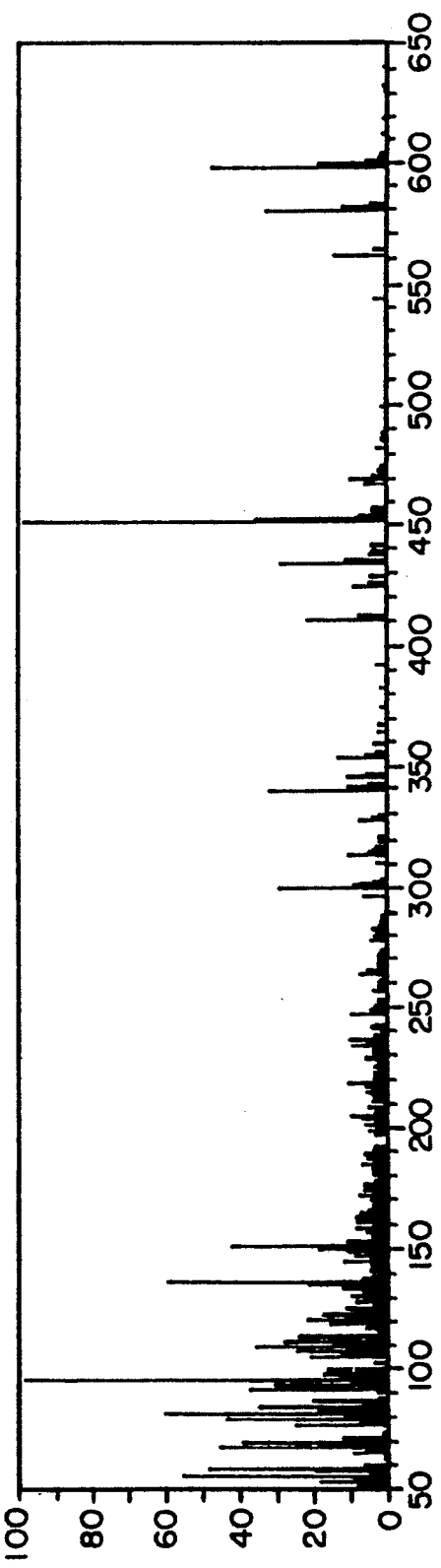
FIG. XXV

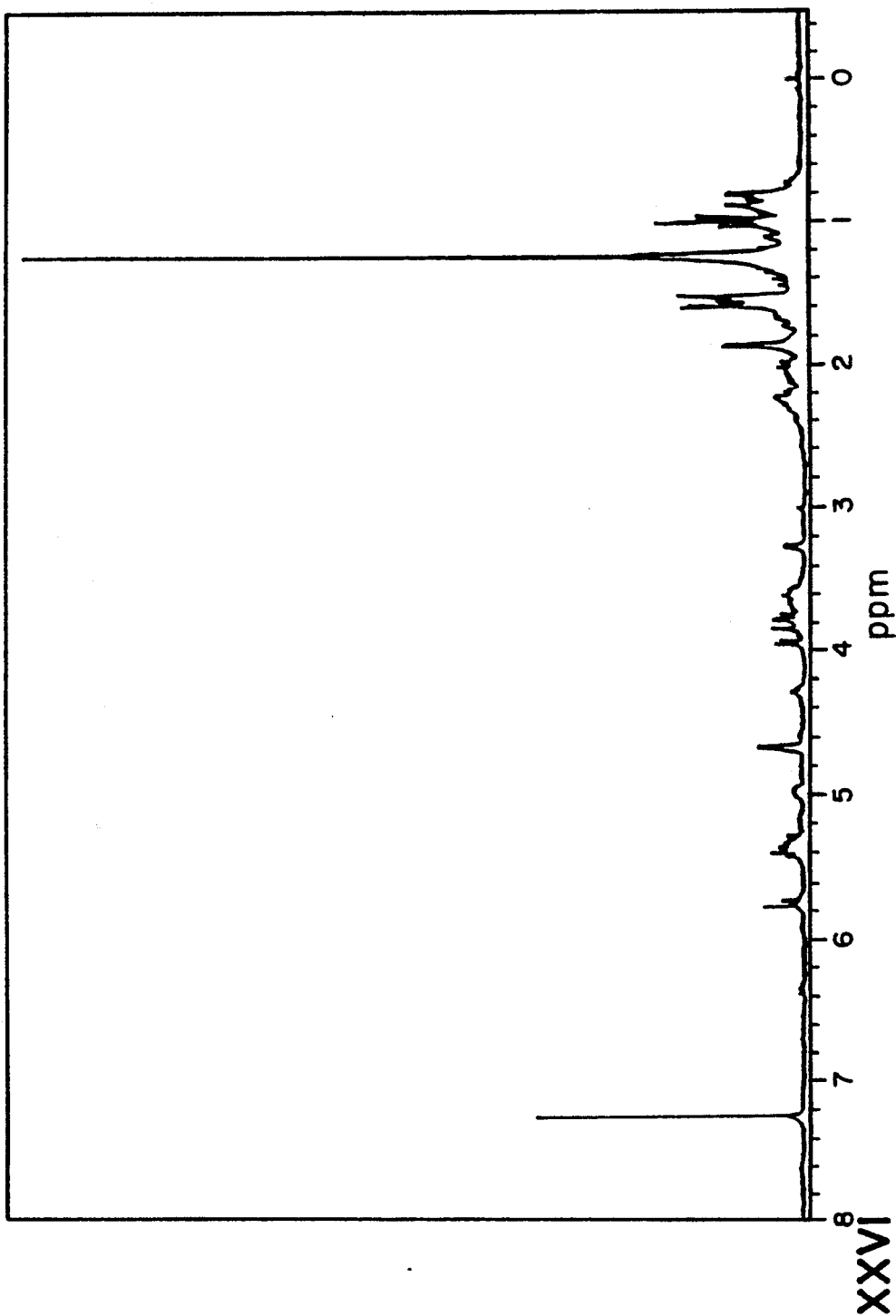

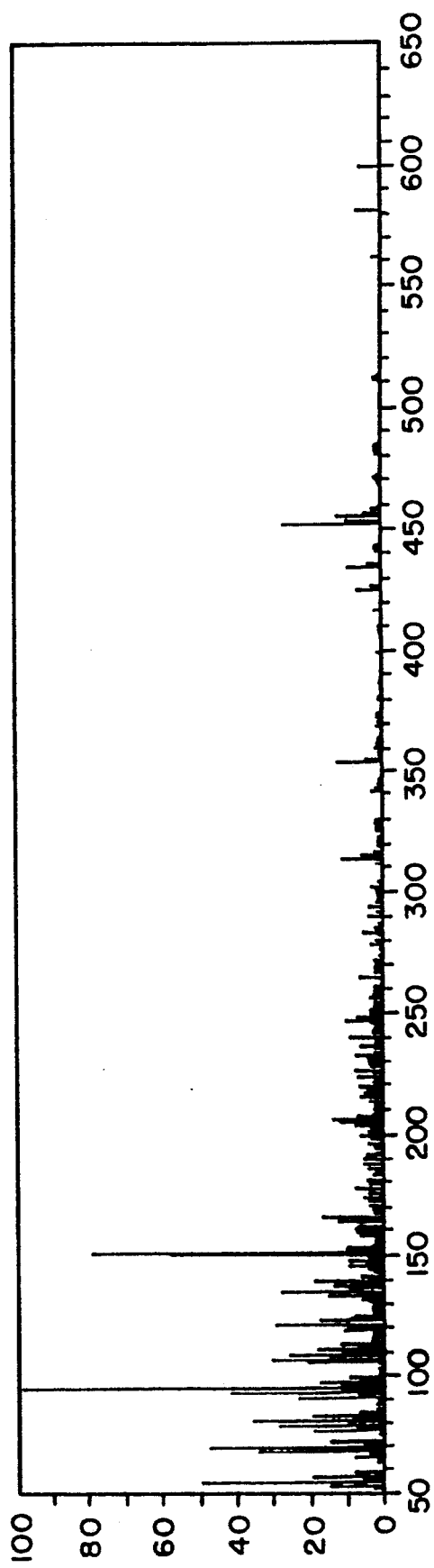
FIG. XXVII

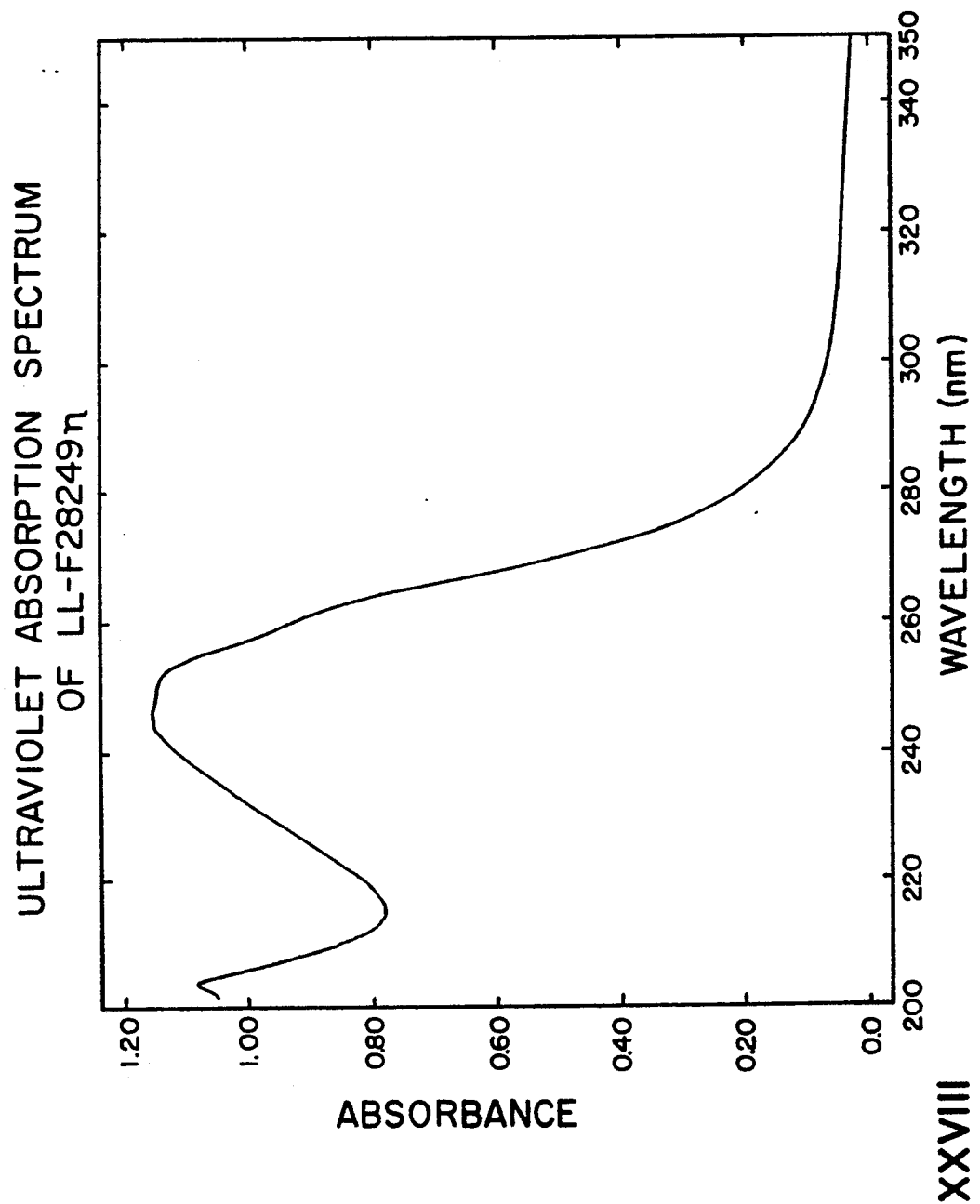

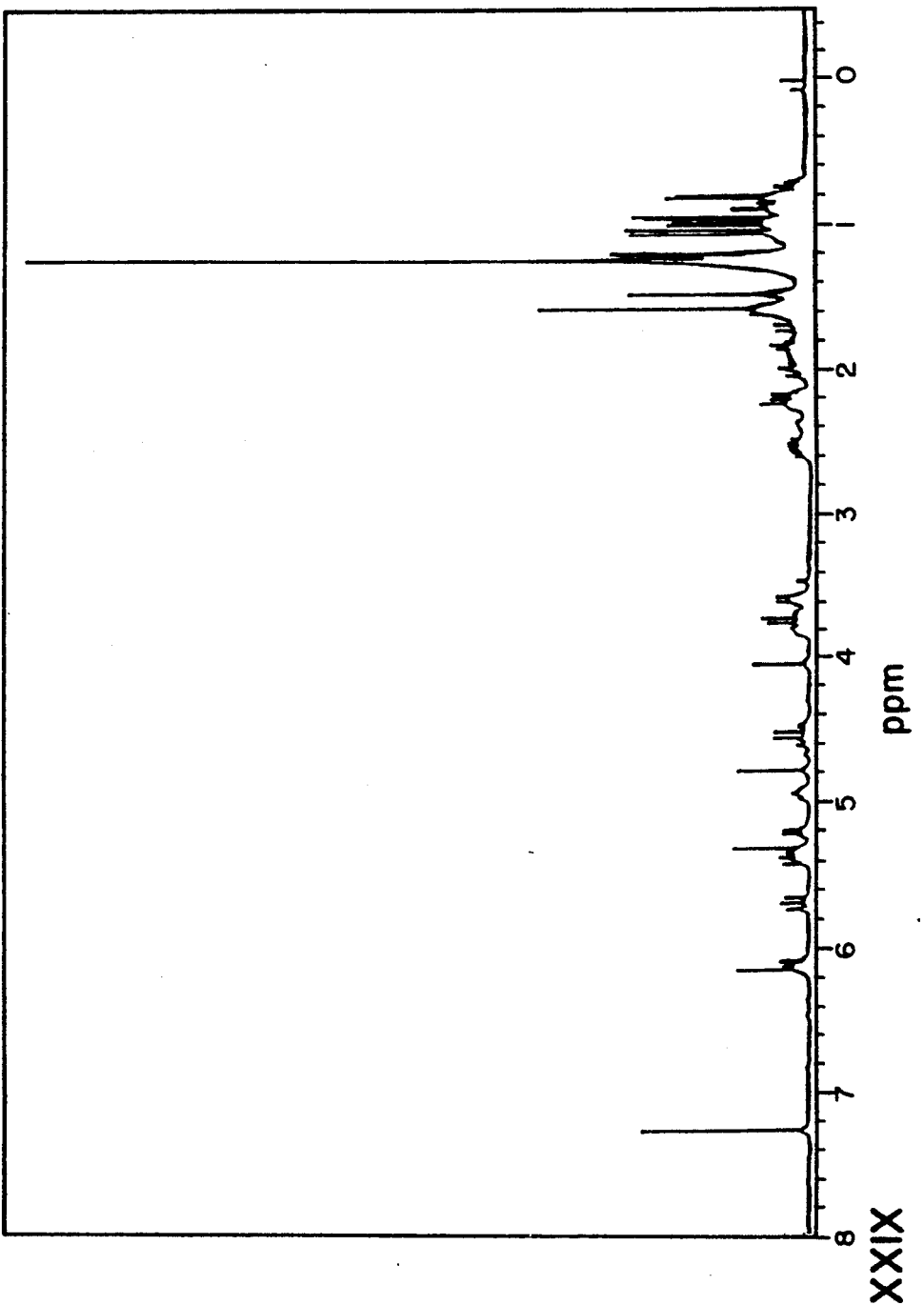

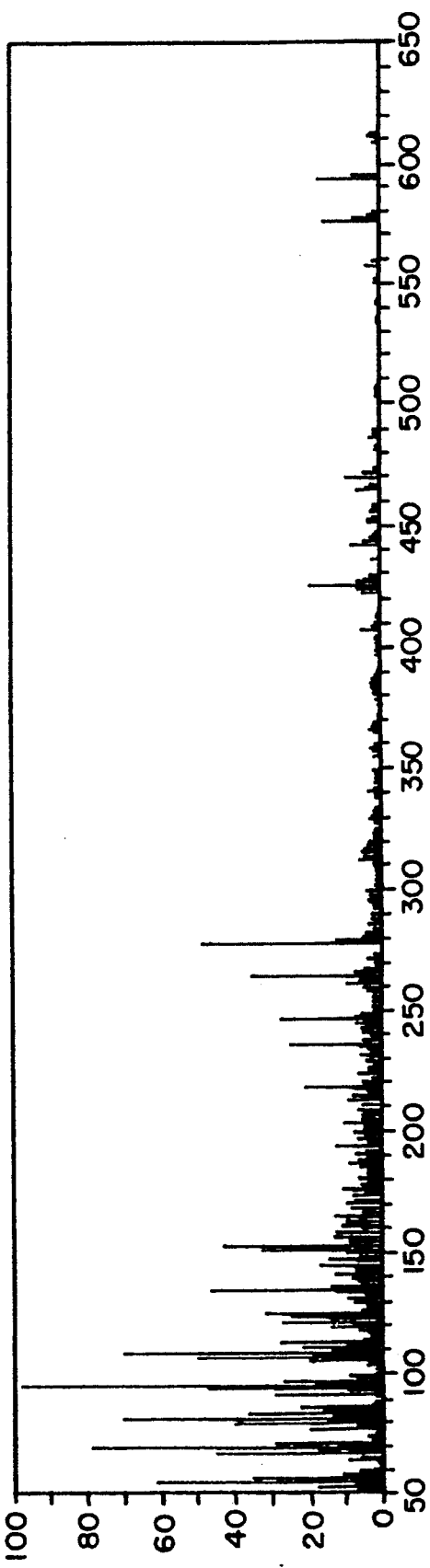
FIG. XXX

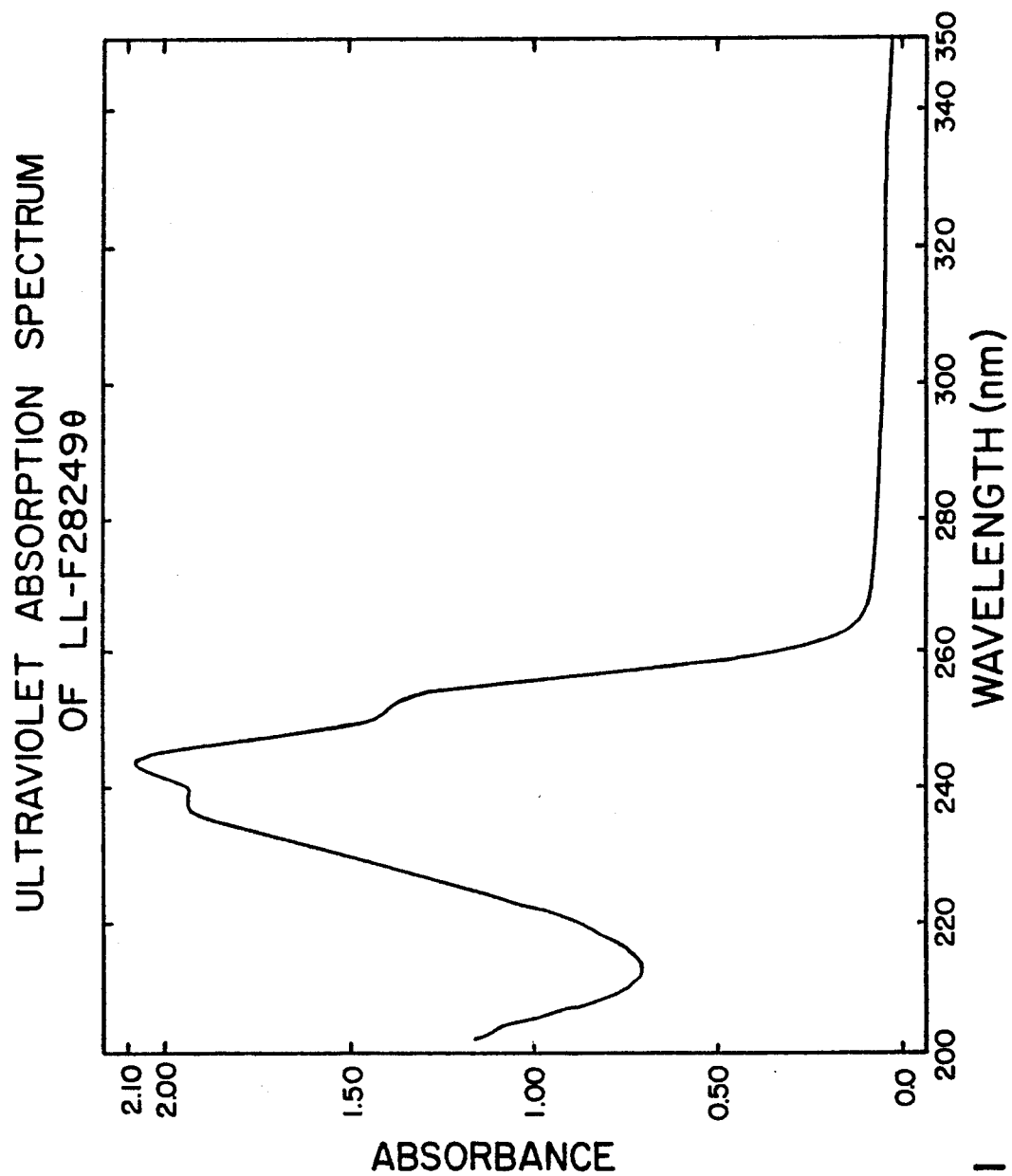
FIG. XXXI

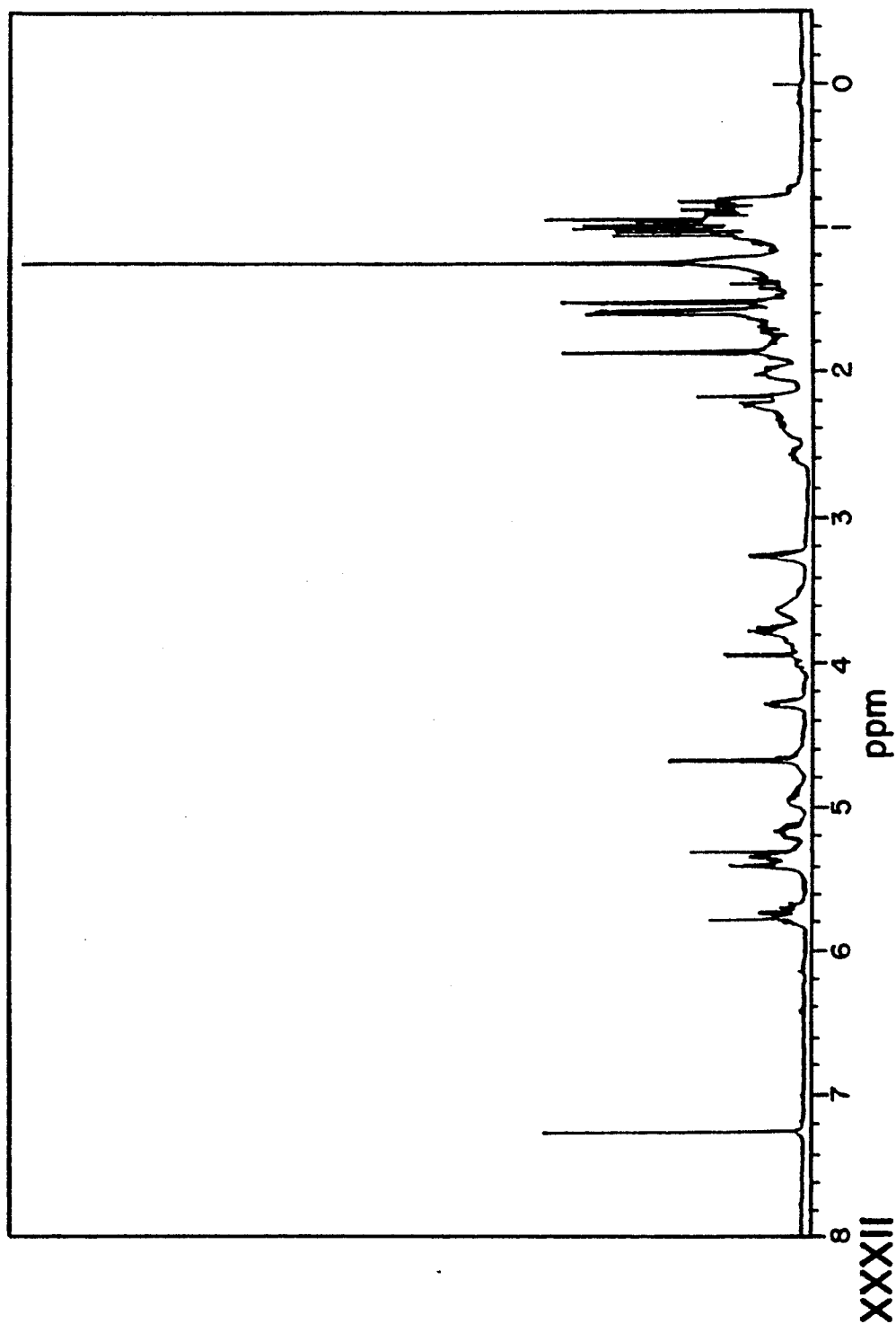
FIG. XXXII

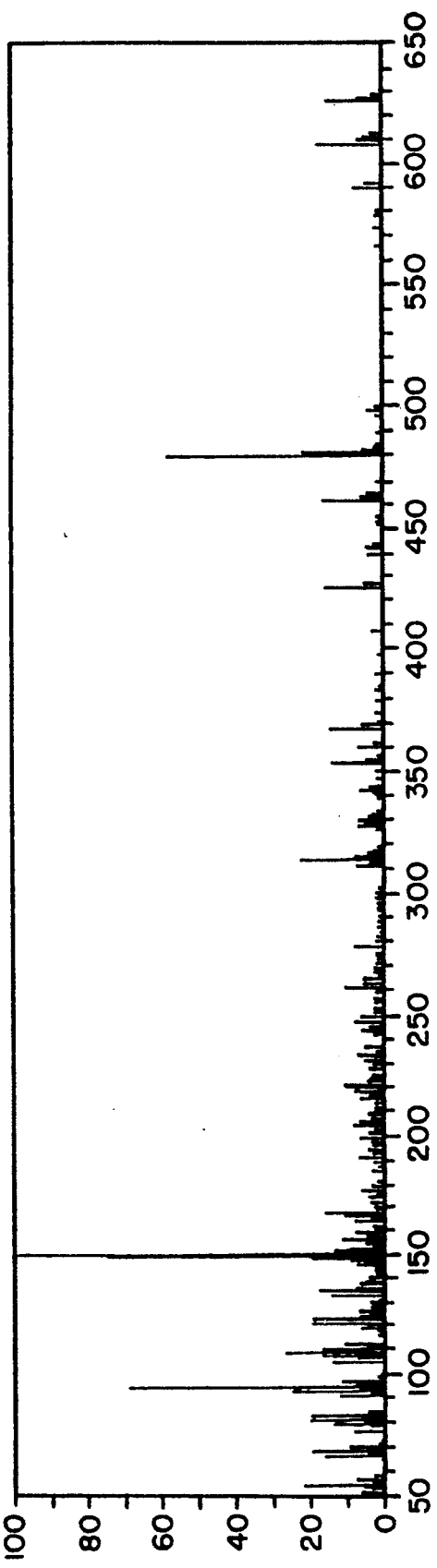
FIG. XXXIII

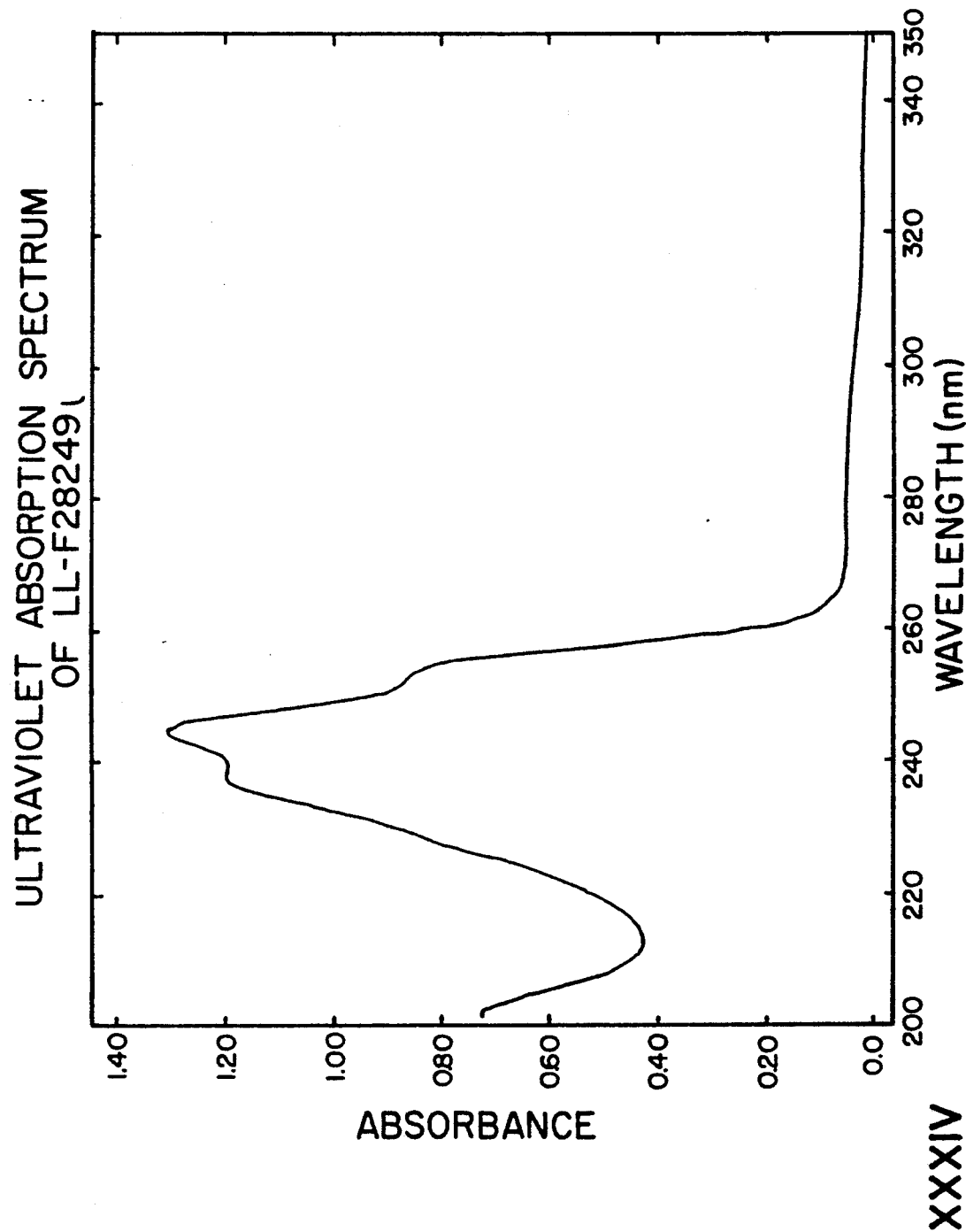
FIG. XXXIV

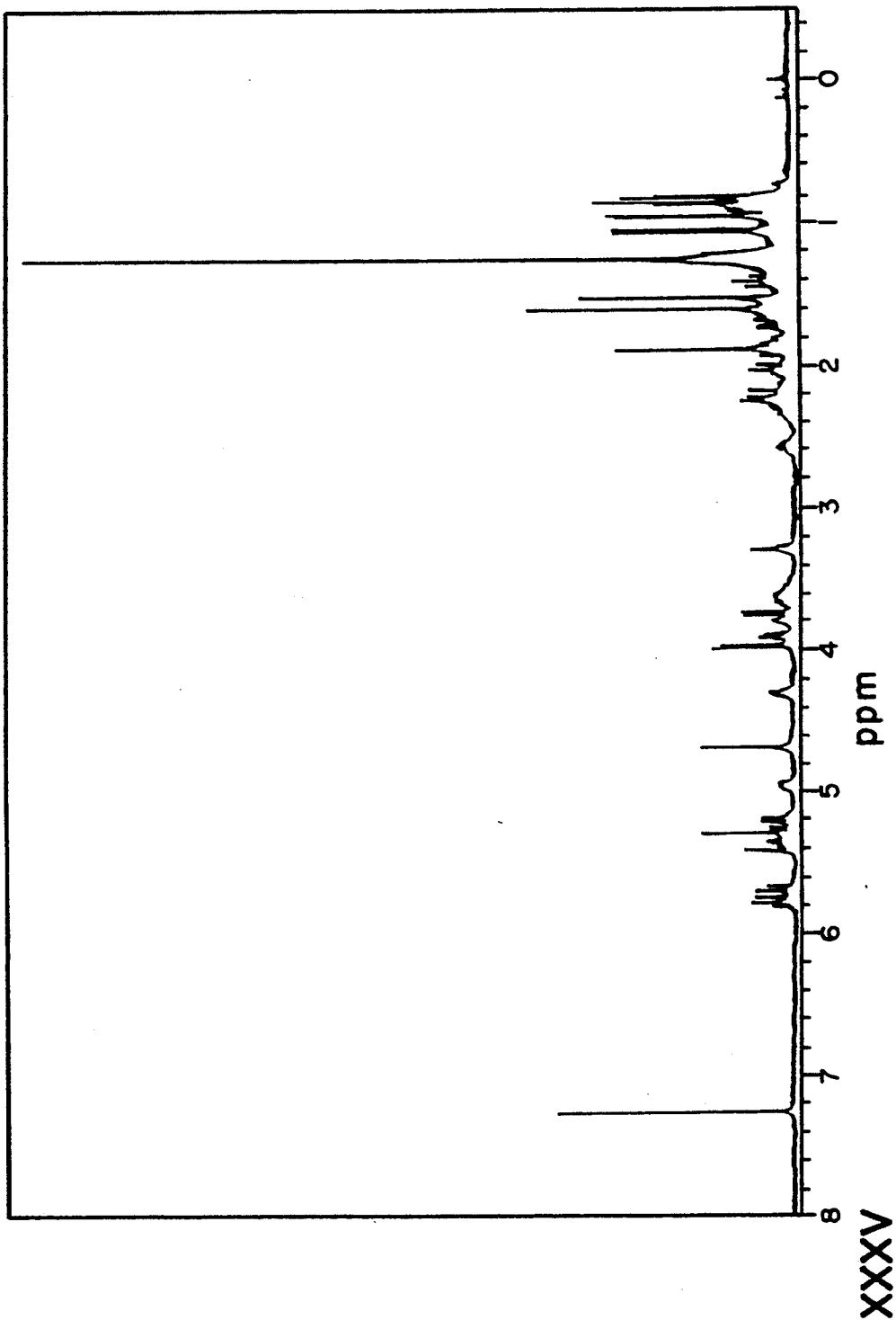
FIG. XXXV

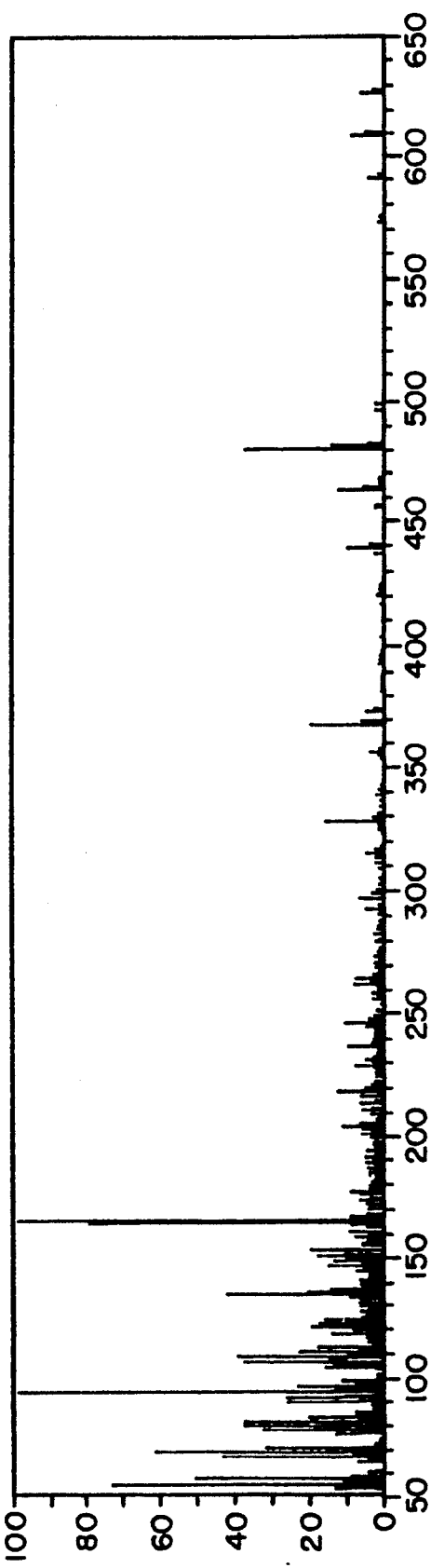
FIG. XXXVI

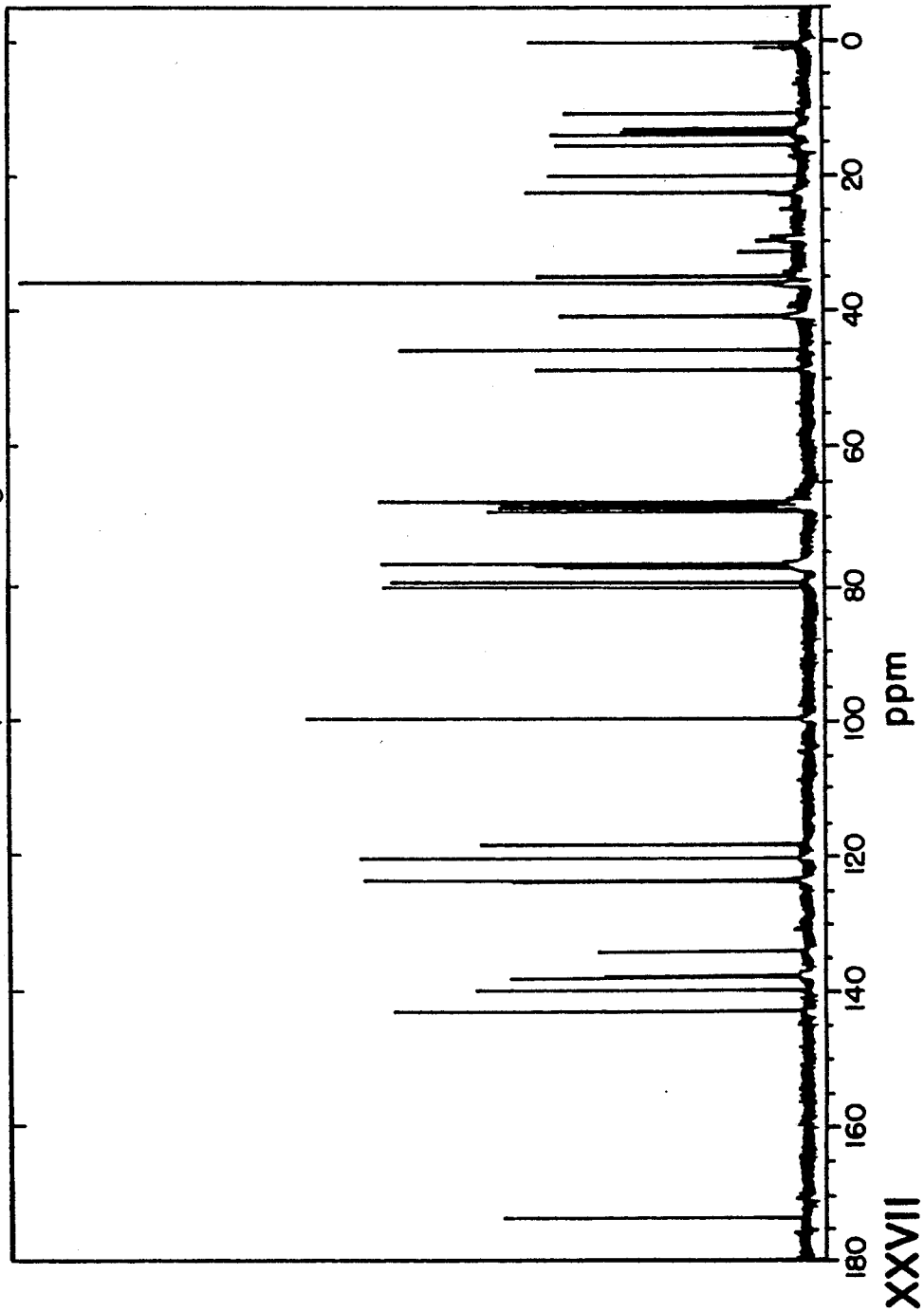
FIG. XXXVII

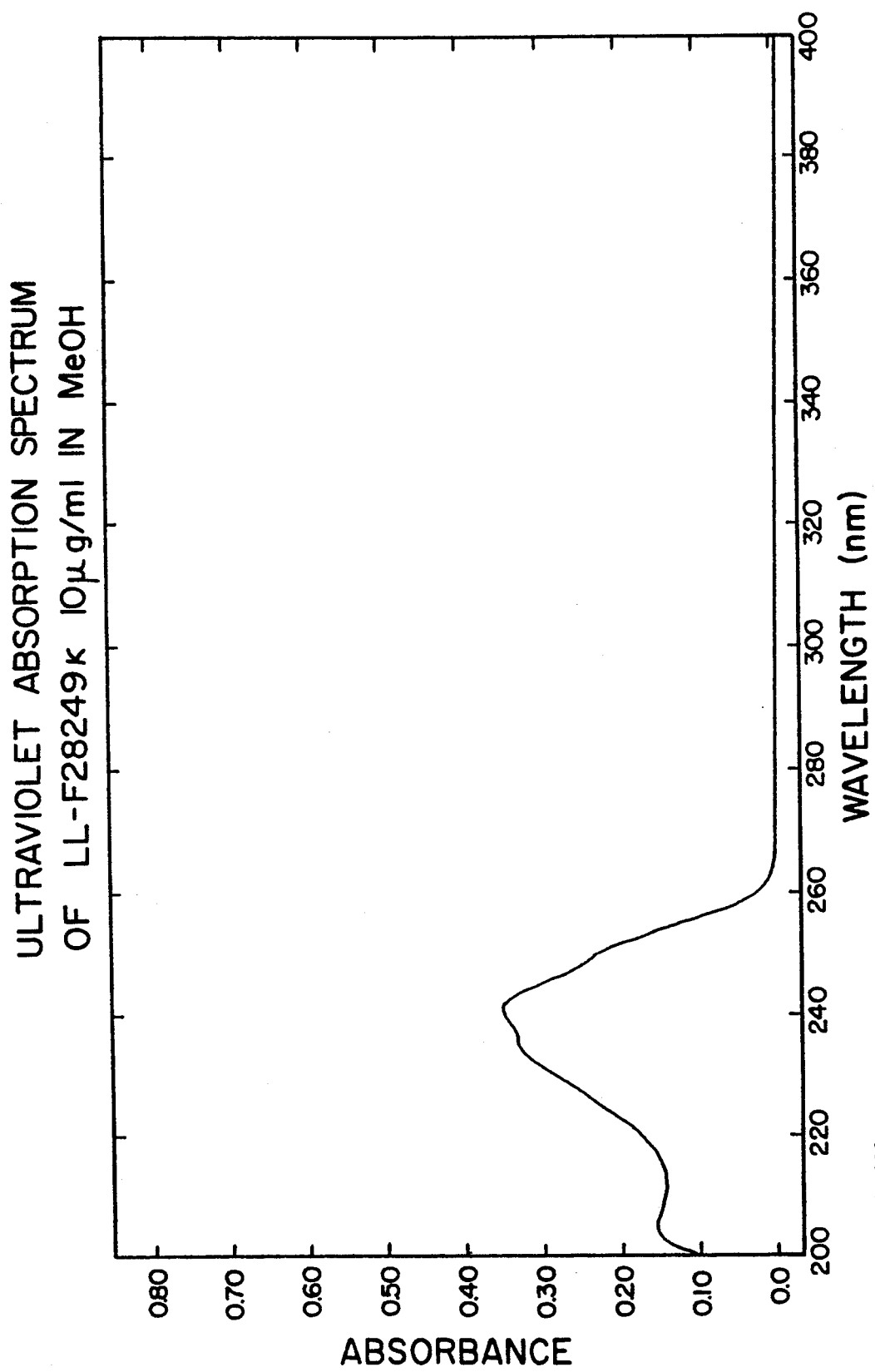
FIG. XXXVIII

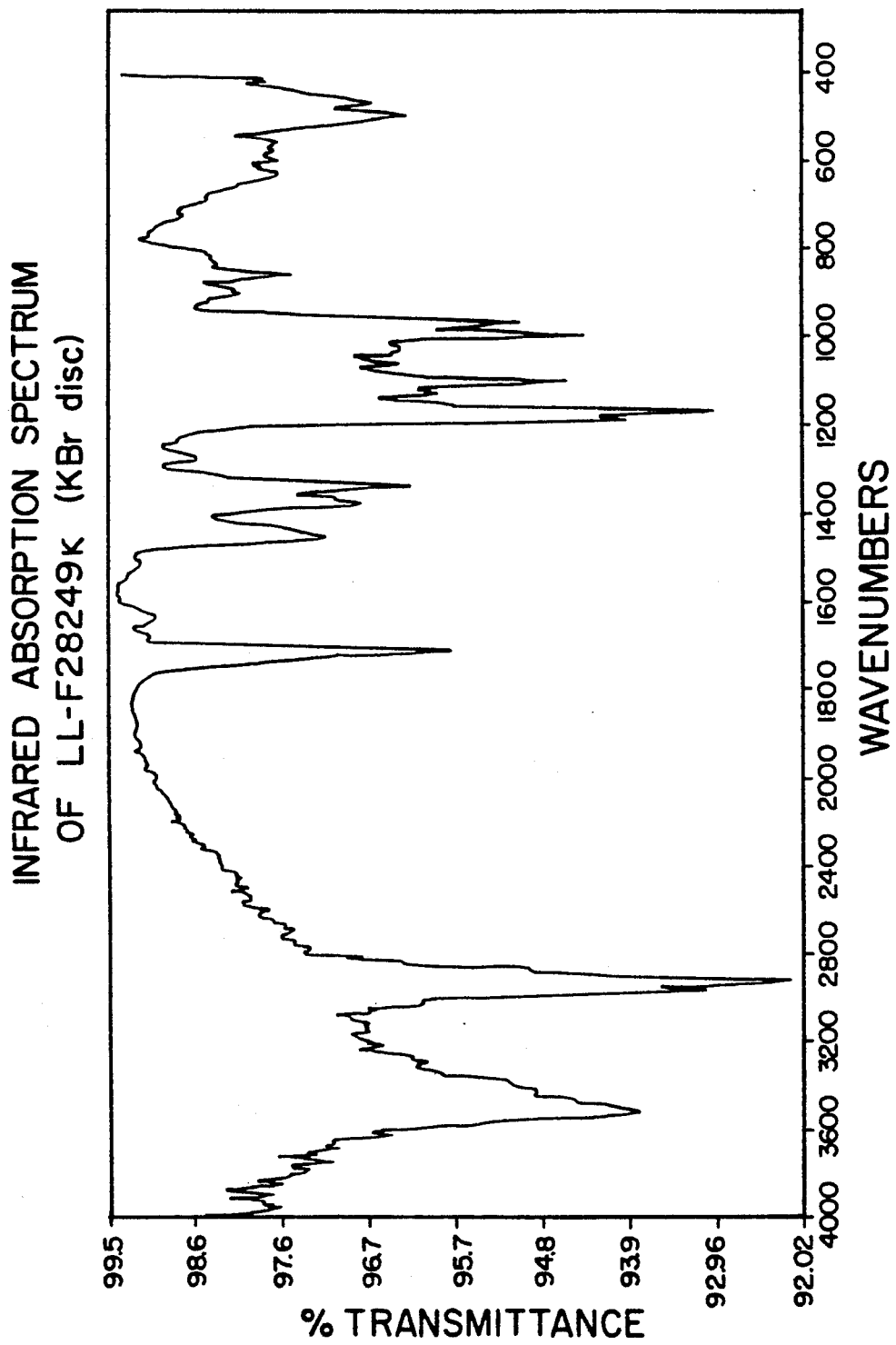
FIG. XXXIX

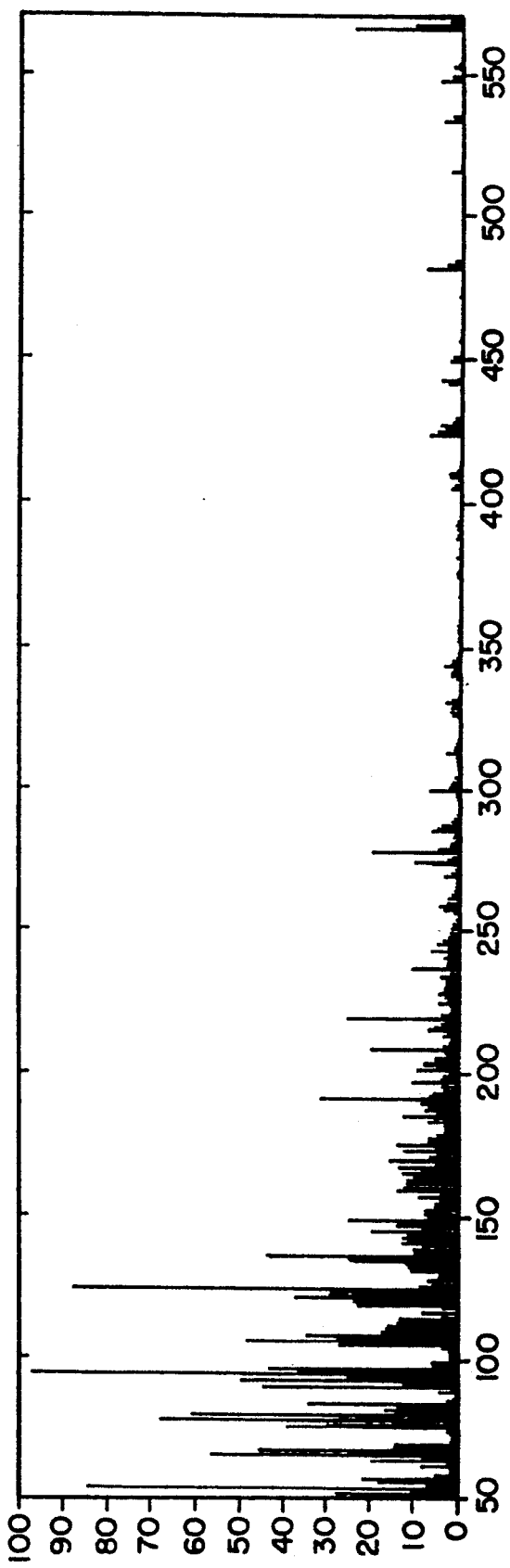
FIG. XL

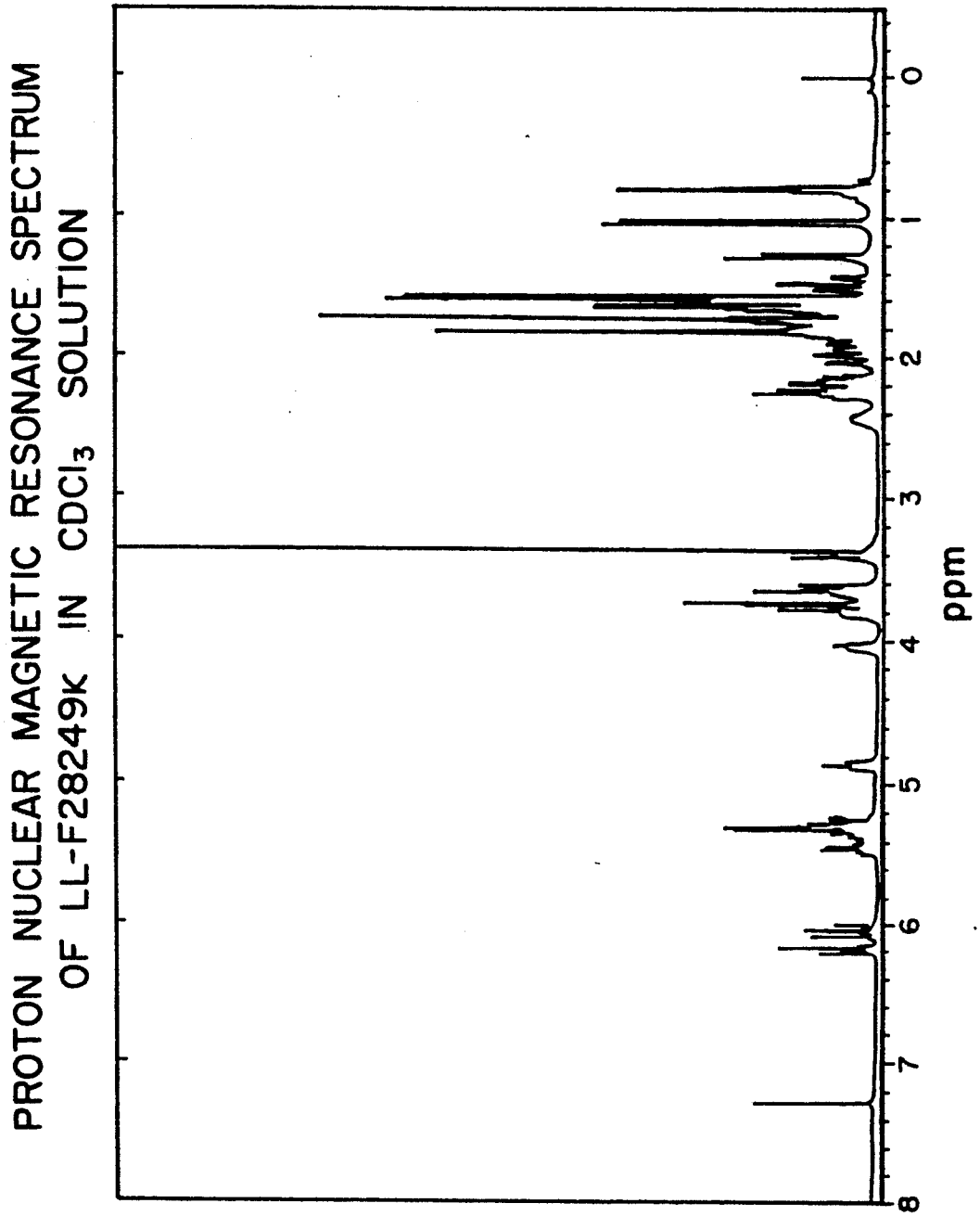
FIG. XLI

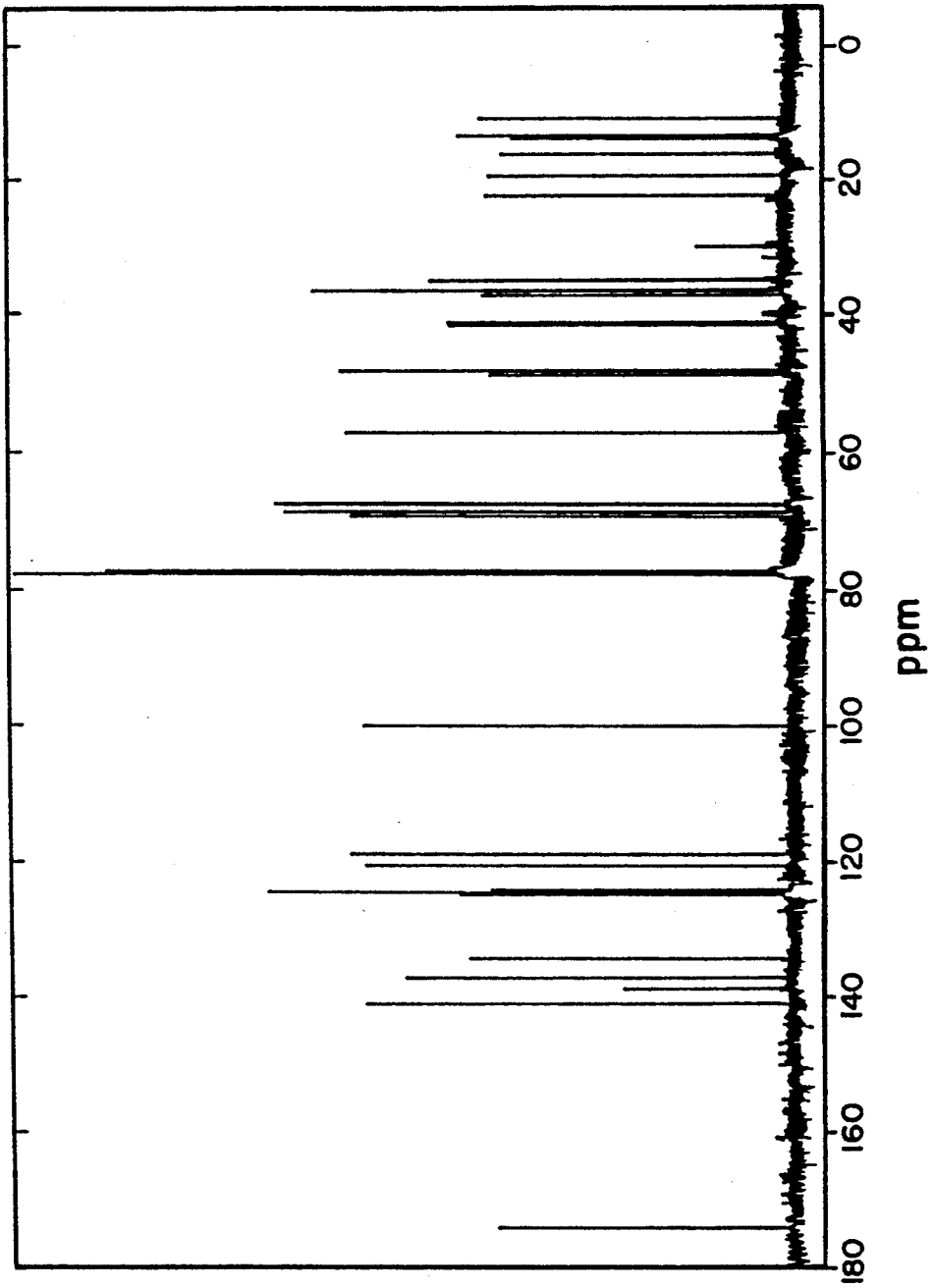
FIG. XLII

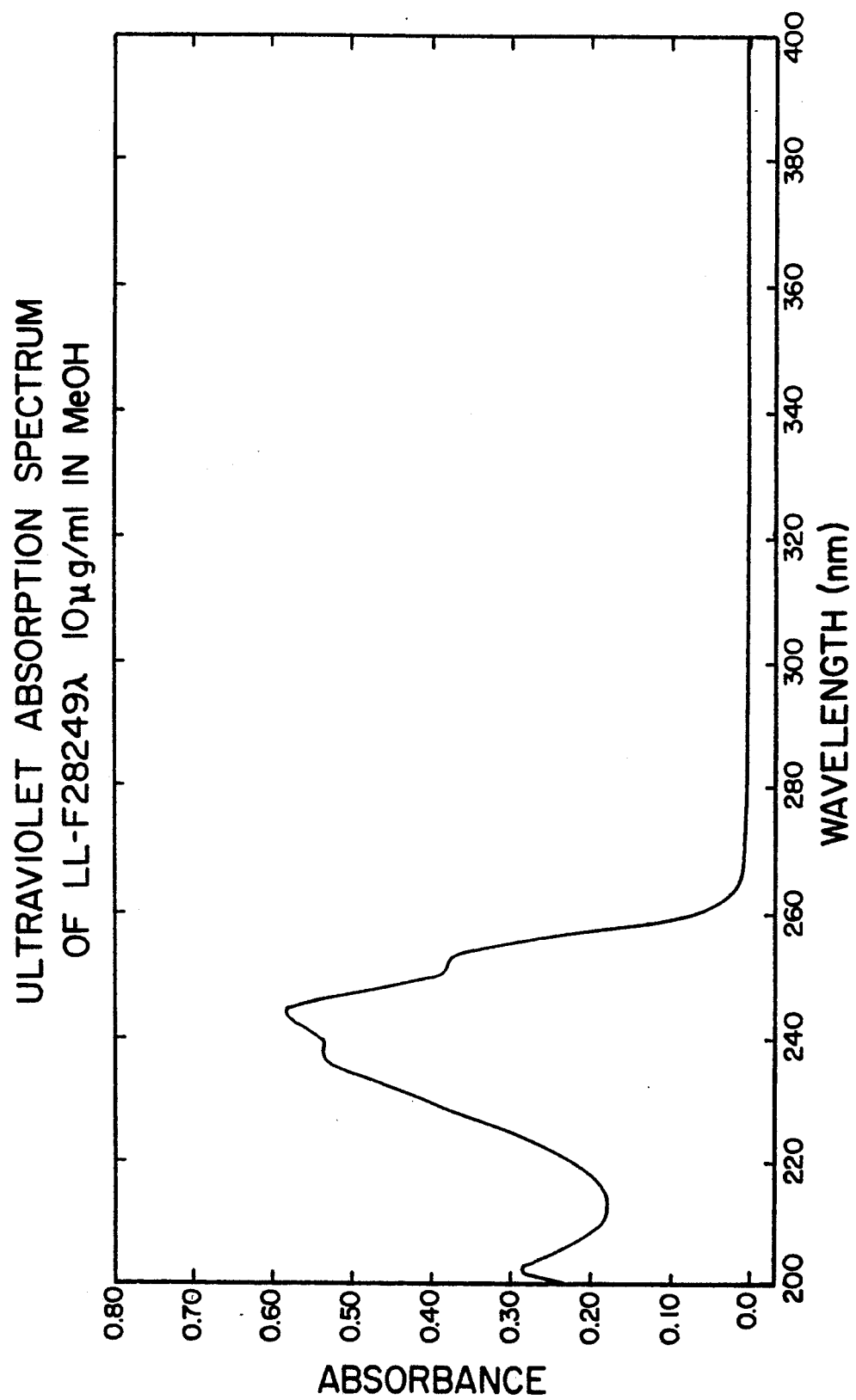
FIG. XLIII

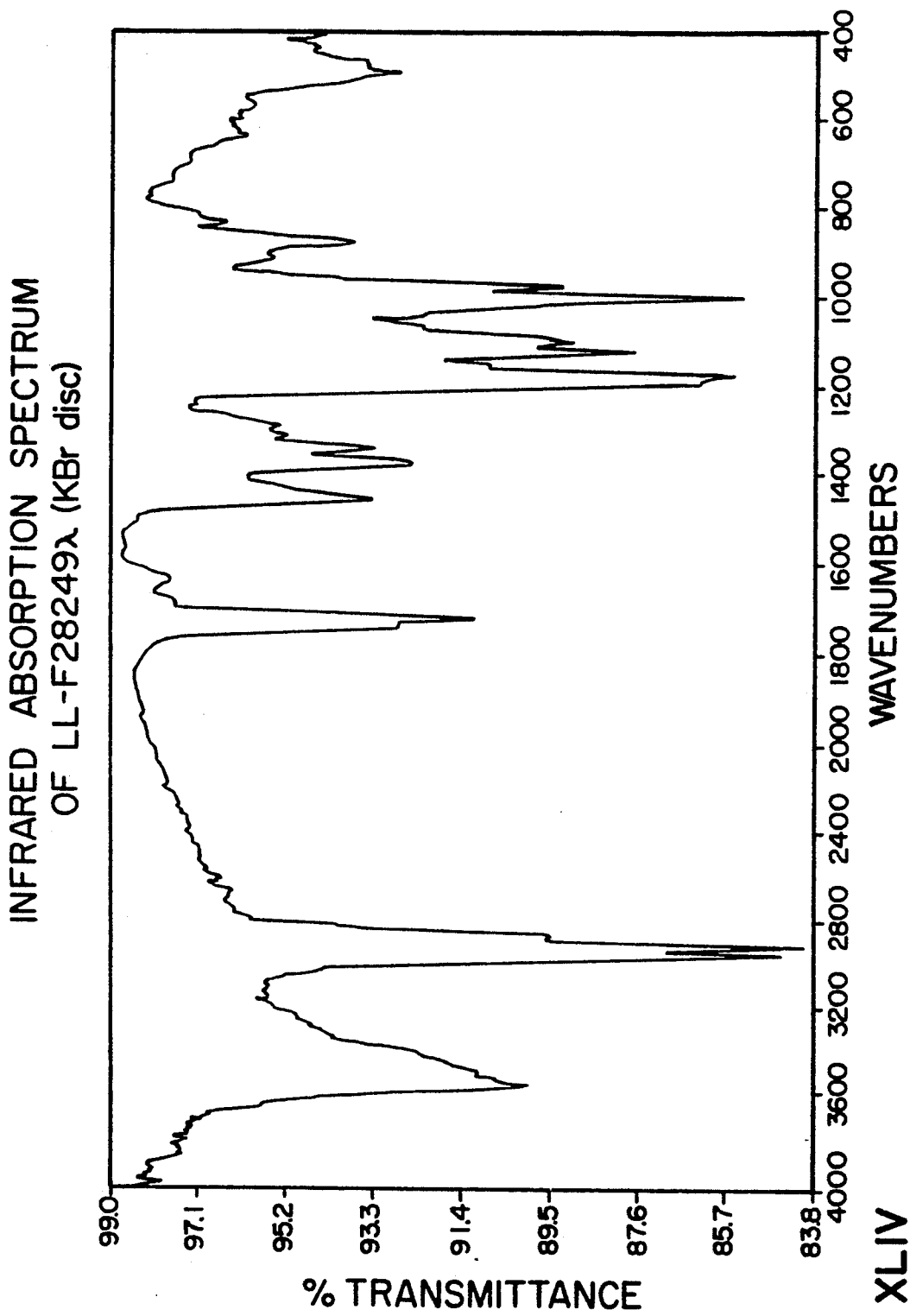
FIG. XLIV

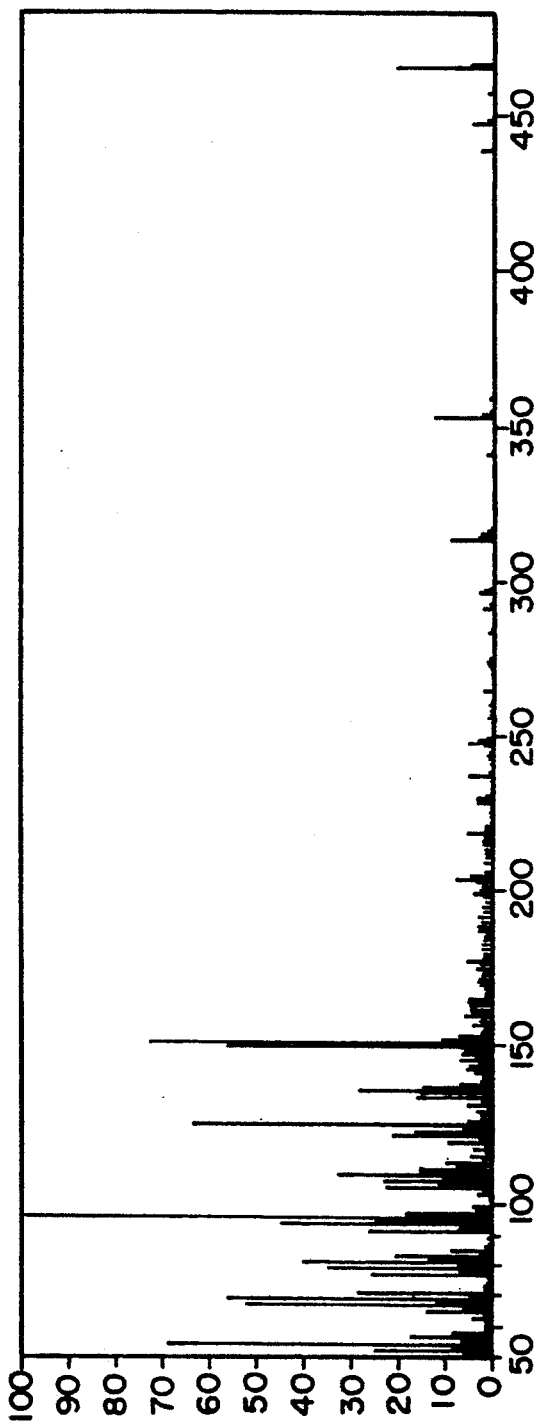
FIG. XLV

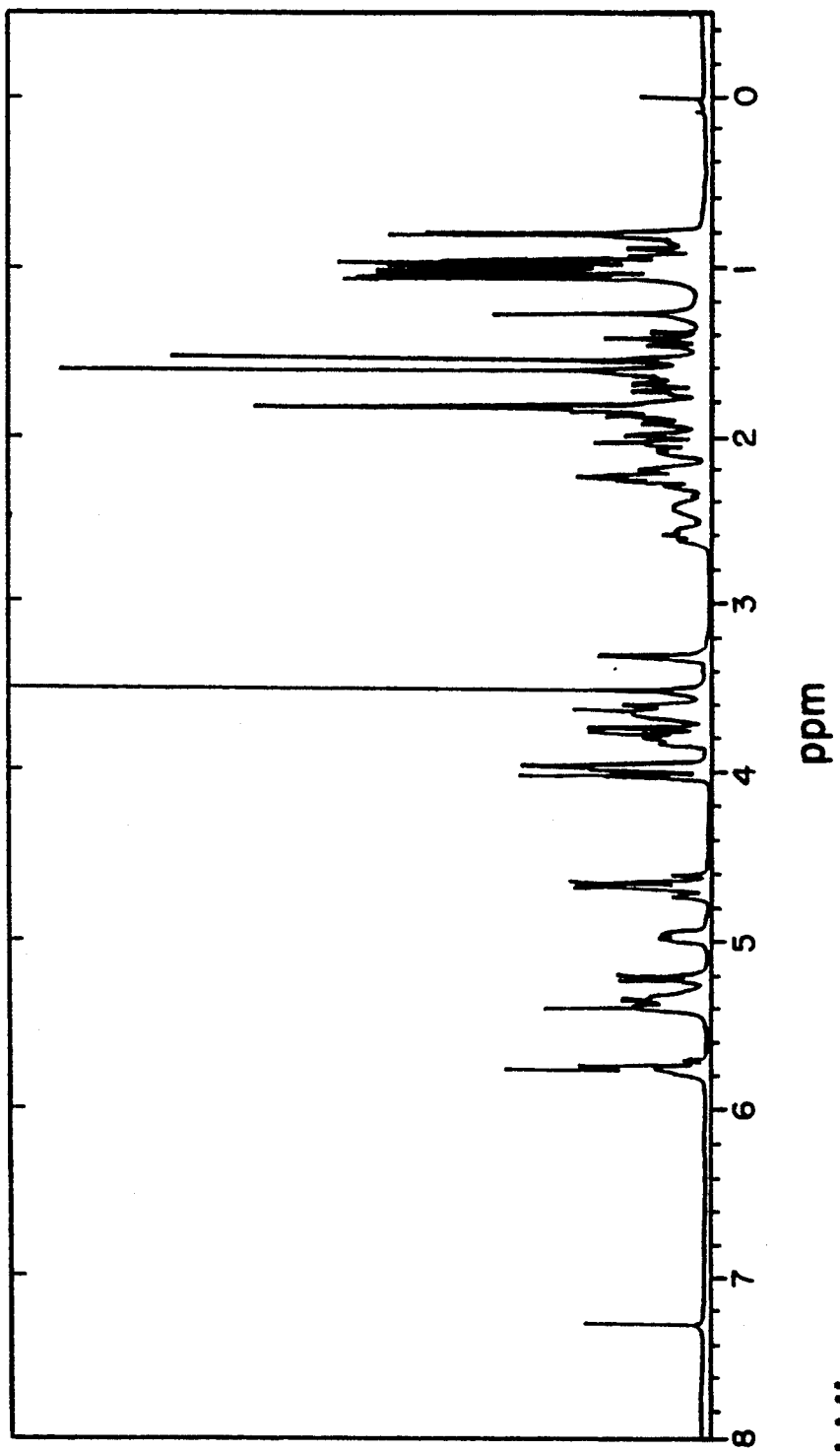
FIG. XLVI

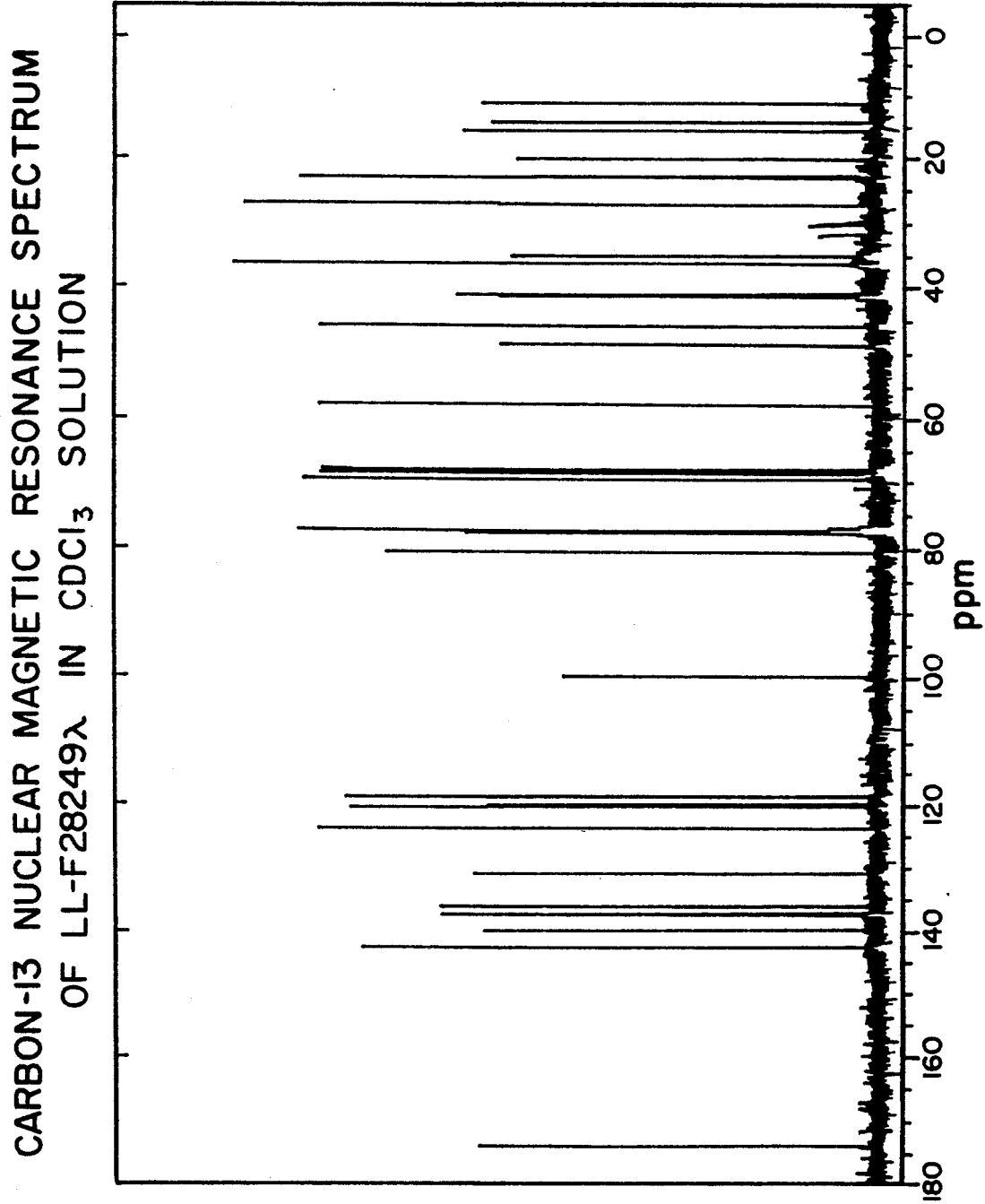

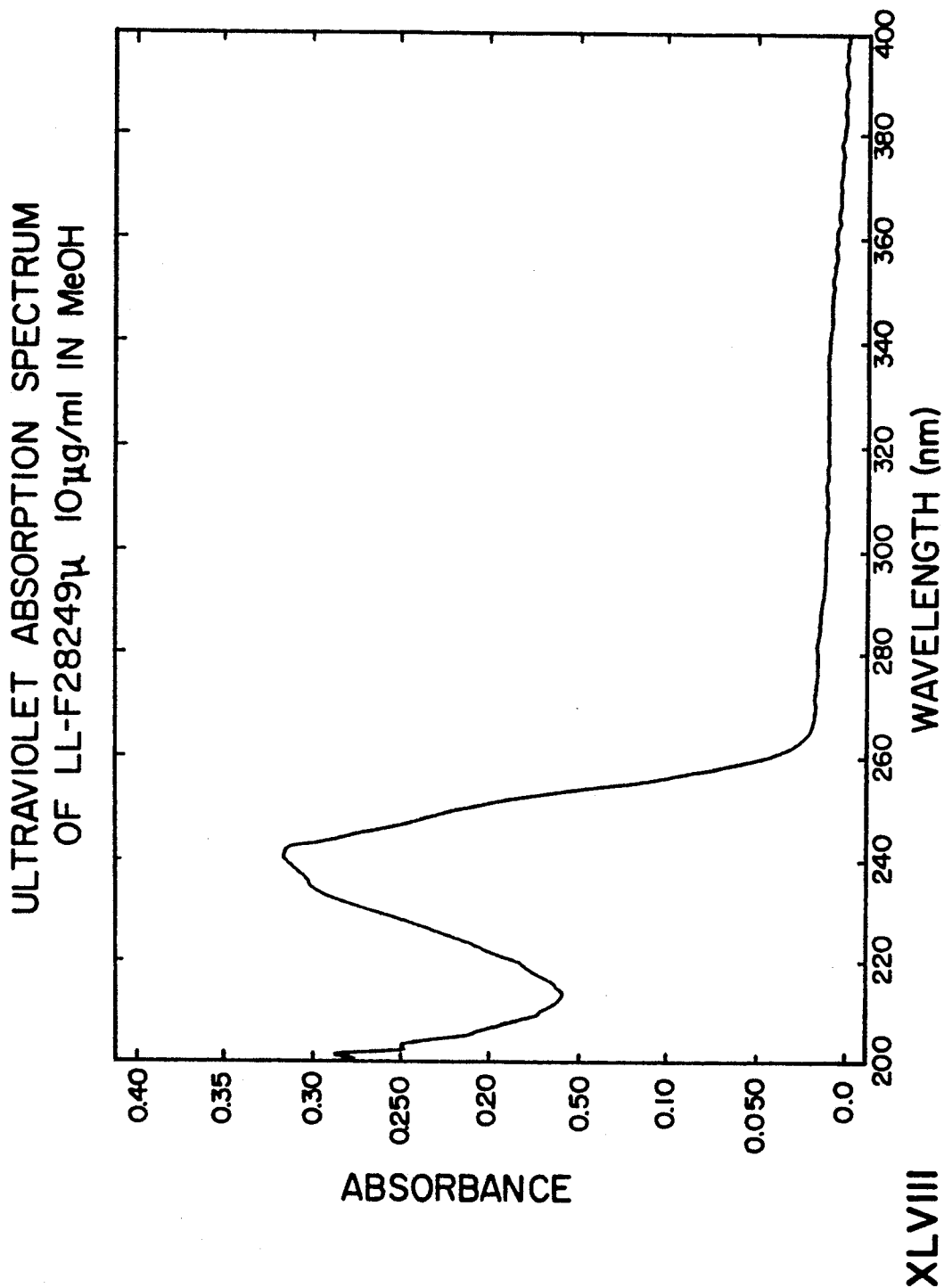
FIG. XLVIII

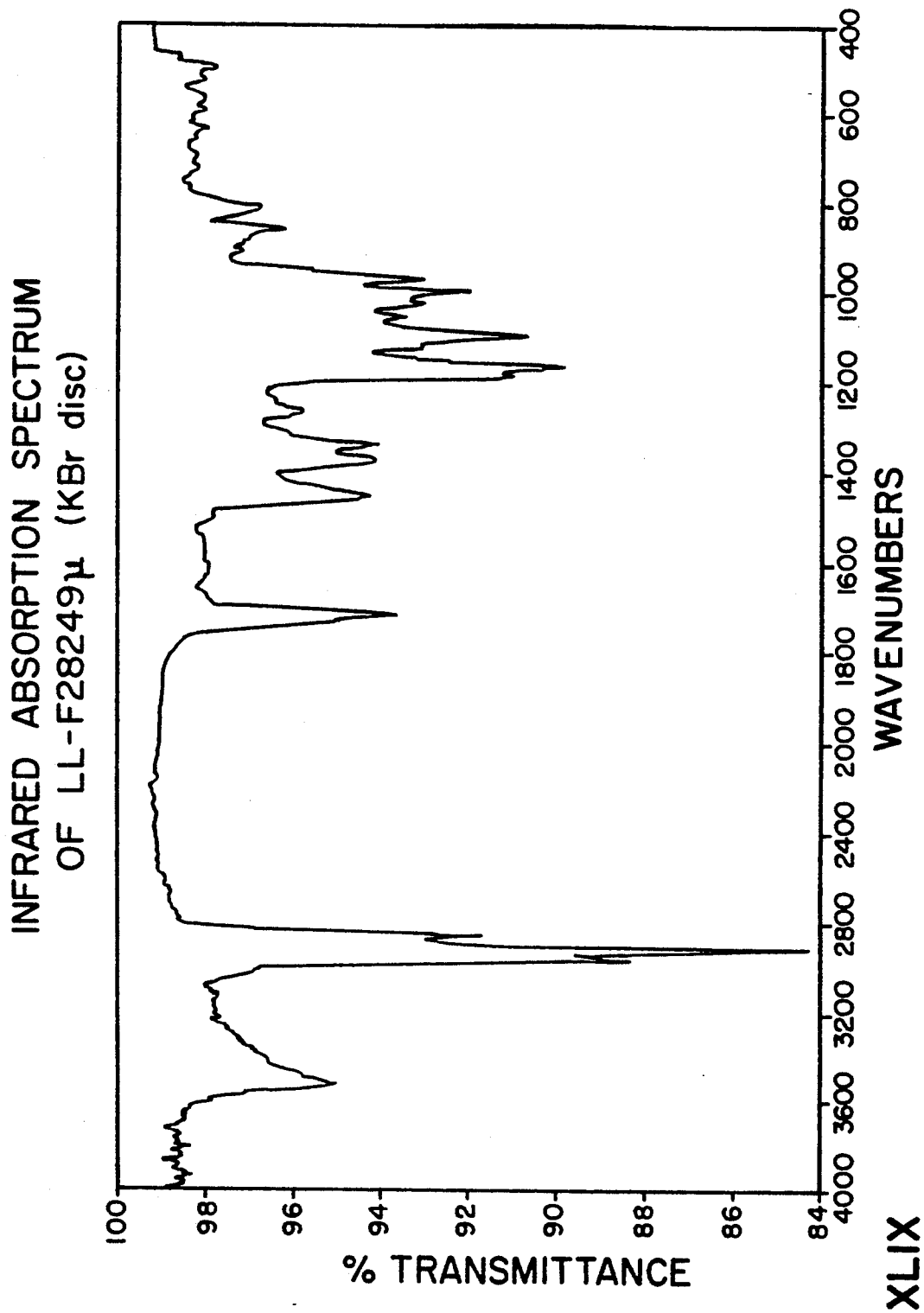
FIG. XLIX

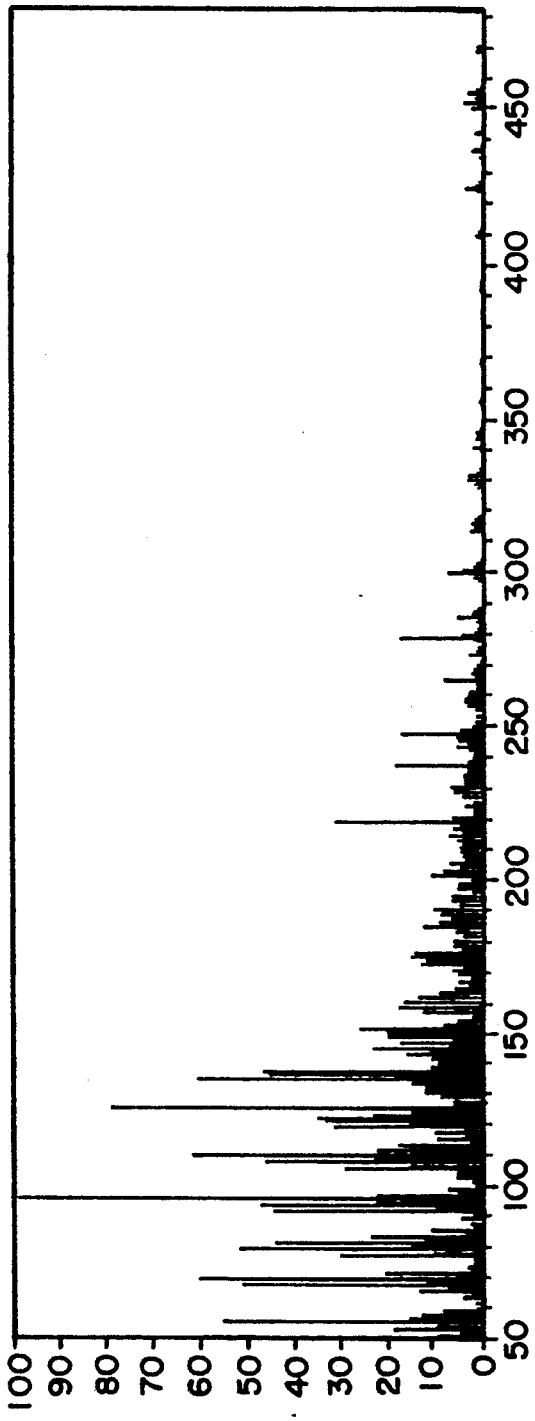
FIG. L

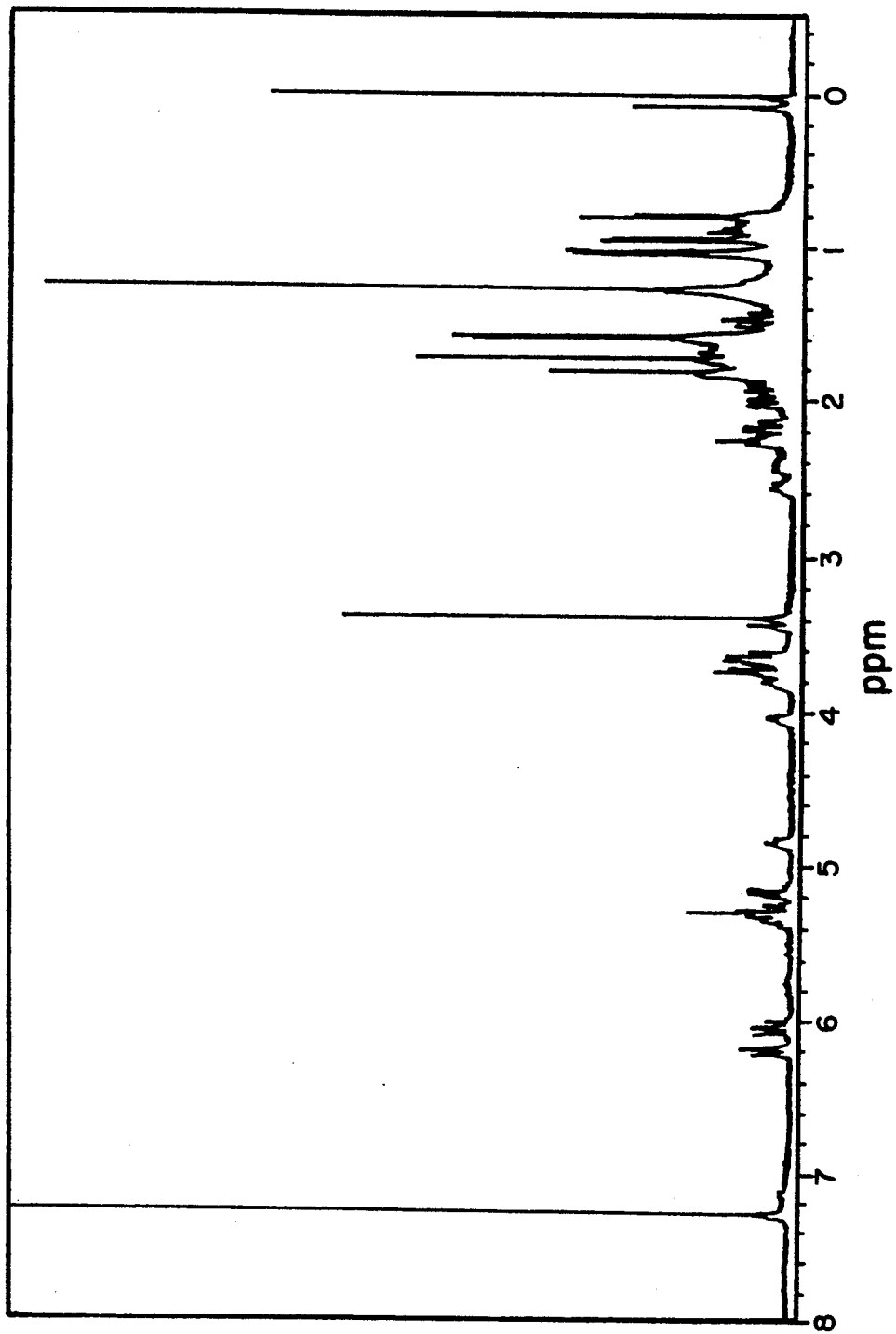
FIG. LI

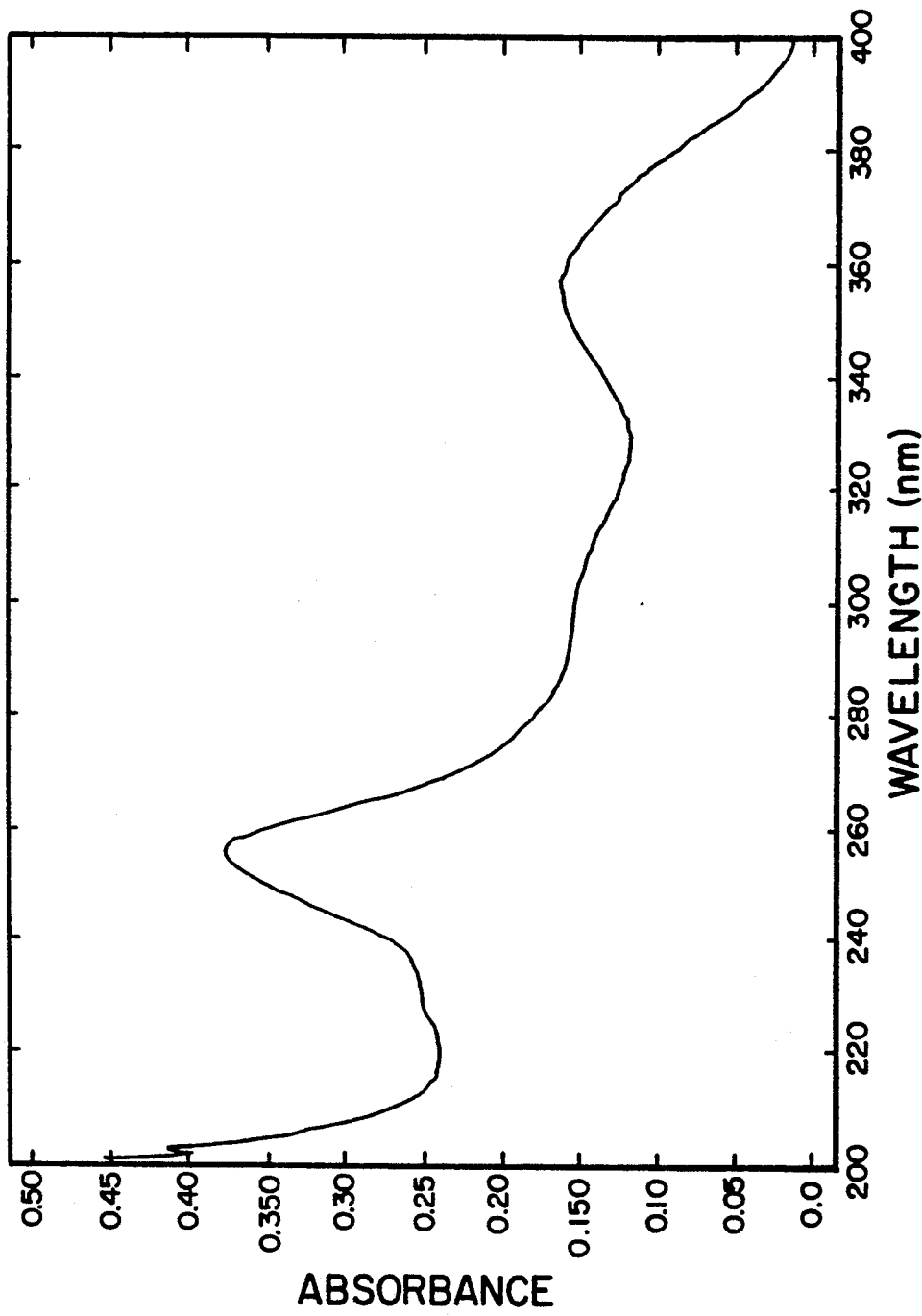
FIG. LII

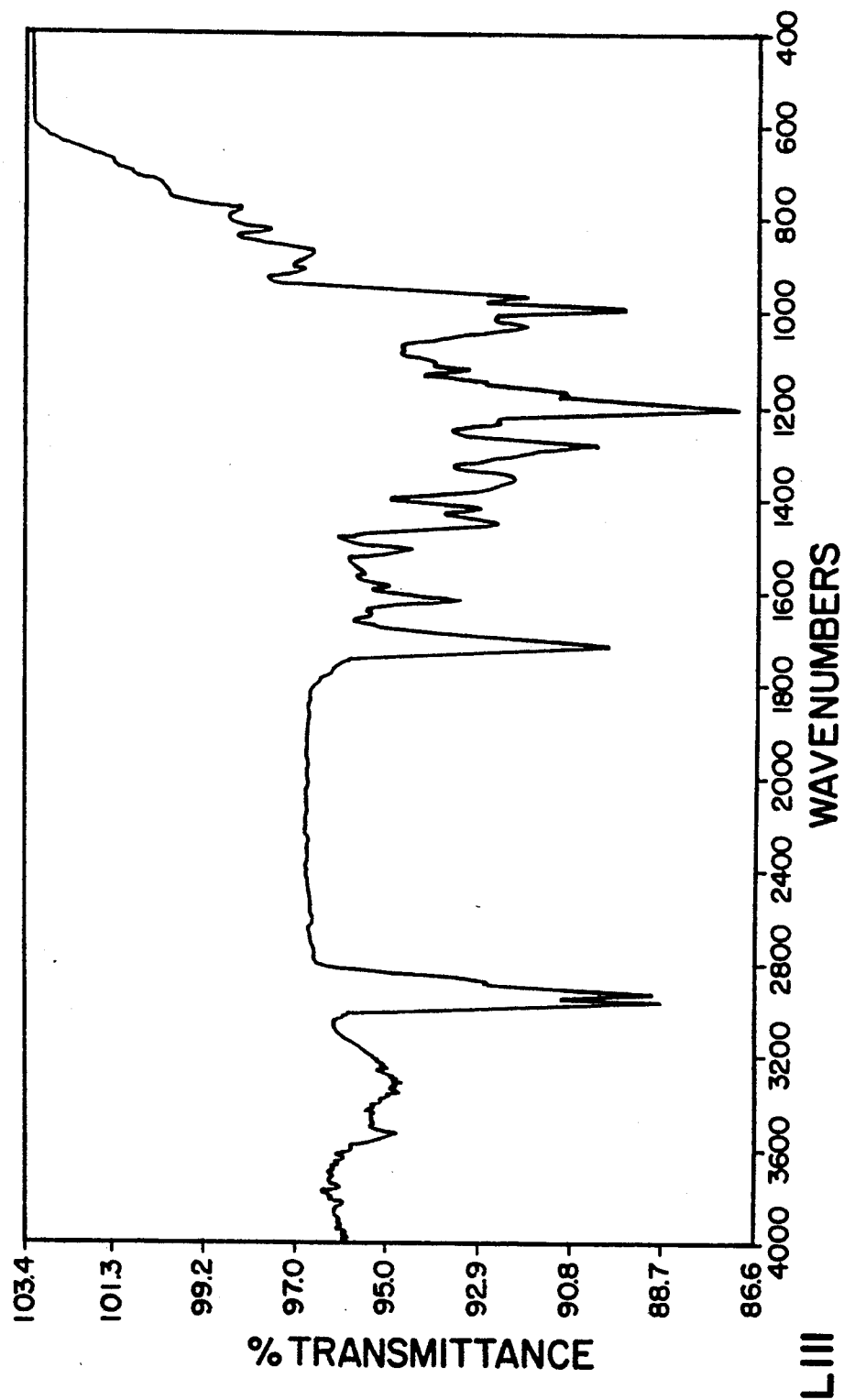
FIG. LIII

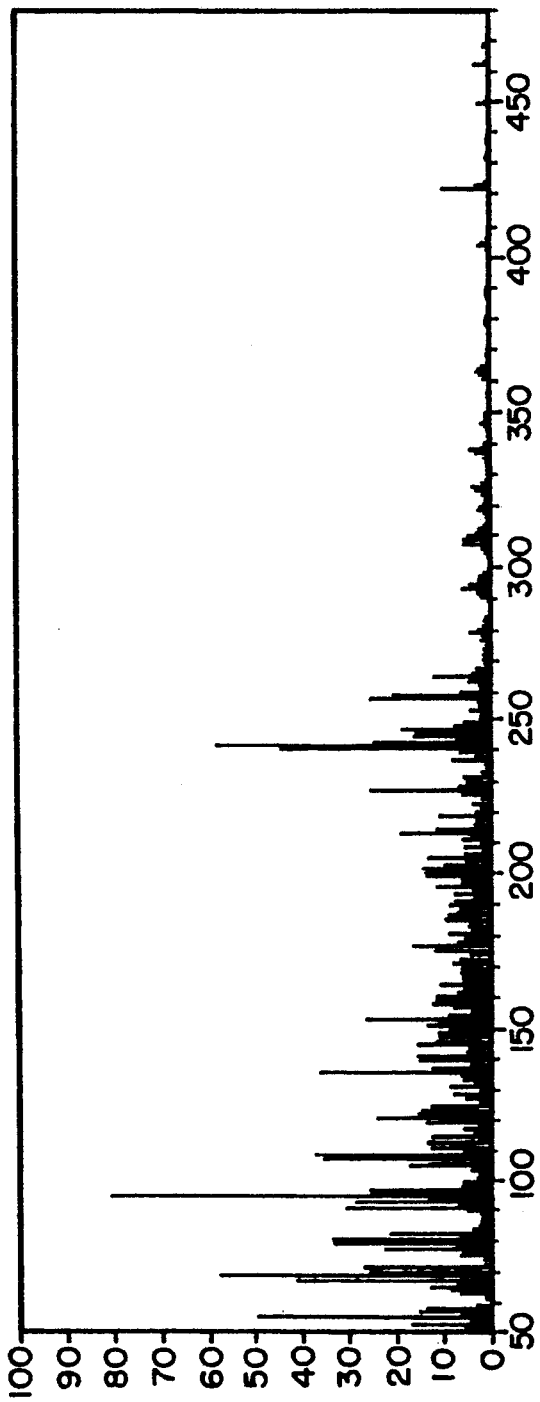
FIG. LIV

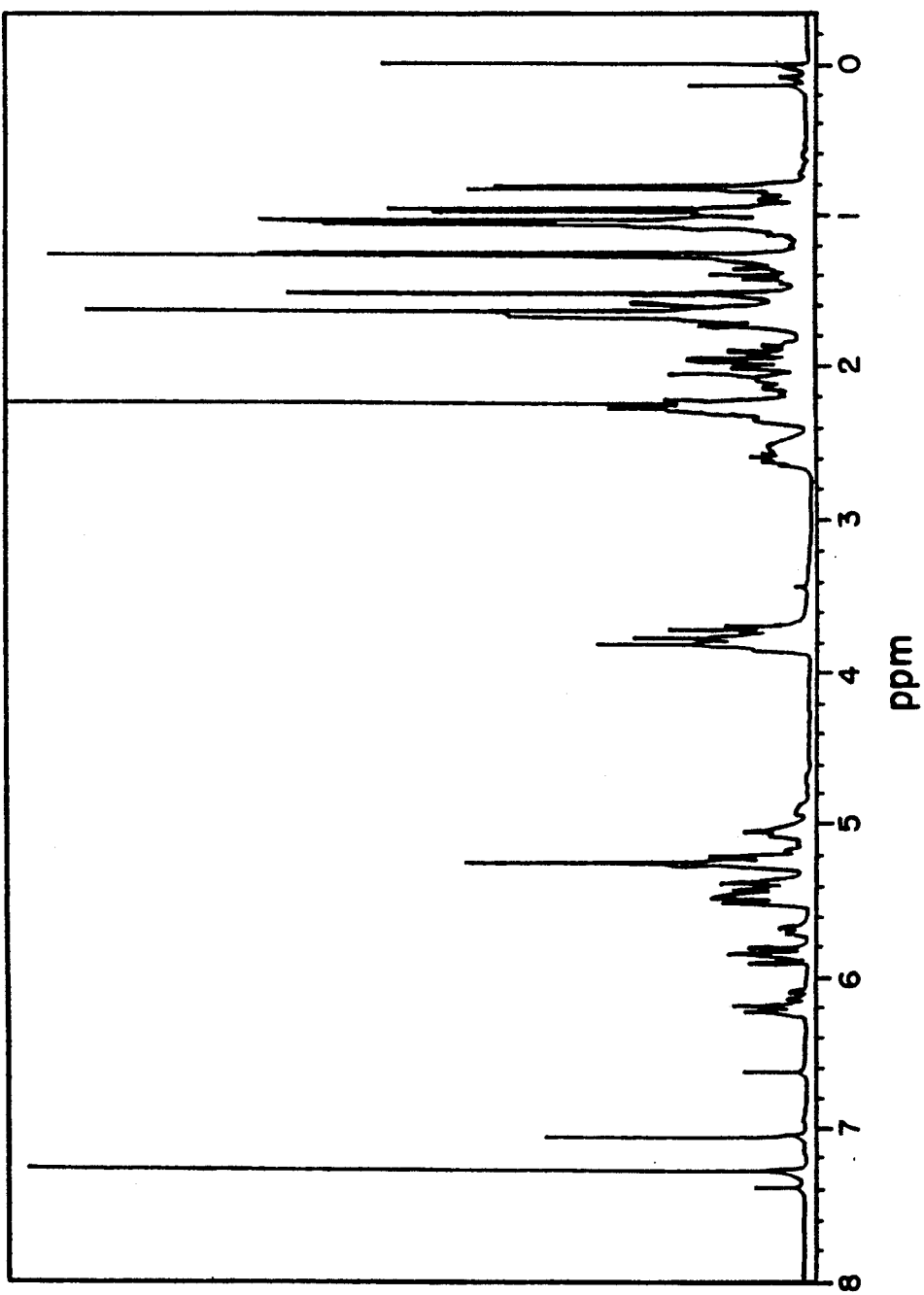
FIG. LV

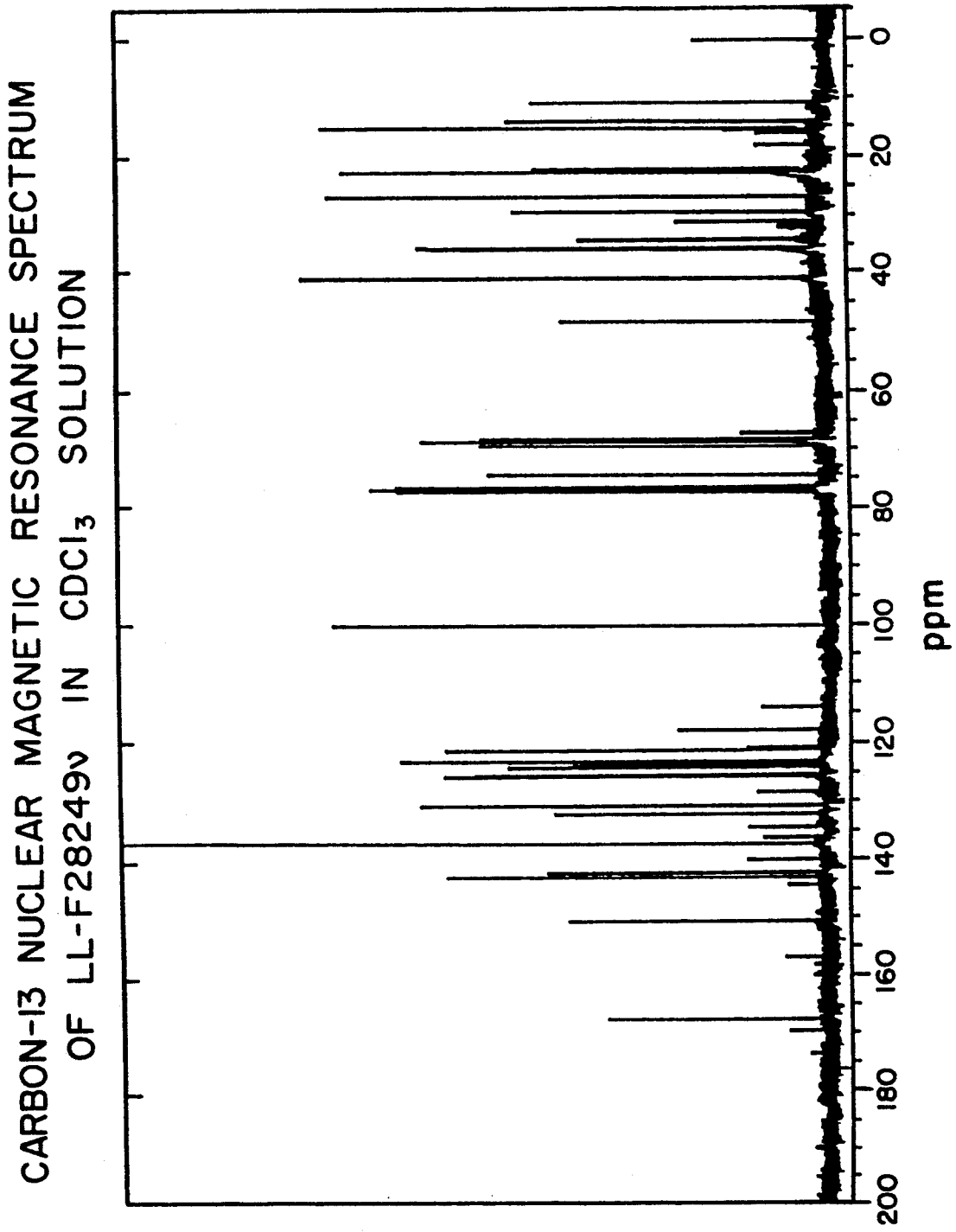
FIG. LVI

MACROLIDE ANTIBIOTIC COMPOUNDS

This is a continuation of co-pending, allowed application Ser. No. 06/732,252, now U.S. Pat. No. 5,106,994, filed May 10, 1985, which is a continuation-in-part of application Ser. No. 06/617,650, filed Jun. 5, 1984, abandoned.

BACKGROUND OF THE INVENTION

The present invention relates to new antibiotic compounds, collectively identified as LL-F28249, which are produced by the fermentation of a nutrient medium with the strain of the microorganism Streptomyces cyaneogriseus subsp. noncyanogenus LL-F28249, NRRL No. 15773 and to the pharmaceutically and pharmacologically-acceptable salts thereof.

SUMMARY OF THE INVENTION

The culture of Streptomyces cyaneogriseus subsp. noncyanogenus (LL-F28249 and deposited under NRRL No. 15773 and hereinafter referred to as *Streptomyces cyaneogriseus noncyanogenus*) which produces the agents $\alpha,\beta,\gamma\delta,\epsilon,\zeta,\eta,\iota,\theta,\lambda,\kappa$, and $\mu$ components was isolated from mallee sand found in southern Australia.

The structure and stereochemistry of LL-F28249, have not been fully defined, but the proposed structures are shown below. Component LL-F28249 was related to Hondamycin (Abimycin) which is disclosed in The Journal of Antibiotics, 22, No. 11, 52–526 (1969).

The strain is assigned to the genus Streptomyces based upon morphology and cell chemistry (content of the Lisomer of diaminopimelic acid). The strain's morphology and physiological data place it close to S. cyaneogriseus, as represented by ISP 5534 (ATCC 27426). Then, comparisons of the formation of gray aerial mycelium soluble pigments on media (Table A) and coiled chains of smooth conidia (3-25 spores per chain) were made. The present strain is negative for blue soluble pigment wherein the comparison strain, ISP 5534, is positive. The strains have similar reactions in the ISP carbohydrate utilization tests indicating positive for arabinose, fructose, glucose, rhamnose and xylose, while indicating negative for inositol, mannitol, raffinose and sucrose (ISP 5534) slightly positive). However, the strains differ in several characters (Table B) out of 53 in the Gordon tests. These differences support the creation of a subspecies of *S. cyaneogriseus* for the present microorganism.

TABLE A

Comparison of F 28249 and ISP 5534 on ISP Morphology Test Media (Numbers are from NBS-ISCC)

| Medium | | F 28249 | ISP 5534 |
|---|---|---|---|
| Yeast-Malt (ISP 2) | A.m.[1] | Medium gray (265) | Light to medium gray (264–265) |
| | V.m. | Light tannish (75) Deep yellow-brown | Light tannish-white to blackish-blue (188) |
| | S.p. | Light brown | Light brown |
| Inorganic salts starch (ISP 4) | A.m. | Light olive-gray (112) to medium gray (265) | Medium gray (265) |
| | V.m. | Deep gray to black (266–267) | Gray-purplish-blue (204) |
| | S.p. | Grayish-yellowish-brown | None |
| Glycerol-Asparagine (ISP 5) | A.m. | 264 (white) to yellowish-gray (93) | 263 (white) to light gray (264) |
| | V.m. | Black (267) to light olive brown (96) | Gray-purplish-blue (203–204) |
| | S.p. | Slight brownish | Light yellowish-gray |
| Oatmeal (ISP 3) | A.m. | Yellow-gray (93) | None |
| | V.m. | Colorless | Colorless |
| | S.p. | Slight yellowish | None |

[1] A.m., aerial mycelium;
V.m. = vegetative mycelium;
S.p. = Soluble pigment

TABLE B

Comparison of Lederle F 28249 with ISP 5534 (Gordon Tests)

| | F 28249 | ISP 5534 |
|---|---|---|
| Growth on/at | | |
| Salicin | ± | − |
| 10° | − | + |
| 45° | + | − |
| Production of | | |
| Urease | + | − |
| Decarboxylation of | | |
| Mucate | − | + |
| Acid Production | | |
| Raffinose | − | + |
| Sucrose | − | + |

Both strains have the following reactions:
Positive  Hydrolysis of casein; hypoxanthine, xanthine, tyrosine, adrenine, potato starch, gelatin, and esculin;
Production of phosphatase
Sensitivity to lysozyme
Decarboxylation of acetate, citrate, lactate, malate, oxalate and propionate
Acid production from arabinose, cellobiose, dextrin, fructose, galactose, glucose, glycerol, lactose, maltose, mannose, α-methyl D-glucoside, rhamnose, salicin, trehalose.
Negative  Production of nitrate reductase
Decarboxylation of benzoate and tartrate
Acid from adonitol, dulcitol, erythritol, inositol, mannitol, sorbitol, β-methyl-D-xyloside.
Growth on 5% NaCl

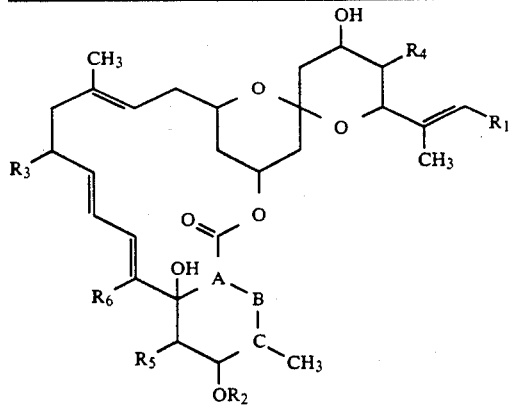

LL-F28249α-μ

| Component | $R_1$ | $R_2$ | $R_3$ | $R_4$ | $R_5$ | $R_6$ | $R_5 + R_6$ | A-B | B-C |
|---|---|---|---|---|---|---|---|---|---|
| LL-F28249α | $CH(CH_3)_2$ | H | $CH_3$ | $CH_3$ | | | $-O-CH_2-$ | $CH-CH$ | $CH=C$ |
| LL-F28249β | $CH_3$ | H | $CH_3$ | $CH_3$ | | | $-O-CH_2-$ | $CH-CH$ | $CH=C$ |
| LL-F28249γ | $CH_3$ | $CH_3$ | $CH_3$ | $CH_3$ | | | $-O-CH_2-$ | $CH-CH$ | $CH=C$ |
| LL-F28249δ | $CH_3$ | $CH_3$ | $CH_3$ | $CH_3$ | OH | $CH_2OH$ | | $CH-CH$ | $CH=C$ |
| LL-F28249ε | $CH(CH_3)_2$ | H | H | $CH_3$ | | | $-O-CH_2-$ | $CH-CH$ | $CH=C$ |
| LL-F28249ζ | $CH_2CH_3$ | H | $CH_3$ | $CH_3$ | | | $-O-CH_2-$ | $CH-CH$ | $CH=C$ |
| LL-F28249η | $CH(CH_3)_2$ | H | $CH_3$ | $CH_3$ | | | $-O-CH_2-$ | $C=CH$ | $CH-CH$ |
| LL-F28249θ | $CH(CH_3)_2$ | H | $CH_3$ | $CH_2CH_3$ | | | $-O-CH_2-$ | $CH-CH$ | $CH=C$ |
| LL-F28249ι | $CH(CH_3)_2$ | H | $CH_2CH_3$ | $CH_3$ | | | $-O-CH_2-$ | $CH-CH$ | $CH=C$ |
| LL-F28249κ | $CH_3$ | $CH_3$ | $CH_3$ | $CH_3$ | H | $CH_3$ | | $CH-CH$ | $CH=C$ |
| LL-F28249λ | $CH(CH_3)_2$ | $CH_3$ | $CH_3$ | $CH_3$ | | | $-O-CH_2-$ | $CH-CH$ | $CH=C$ |
| LL-F28249μ | $CH(CH_3)_2$ | $CH_3$ | $CH_3$ | $CH_3$ | H | $CH_3$ | | $CH-CH$ | $CH=C$ |

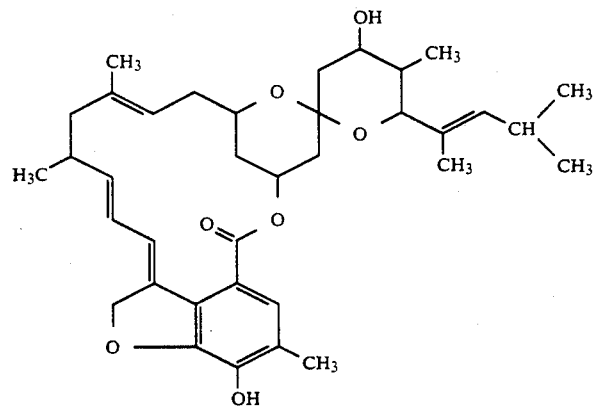

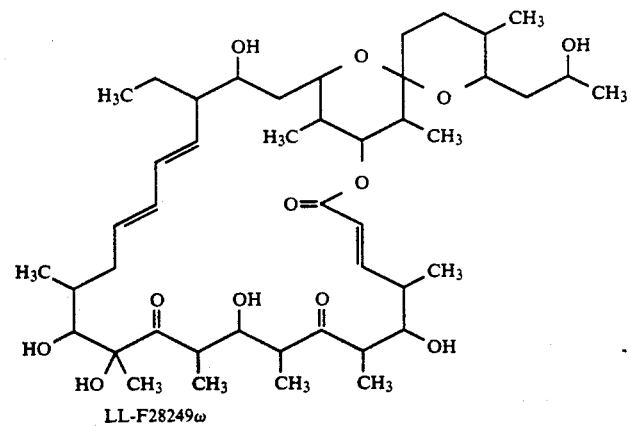

LL-F28249ω

It is an object of this invention to provide α,β,γ,δ,ε,ζ,η,θ,ι,κ,λ,μ, and ν compounds described and derived from *Streptomyces cyaneogriseus noncyanogenus*, NRRL 15773, and a method of their production by fermentation. It is a further object to provide methods for their recovery and concentration from crude solutions to purify said compounds. These substances have significant activity against helmintic, ectoparasitic and acaridal infections, and thus, are useful in so treating warmblooded animals afflicted with these infections, as well as treating plants inflicted with nematodes. The utility of the presently disclosed fermentation broth and, whole mash of the microorganism *Streptomyces cyaneogriseus noncyanogenus* NRRL 15773, and its components $\alpha,\beta,\delta,\epsilon,\zeta,\theta,\kappa,\iota,\lambda,\mu,\nu$ and $\omega$ is described in U.S. Pat. No. 4,869,901 and allowed and continuation-in-part U.S. Pat. application of Irwin Boyden Wood and John Anthony Pankovich, Ser. No. 732,251, filed May 10, 1985, now U.S. Pat. No 5,106,994, and incorporated herein by reference thereto.

These and further objects will become apparent by the description of the drawings and detailed description of the invention which follow.

DESCRIPTION OF THE DRAWINGS

FIG. 2: Characteristic infrared absorption spectrum of compound designated LL-F28249$\alpha$, NRRL 15773.

FIG. 3: Characteristic proton nuclear magnetic resonance spectrum of compound designated LL-F28249$\alpha$, NRRL 15773, in CDCl$_3$ solution.

FIG. 4: Characteristic carbon-13 nuclear magnetic resonance spectrum of compound designated LL-F28249$\alpha$, NRRL 15773, in CDCl$_3$ solution.

FIG. 5: Characteristic electron impact mass spectrum of compound designated LL-F28249$\alpha$, NRRL 15773.

FIG. 6: Characteristic ultraviolet absorption spectrum of compound designated LL-F28249$\beta$, NRRL 15773.

FIG. 7: Characteristic infrared absorption spectrum of compound designated LL-F28249$\beta$, NRRL 15773.

FIG. 8: Characteristic proton nuclear magnetic resonance spectrum of compound designated LL-F28249$\beta$, NRRL 5773, in CDCl$_3$.

FIG. 9: Characteristic electron impact mass spectrum of compound designated LL-F28249$\beta$, NRRL 15773.

FIG. 10: Characteristic ultraviolet absorption spectrum of compound designated LL-F28249$\gamma$, NRRL 15773.

FIG. 11: Characteristic infrared absorption spectrum of compound LL-F28249$\gamma$, NRRL 15773.

FIG. 12: Characteristic proton nuclear magnetic resonance spectrum of compound LL-F28249$\gamma$, NRRL 15773, in CDCl$_3$.

FIG. 13: Characteristic carbon-13 nuclear magnetic resonance spectrum of compound designated LL-F28249$\gamma$, NRRL 15773, in CDCl$_3$.

FIG. 14: Characteristic electron impact mass spectrum of compound designated LL-F28249$\gamma$, NRRL 15773.

FIG. 15: Characteristic ultraviolet absorption spectrum of compound designated LL-F28249$\omega$, NRRL 15773.

FIG. 16: Characteristic infrared absorption spectrum of compound designated LL-F28249$\omega$, NRRL 15773.

FIG. 17: Characteristic proton nuclear magnetic resonance spectrum of compound designated LL-F28249$\omega$, NRRL 15773, in CDCl$_3$.

FIG. 18: Characteristic nuclear magnetic resonance spectrum of compound designated LL-F28249$\omega$, NRRL 15773, in CDCl$_3$.

FIG. 19: Characteristic electron impact mass spectrum of compound designated LL-F28249$\omega$, NRRL 15773.

FIG. 20: Characteristic ultraviolet absorption spectrum of compound designated LL-F28249$\delta$, NRRL 15773.

FIG. 21: Characteristic proton nuclear magnetic resonance spectrum of compound designated LL-F28249$\delta$, NRRL 15773, in CDCl$_3$.

FIG. 22: Characteristic electron impact mass spectrum of compound designated LL-F28249$\delta$, NRRL 15773.

FIG. 23: Characteristic ultraviolet absorption spectrum of compound designated LL-F28249$\epsilon$, NRRL 15773.

FIG. 24: Characteristic proton nuclear magnetic resonance spectrum of compound designated LL-F28249$\epsilon$, NRRL 15773, in CDCl$_3$.

FIG. 25: Characteristic electron impact mass spectrum of compound designated LL-F28249$\epsilon$, NRRL 15773.

FIG. 26: Characteristic proton nuclear magnetic resonance spectrum of compound designated LL-F28249$\zeta$, NRRL 15773, in CDCl$_3$.

FIG. 27: Characteristic electron impact mass spectrum of compound designated LL-F28249$\zeta$, NRRL 15773.

FIG. 28: Characteristic ultraviolet absorption spectrum of compound designated LL-F28249$\eta$, NRRL 15773.

FIG. 29: Characteristic proton nuclear magnetic resonance spectrum of compound designated LL-F28249$\eta$, NRRL 15773, in CDCl$_3$.

FIG. 30: Characteristic electron impact mass spectrum of compound designated LL-F28249 $\eta$, NRRL 15773.

FIG. 31: Characteristic ultraviolet absorption spectrum of compound designated LL-F28249$\theta$, NRRL 5773.

FIG. 32: Characteristic proton nuclear magnetic resonance spectrum of compound designated LL-F28249$\theta$, NRRL 15773, in CDCl$_3$.

FIG. 33: Characteristic electron impact mass spectrum of compound designated LL-F28249$\theta$, NRRL 15773.

FIG. 34: Characteristic ultraviolet absorption spectrum of compound designated LL-F28249$\iota$, NRRL 15773.

FIG. 35: Characteristic proton nuclear magnetic resonance spectrum of compound designated LL-F28249$\iota$, NRRL 15773, in CDCl$_3$.

FIG. 36: Characteristic electron impact mass spectrum of compound designated LL-F28249$\iota$, NRRL 15773.

FIG. 37: Characteristic carbon—13 nuclear magnetic resonance spectrum of compound designated LL-F28249$\beta$, NRRL 15773, in CDCl$_3$ solution.

FIG. 38: Characteristic ultraviolet absorption spectrum of compound designated LL-F28249$\kappa$, NRRL 15773.

FIG. 39: Characteristic infrared absorption spectrum of compound designated LL-F28249$\kappa$, NRRL 15773.

FIG. 40: Characteristic electron impact mass spectrum of compound designated LL-F28249$\kappa$, NRRL 15773.

FIG. 41: Characteristic proton nuclear magnetic resonance spectrum of compound designated LLF28249$\kappa$NRRL 15773.

FIG. 42 Characteristic carbon—13 nuclear magnetic resonance spectrum of compound designated LL-F28249κ, NRRL 15773.

FIG. 43: Characteristic ultraviolet absorption spectrum of compound designated LL-F28249λ, NRRL 15773.

FIG. 44: Characteristic infrared absorption spectrum of compound designated LL-F28249λ, NRRL 15773.

FIG. 45: Characteristic electron impact mass spectrum of compound designated LL-F28249λ, NRRL 15773.

FIG. 46: Characteristic proton nuclear magnetic resonance spectrum of compound designated LLF28249λ, NRRL 15773.

FIG. 47: Characteristic carbon—13 nuclear magnetic resonance spectrum of compound designated LL-F28249λ, NRRL 15773.

FIG. 48: Characteristic ultraviolet absorption spectrum of compound designated LL-F28249μ, NRRL 15773.

FIG. 49: Characteristic infrared absorption spectrum of compound designated LL-F28249μ, NRRL 15773.

FIG. 50: Characteristic electron impact mass spectrum of compound designated LL-F28249μ, NRRL 15773.

FIG. 51: Characteristic proton nuclear magnetic resonance spectrum of compound designated LLF28249μ, NRRL 15773.

FIG. 52: Characteristic ultraviolet absorption spectrum of compound designated LL-F28249ν, NRRL 15773.

FIG. 53: Characteristic infrared absorption spectrum of compound designated LL-F28249ν, NRRL 15773.

FIG. 54: Characteristic electron impact mass spectrum of compound designated LL-F28249ν, NRRL 15773.

FIG. 55: Characteristic proton nuclear magnetic resonance spectrum of compound designated LLF28249ν, NRRL 15773.

FIG. 56: Characteristic carbon—13 nuclear magnetic resonance spectrum of compound designated LL-F28249ν, NRRL 15773.

DETAILED DESCRIPTION OF THE INVENTION

Figure 1:
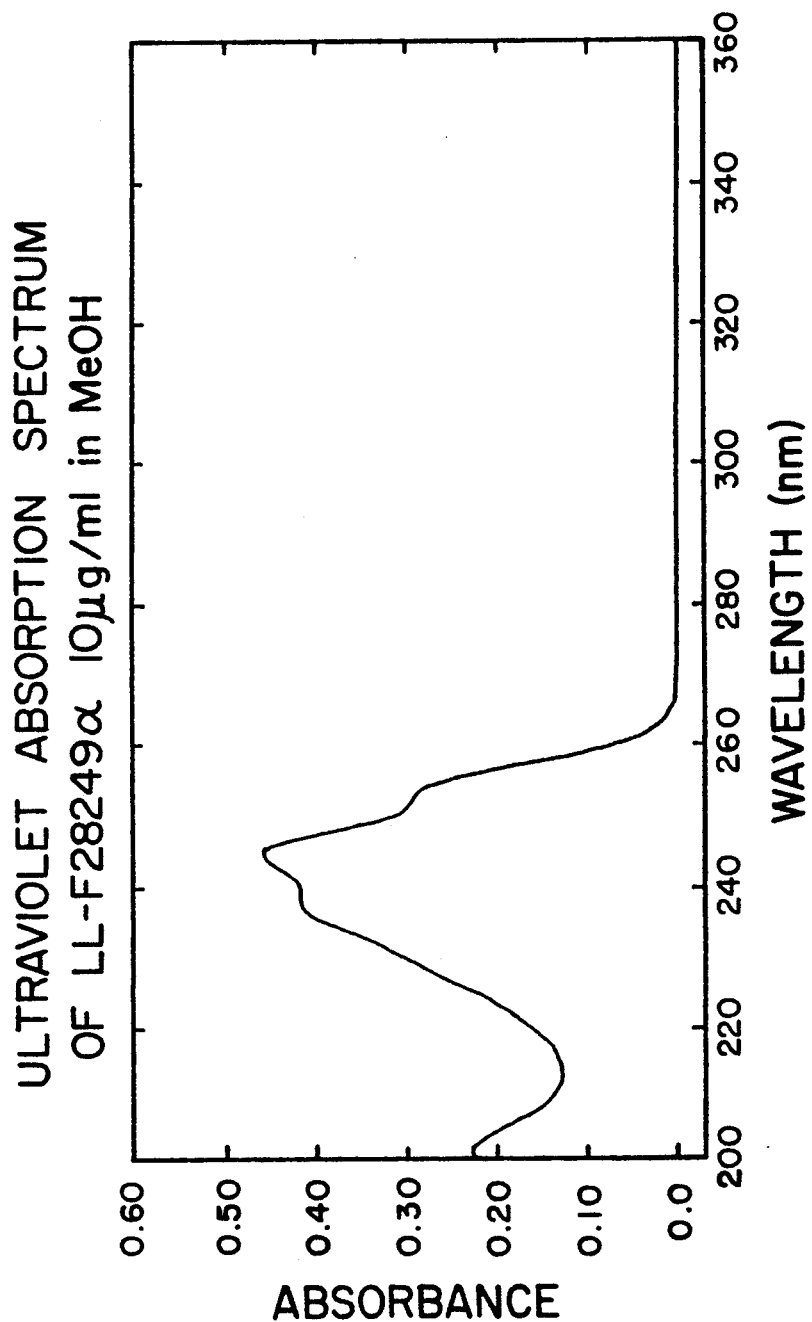
FIG. 1: Characteristic ultraviolet absorption spectrum of compound designated LL-F28249$\alpha$, NRRL 15773.

The physiochemical characteristics for the α, β, γ, δ, ε, ζ, η, θ, ι, κ, λ, μ, ν and ω components of LL-F28249 are described below:

LL-F28249α

1) Molecular weight: 612 (FAB-MS);
2) Molecular formula: $C_{36}H_{52}O_8$;
3) Specific optical rotation: $[\alpha]_D^{26} = +133 \pm 3°$(C 0.3, acetone);
4) Ultraviolet absorption spectrum: as shown in FIG. I $UV_{MAX}^{CH3OH} = 244$ nm ($\epsilon$28,000);
5) Infrared absorption spectrum: as shown in FIG. II (KBr disc): 3439, 2960, 2925, 1714, 1454, 1374, 1338, 1171, 1120, 996, 967 cm$^{-1}$;
6) Proton nuclear magnetic resonance spectrum (CDCl$_3$): as shown in FIG. III;
7) Carbon-13 nuclear magnetic resonance spectrum (CDCl$_3$): as shown in FIG. IV and described in Table I; and
8) Electron impact mass spectrum: as shown in FIG. V with accurate mass measurements and proposed elemental compositions indicated in Table II.

LL-F28249β

1) Molecular weight: 584 (FAB-MS);
2) Molecular formula: $C_{34}H_{48}O_8$;
3) Specific optical rotation: $[\alpha]_D^{26} = +125°$(C 0.30 acetone).
4) Ultraviolet absorption spectrum: as shown in FIG. VI $UV_{MAX}^{CH3OH} = 244$ nm ($\epsilon$25,600);
5) Infrared absorption spectrum: as shown in FIG. VII (KBr disc): 3520, 2910, 1735, 1717, 1450, 1375, 1335, 1180, 170, 1119, 993, 727 cm$^{-1}$;
6) Proton nuclear magnetic resonance spectrum (CDCl$_3$): as shown in FIG. VIII;
7) Carbon-13 nuclear magnetic resonance spectrum (CDCl$_3$): as shown in FIG. XXXVII and described in Table II A; and
8) Electron impact mass spectrum: as shown in FIG. IX with accurate mass measurements and proposed elemental compositions indicated in Table III.

LL-F28249γ

1) Molecular weight: 598 (FAB-MS);
2) Molecular formula: $C_{35}H_{50}O_8$;
3) Specific optical rotation: $[\alpha]_D^{26} = +150 \pm 4°$(C 0.3, acetone);
4) Ultraviolet absorption spectrum: as shown in FIG. X $UV_{MAX}^{CH3OH} = 244$ nm ($\epsilon$27,100);
5) Infrared spectrum as shown in FIG. XI (KBr disc): 3510, 2910, 1735, 1715, 1452, 1375, 1338, 1182, 1172, 1119, 995 cm$^{-1}$;
6) Proton nuclear magnetic resonance spectrum (CDCl$_3$): as shown in FIG. XII;
7) Carbon-13 nuclear magnetic resonance spectrum (CDCl$_3$): as shown in FIG. XIII and described in Table IV; and
8) Electron impact mass spectrum: as shown in FIG. XIV with accurate mass measurements and proposed elemental compositions indicated in Table V.

LL-F28249ω

1) Molecular weight: 806 (FAB-MS);
2) Molecular formula: $C_{45}H_{74}O_{12}$;
3) Specific optical rotation: $[\alpha]_D^{26} = -49 \pm 3°$(C 0.35, methanol);
Ultraviolet absorption spectrum: as shown in Figure XV $UV_{MAX}^{CH3OH}$ = 225 nm ($\epsilon$27,400)
232 nm ($\epsilon$25,700);

5) Infrared absorption spectrum: as shown in FIG. XVI (KBr disc): 3480, 2965, 2935, 2880, 1703, 1647, 1458, 1380, 1292, 1223, 1135, 1098, 984 cm$^{-1}$;
6) Proton nuclear magnetic resonance spectrum (CDCl$_3$): as shown in FIG. XVII;
7) Carbon-13 nuclear magnetic resonance spectrum (CDCl$_3$): as shown in FIG. XVIII and described in Table VI; and
8) Electron impact mass spectrum: as shown in FIG. XIX with accurate mass measurements and proposed elemental compositions indicated in Table VII.

LL-F28249δ

1) Molecular weight: 616 (EI-MS)
2) Molecular formula: $C_{35}H_{52}O_9$
3) HPLC retention volume of 14.0 ml in the system indicated in Table VIII;

4) Ultraviolet absorption spectrum (methanol): as shown in FIG. XX;

5) Proton nuclear magnetic resonance spectrum (CDCL$_3$): as shown in FIG. XXI; and 6) Electron impact mass spectrum: as shown in FIG. XXII.

LL-F28249ε

1) Molecular weight: 598 (EI-MS)

2) Molecular formula: $C_{35}H_{50}O_8$

3) HPLC retention volume of 14.8 ml in the system indicated in Table VIII;

4) Ultraviolet absorption spectrum (methanol): as shown in FIG. XXIII;

5) Proton nuclear magnetic resonance spectrum (CDCl$_3$): as shown in FIG. XXIV; and 6) Electron impact mass spectrum: as shown in FIG. XXV.

LL-F28249ζ

1) Molecular weight: 598 (EI-MS)

2) Molecular formula: $C_{35}H_{50}O_8$

3) HPLC retention volume of 16.0 ml in the system indicated in Table VIII;

4) Proton nuclear magnetic resonance spectrum (CDCL$_3$): as shown in FIG. XXVII; and 5) Electron impact mass spectrum: as shown in FIG. XXVIII.

LL-F28249η

1) Molecular weight: 612 (EI-MS)

2) Molecular formula: $C_{36}H_{52}O_8$

3) HPLC retention volume of 23.5 ml in the system indicated in Table VIII;

4) Ultraviolet absorption spectrum (methanol): as shown in FIG. XXVIII;)

5) Proton nuclear magnetic resonance spectrum (CDCl$_3$): as shown in FIG. XXIX; and 6) Electron impact mass spectrum: as shown in FIG. XXX.

LL-F28249θ

1) Molecular weight: 626 (El-MS)

2) Molecular formula: $C_{37}H_{54}O_8$

3) HPLC retention volume of 24.5 ml in the system indicated in Table VIII;

4) Ultraviolet absorption spectrum (methanol): as shown in FIG. XXXI;

5) Proton nuclear magnetic resonanace spectrum (CDCl$_3$): as shown in FIG. XXXII; and 6) Electron impact mass spectrum: as shown in FIG. XXXIII.

LL-F28249ι

1) Molecular weight: 626 (EI-MS)

2) Molecular formula: $C_{37}H_{54}O_8$

3) HPLC retention volume of 26.0 ml in the system indicated in Table VIII;

4) Ultraviolet absorption spectrum (methanol): as shown in FIG. XXXIV;

5) Proton nuclear magnetic resonance spectrum (CDCl$_3$): as shown in FIG. XXXV; and 6) Electron impact mass spectrum: as shown in FIG. XXXVII.

LL-F28249κ;

1) Molecular weight: 584 (EI-MS);

2) Molecular formula: $C_{35}H_{52}O_7$;

3) Specific optical rotation: $[\alpha]^{26}D = +189° - (C\ 0.165\ acetone)$;

4) Ultraviolet absorption spectrum: as shown in FIG. XXXVIII UV $_{MAX}{}^{CH3OH} = 241\,nm\ (E20,400)$;

5) Infrared absorption spectrum: as shown in FIG. XXXIX (KBr disc);

6) Electron impact mass spectrum: as shown in FIG. XL;

7) Proton nuclear magnetic resonance spectrum (CDCl$_3$); as shown in FIG. XLI; and 8) Carbon-13 nuclear magnetic resonance spectrum (CDC-l$_3$); as shown in FIG. XLII and described in Table IX.

LL-F28249λ

1) Molecular weight: 626 (FAB-MS);

2) Molecular formula: $C_{37}H_{54}O_8$;

3) Specific optical rotation $[\alpha]_D{}^{26} = +145°\ (C,\ 0.23\ acetone)$;

4) Ultraviolet absorption spectrum: as shown in FIG. XLIII UV $_{MAX}{}^{CH3OH} = 244\,nm\ (E30,000)$;

5) Infrared absorption spectrum: as shown in FIG. XLIV (KBr disc);

6) Electron impact mass spectrum: as shown in FIG. XLV;

7) Proton nuclear magnetic resonance spectrum (CDCl$_3$); as shown in FIG. XLVI; and 8) Carbon-13 nuclear magnetic resonance spectrum (CDC-l$_3$); as shown in FIG. XLVII and described in Table X.

LL-F28249μ

1) Molecular weight: 612 (El-MS);

2) Molecular formula: $C_{37}H_{56}O_7$;

3) Ultraviolet absorption spectrum: as shown in FIG. XLVIII UV $_{MAX}{}^{CH3OH} 241\,nm\ (E16,800)$;

4) Infrared absorption spectrum: as shown in FIG. XLIX (KBr disc);

5) Electron impact mass spectrum: as shown in FIG. L;

6) Proton nuclear magnetic resonance spectrum (CDCl$_3$); as shown in FIG. LI.

LL-F28249ν

1) Molecular weight: 592 (EI-MS);

2) Molecular formula: $C_{36}H_{48}O_7$;

3) Specific optical rotation: $[\alpha]_D{}^{26} + 136° - (C.325,\ acetone)$;

4) Ultraviolet absorption spectrum: as shown in FIG. LII UV $_{MAX}{}^{CH3OH} = 256\ (E20,500);\ 358(E\ 8,830)$;

5) Infrared absorption spectrum: as shown in FIG. LIII (KBr disc);

6) Electron impact mass spectrum: as shown in FIG. LIV;

7) Proton nuclear magnetic resonance spectrum (CDCl$_3$); as shown in FIG. LV; and 8) Carbon-13 nuclear magnetic resonance spectrum (CDCl$_3$); as shown in FIG. LVI, and described in Table XI.

TABLE I

Carbon-13 NMR Data for LL-F28249α

| Carbon | Chemical Shift[1] (ppm) | Proton Substitution |
|---|---|---|
| 1 | 173.4 | q[2] |
| 2 | 142.8 | CH |
| 3 | 139.4 | q |

TABLE I-continued

Carbon-13 NMR Data for LL-F28249α

| Carbon | Chemical Shift[1] (ppm) | Proton Substitution |
|---|---|---|
| 4 | 137.7 | q |
| 5 | 137.3 | q |
| 6 | 137.2 | CH |
| 7 | 130.6 | q |
| 8 | 123.3 | CH |
| 9 | 120.3[3] | CH |
| 10 | 118.0 | CH |
| 11 | 99.7 | q |
| 12 | 80.2 | q |
| 13 | 79.3 | CH |
| 14 | 76.7 | CH |
| 15 | 69.3 | CH |
| 16 | 68.5 | CH |
| 17 | 68.4 | $CH_2$ |
| 18 | 67.8 | CH |
| 19 | 67.7 | CH |
| 20 | 48.4 | $CH_2$ |
| 21 | 45.7 | CH |
| 22 | 41.1 | $CH_2$ |
| 23 | 40.7 | $CH_2$ |
| 24 | 36.1 | $CH_2$ |
| 25 | 36.0 | CH |
| 26 | 35.9 | CH |
| 27 | 34.7 | $CH_2$ |
| 28 | 26.8 | CH |
| 29 | 22.8[4] | $CH_3$ |
| 30 | 22.2 | $CH_3$ |
| 31 | 19.9 | $CH_3$ |
| 32 | 15.5 | $CH_3$ |
| 33 | 13.9 | $CH_3$ |
| 34 | 11.0 | $CH_3$ |

[1]Downfield from TMS; $CDCl_3$ solution.
[2]q = quarternary carbon.
[3,4]Two unresolved signals.

TABLE II

High Resolution Mass Measurements for LL-F28249α

| m/z | Elemental Composition |
|---|---|
| 612.3705 | $C_{36}H_{52}O_8$ |
| 594.3543 | $C_{36}H_{50}O_7$ |
| 576.3472 | $C_{36}H_{48}O_6$ |
| 484.3211 | $C_{30}H_{44}O_5$ |
| 482.2648 | $C_{29}H_{38}O_6$ |
| 466.3097 | $C_{30}H_{42}O_4$ |
| 448.2987 | $C_{30}H_{40}O_3$ |
| 442.2375 | $C_{26}H_{34}O_6$ |
| 425.2327 | $C_{26}H_{33}O_5$ |
| 354.2181 | $C_{23}H_{30}O_3$ |
| 314.1877 | $C_{20}H_{26}O_3$ |
| 278.1144 | $C_{15}H_{18}O_5$ |
| 265.1786 | $C_{16}H_{25}O_3$ |
| 248.1405 | $C_{15}H_{20}O_3$ |
| 247.1705 | $C_{16}H_{23}O_2$ |
| 237.1838 | $C_{15}H_{25}O_2$ |
| 219.1740 | $C_{15}H_{23}O$ |
| 151.0753 | $C_9H_{11}O_2$ |

TABLE IIa

Carbon-13 NMR Data for LL-F28249β

| Carbon | Chemical Shift (ppm)* |
|---|---|
| 1 | 173.3 |
| 2 | 142.6 |
| 3 | 139.5 |
| 4 | 137.7 |
| 5 | 137.3 |
| 6 | 133.9 |
| 7 | 123.8 |
| 8 | 123.4 |
| 9 | 120.3 |
| 10 | 120.2 |
| 11 | 118.0 |
| 12 | 99.7 |
| 13 | 80.2 |
| 14 | 79.4 |
| 15 | 76.7 |
| 16 | 69.2 |
| 17 | 68.6 |
| 18 | 68.3 |
| 19 | 67.8 |
| 20 | 67.7 |
| 21 | 48.4 |
| 22 | 45.7 |
| 23 | 41.0 |
| 24 | 40.8 |
| 25 | 36.1 |
| 26 | 35.9** |
| 27 | 34.7 |
| 28 | 22.3 |
| 29 | 19.8 |
| 30 | 15.5 |
| 31 | 13.8 |
| 32 | 13.1 |
| 33 | 10.8 |

*Downfield from TMS; $CDCl_3$ solution
**Two unresolved signals

TABLE III

High Resolution Mass Measurements for LL-F28249β

| m/z | Elemental Composition |
|---|---|
| 584.3388 | $C_{34}H_{48}O_8$ |
| 566.3306 | $C_{34}H_{46}O_7$ |
| 456.2864 | $C_{28}H_{40}O_5$ |
| 442.2391 | $C_{26}H_{34}O_6$ |
| 438.2780 | $C_{28}H_{38}O_4$ |
| 425.2331 | $C_{26}H_{33}O_5$ |
| 354.2187 | $C_{23}H_{30}O_3$ |
| 314.1858 | $C_{20}H_{26}O_3$ |
| 278.1168 | $C_{15}H_{18}O_5$ |
| 237.1491 | $C_{14}H_{21}O_3$ |
| 219.1380 | $C_{14}H_{19}O_2$ |
| 209.1534 | $C_{13}H_{21}O_2$ |
| 191.1418 | $C_{13}H_{19}O$ |
| 151.0750 | $C_9H_{11}O_2$ |

TABLE IV

Carbon-13 NMR Data for LL-F28249γ

| Carbon | Chemical Shift[1] (ppm) |
|---|---|
| 1 | 173.6 |
| 2 | 142.4 |
| 3 | 139.9 |
| 4 | 137.3 |
| 5 | 136.0 |
| 6 | 134.0 |
| 7 | 123.8 |
| 8 | 123.6 |
| 9 | 120.4 |
| 10 | 119.6 |
| 11 | 118.5 |
| 12 | 99.8 |
| 13 | 80.5 |
| 14 | 77.8 |
| 15 | 77.0 |
| 16 | 76.8 |
| 17 | 69.3 |
| 18 | 68.6 |
| 19 | 68.3 |
| 20 | 67.9 |
| 21 | 57.7 |
| 22 | 48.5 |
| 23 | 45.8 |
| 24 | 41.2 |
| 25 | 40.8 |
| 26 | 36.2 |
| 27 | 36.1 |

TABLE IV-continued

Carbon-13 NMR Data for LL-F28249γ

| Carbon | Chemical Shift[1] (ppm) |
|---|---|
| 28 | 36.0 |
| 29 | 34.8 |
| 30 | 22.3 |
| 31 | 19.9 |
| 32 | 15.5 |
| 33 | 13.8 |
| 34 | 13.1 |
| 35 | 10.8 |

[1]Downfield from TMS; CDCl$_3$ solution.

TABLE V

High Resolution Mass Measurements for LL-F28249γ

| m/z | Elemental Composition |
|---|---|
| 598.3543 | $C_{35}H_{50}O_8$ |
| 580.3422 | $C_{35}H_{48}O_7$ |
| 562.3292 | $C_{35}H_{46}O_6$ |
| 496.2824 | $C_{30}H_{40}O_6$ |
| 484.2440 | $C_{28}H_{36}O_7$ |
| 478.2687 | $C_{30}H_{38}O_5$ |
| 456.2576 | $C_{27}H_{36}O_6$ |
| 438.2772 | $C_{28}H_{38}O_4$ |
| 425.2341 | $C_{26}H_{33}O_5$ |
| 420.2651 | $C_{28}H_{36}O_3$ |
| 354.2199 | $C_{23}H_{30}O_3$ |
| 314.1875 | $C_{20}H_{26}O_3$ |
| 292.1307 | $C_{16}H_{20}O_5$ |
| 288.2075 | $C_{19}H_{28}O_2$ |
| 248.1397 | $C_{15}H_{20}O_3$ |
| 237.1490 | $C_{14}H_{21}O_3$ |
| 219.1382 | $C_{14}H_{19}O_2$ |
| 209.1544 | $C_{13}H_{21}O_2$ |
| 191.1435 | $C_{13}H_{19}O$ |
| 151.0759 | $C_9H_{11}O_2$ |

TABLE VI

Carbon-13 NMR Data for LL-F28249ω

| Carbon | Chemical Shift[1] (ppm) |
|---|---|
| 1 | 220.7 |
| 2 | 219.6 |
| 3 | 165.2 |
| 4 | 148.7 |
| 5 | 133.1 |
| 6 | 132.3 |
| 7 | 132.1 |
| 8 | 130.2 |
| 9 | 122.3 |
| 10 | 100.0 |
| 11 | 82.9 |
| 12 | 75.9 |
| 13 | 73.0 |
| 14 | 72.7 |
| 15 | 72.6 |
| 16 | 72.1 |
| 17 | 69.0 |
| 18 | 67.3 |
| 19 | 63.6 |
| 20 | 51.4 |
| 21 | 46.2 |
| 22 | 45.7 |
| 23 | 42.2[2] |
| 24 | 40.4 |
| 25 | 38.3 |
| 26 | 37.6 |
| 27 | 36.1 |
| 28 | 34.8 |
| 29 | 33.5 |
| 30 | 30.1 |
| 31 | 26.6 |
| 32 | 25.4 |
| 33 | 24.5 |
| 34 | 23.0 |
| 35 | 21.1 |
| 36 | 17.9 |
| 37 | 14.3 |
| 38 | 14.2 |
| 39 | 12.1 |
| 40 | 11.5 |
| 41 | 10.9 |
| 42 | 8.7 |
| 43 | 8.3 |
| 44 | 5.7 |

[1]Downfield from TMS; CDCl$_3$ solution.
[2]Two unresolved signals.

TABLE VII

High Resolution Mass Measurements for LL-F28249ω

| m/z | Elemental Composition |
|---|---|
| 462.3350 | $C_{28}H_{46}O_5$ |
| 444.3237 | $C_{28}H_{44}O_4$ |
| 425.2534 | $C_{23}H_{37}O_7$ |
| 407.2439 | $C_{23}H_{35}O_6$ |
| 406.3046 | $C_{25}H_{42}O_4$ |
| 387.2895 | $C_{25}H_{39}O_3$ |
| 337.2010 | $C_{19}H_{29}O_5$ |
| 297.2031 | $C_{17}H_{29}O_4$ |
| 279.1944 | $C_{17}H_{27}O_3$ |
| 261.1851 | $C_{17}H_{25}O_2$ |
| 253.1797 | $C_{15}H_{25}O_3$ |
| 235.1697 | $C_{15}H_{23}O_2$ |
| 224.1754 | $C_{14}H_{24}O_2$ |
| 209.1530 | $C_{13}H_{21}O_2$ |
| 207.1744 | $C_{14}H_{23}O$ |
| 184.1458 | $C_{11}H_{20}O_2$ |
| 179.1048 | $C_{11}H_{15}O_2$ |
| 173.1205 | $C_9H_{17}O_3$ |
| 167.1051 | $C_{10}H_{15}O_2$ |
| 155.1069 | $C_9H_{15}O_2$ |

TABLE VIII

HPLC Retention Volumes for LL-F28249α, δ, ε, ζ, η, θ and ι

| Compound | Retention Volume* (ml) |
|---|---|
| LL-F28249 α | 19.8 |
| LL-F28249 δ | 14.0 |
| LL-F28249 ε | 14.8 |
| LL-F28249 ζ | 16.0 |
| LL-F28249 η | 23.5 |
| LL-F28249 θ | 24.5 |
| LL-F28249 ι | 26.0 |

*System includes a column 3.9 mm × 30 cm packed with $C_{18}$ reverse phase packing developed with methanol:water (80:20) at 1.0 ml/minute, detection was by absorbance at 254 nm.

TABLE IX

Carbon-13 NMR Data for LL-F28249κ

| Carbon | Chemical Shift (ppm)* |
|---|---|
| 1 | 173.9 |
| 2 | 140.7 |
| 3 | 138.3 |
| 4 | 136.6 |
| 5 | 136.5 |
| 6 | 133.8 |
| 7 | 124.7 |
| 8 | 124.4 |
| 9 | 123.8 |
| 10 | 120.1 |
| 11 | 118.5 |
| 12 | 99.7 |
| 13 | 77.2 |
| 14 | 76.6** |
| 15 | 76.5 |

TABLE IX-continued

Carbon-13 NMR Data for LL-F28249κ

| Carbon | Chemical Shift (ppm)* |
|---|---|
| 16 | 69.3 |
| 17 | 68.6 |
| 18 | 67.3 |
| 19 | 56.7 |
| 20 | 48.4 |
| 21 | 47.7 |
| 22 | 41.1 |
| 23 | 40.6 |
| 24 | 37.1 |
| 25 | 36.3 |
| 26 | 36.0 |
| 27 | 35.9 |
| 28 | 34.6 |
| 29 | 22.0 |
| 30 | 19.3 |
| 31 | 16.0 |
| 32 | 13.8 |
| 33 | 13.3 |
| 34 | 13.1 |
| 35 | 10.7 |

*Downfield from TMS; CDCl₃ solution
**Coincident with CDCl₃ signals.

TABLE X

Carbon-13 NMR Data for LL-F28249λ

| Carbon | Chemical Shift (ppm)* |
|---|---|
| 1 | 173.6 |
| 2 | 142.5 |
| 3 | 139.8 |
| 4 | 137.4 |
| 5 | 137.2 |
| 6 | 136.0 |
| 7 | 130.7 |
| 8 | 123.6 |
| 9 | 120.3 |
| 10 | 119.7 |
| 11 | 118.6 |
| 12 | 99.8 |
| 13 | 80.5 |
| 14 | 77.7 |
| 15 | 77.6 |
| 16 | 76.7 |
| 17 | 69.3 |
| 18 | 68.6 |
| 19 | 68.3 |
| 20 | 67.9 |
| 21 | 57.8 |
| 22 | 48.6 |
| 23 | 45.8 |
| 24 | 41.2 |
| 25 | 40.9 |
| 26 | 36.1** |
| 27 | 36.0 |
| 28 | 34.9 |
| 29 | 26.9 |
| 30 | 23.0** |
| 31 | 22.4 |
| 32 | 20.0 |
| 33 | 15.7 |
| 34 | 14.0 |
| 35 | 11.1 |

*Downfield from TMS; CDC₃ solution.
**Two unresolved signals.

TABLE XI

Carbon-13 NMR Data for LL-F28249ν

| Carbon | Chemical Shift (ppm)* |
|---|---|
| 1 | 167.4 |
| 2 | 150.5 |
| 3 | 142.9 |
| 4 | 142.0 |
| 5 | 137.2** |
| 6 | 132.1 |
| 7 | 130.7 |
| 8 | 125.8 |
| 9 | 125.5 |
| 10 | 124.2 |
| 11 | 123.7 |
| 12 | 123.2 |
| 13 | 121.3 |
| 14 | 118.0 |
| 15 | 100.0 |
| 16 | 76.7 |
| 17 | 74.6 |
| 18 | 69.4 |
| 19 | 68.7 |
| 20 | 68.3 |
| 21 | 48.4 |
| 22 | 41.0** |
| 23 | 35.9 |
| 24 | 35.6 |
| 25 | 35.5 |
| 26 | 34.4 |
| 27 | 29.7 |
| 28 | 26.8 |
| 29 | 22.9 |
| 30 | 22.8 |
| 31 | 22.1 |
| 32 | 15.3 |
| 33 | 13.9 |
| 34 | 11.0 |

*Downfield from TMS; CDCl₃ solution.
**Two unresolved signals.

TABLE XII

| | Chromatographic Data | |
|---|---|---|
| Component | TLC* Relative Rf | HPLC** Retention Time (minutes) |
| α | 1.00 | 13.8 |
| β | .797 | 9.3 |
| γ | 1.42 | 12.6 |
| δ | .758 | 10.4 |
| ε | 1.06 | 10.9 |
| ζ | 1.12 | 11.5 |
| η | 1.03 | 16.2 |
| θ | 1.27 | 17.3 |
| ι | 1.27 | 18.2 |
| κ | 1.83 | 24.7 |
| λ | 1.56 | 19.1 |
| μ | 1.92 | 38.0 |
| ν | 1.95 | 42.3 |
| ω | .212 | 7.1 |

*Analtech Silica Gel GHLF250μ developed with ethyl acetate:methylene chloride (1:3), detection by charring with H₂SO₄.
**Altex Ultrasphere ODS 5μ 4.6 mm × 25 cm developed with 85% methanol in water at 1.0 ml/minute, detection by absorbance at 254 nm.

The new agents designated LL-F28249α,β, γ,δ,ε, ζ,η, θ,ι,κ,λ,μ,ν and ω are formed during the cultivation under controlled conditions of *Streptomyces cyaneogriseus noncyanogenus*. NRRL 15773.

This organism is maintained in the culture collection of the Medical Research Division, American Cyanamid Company, Pearl River, N.Y. as culture number LL-F28249. A viable culture of this new microorganism has been deposited with the Patent Culture Collection Laboratory, Northern Regional Research Center, U.S. Department of Agriculture, Peoria, Ill. 61604, and has been added to its permanent collection. It is freely available to the public in this depository under its accession number NRRL 15773.

For the production of these new agents the present invention is not limited to this particular organism. In fact, it is desired and intended to include the use of naturally-occurring mutants of this organism, as well as induced mutants produced from this organism by various mutagenic means known to those skilled in the art, such as exposure to nitrogen mustard, X-ray radiation, ultraviolet radiation, N'-methyl-N'nitro-N-nitrosoguanidine, actinophages and the like. It is also desired and intended to include inter- and intraspecific genetic recombinants produced by genetic techniques known to those skilled in the art such as for example, conjugation, transduction and genetic engineering techniques.

Cultivation of *Streptomyces cyaneogriseus non-cyanogenus*, NRRL 15773 may be carried out in a wide variety of liquid culture media. Media which are useful for the production of agents LL-F28249α,β,γ,δ,ε,ζ,η,θ, ζ,κ,λ,μ,ν and ω include an assimilable source of carbon, such as dextrin, sucrose, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone oil may be added as needed.

EXAMPLE 1

Inoculum Preparation

A typical medium used to grow the various stages of inoculum was prepared according to the following formula:

| | |
|---|---|
| Dextrose | 1.0% |
| Dextrin | 2.0% |
| Yeast extract | 0.5% |
| NZ amine | 0.5% |
| Calcium carbonate | 0.1% |
| Water qs | 100% |

This medium was sterilized. A 00 ml portion of this sterile medium, in a flask, was inoculated with mycelial scrapings from an agar slant of *Streptomyces cyaneogriseus noncyanogenus* NRRL 15773. The medium was then agitated vigorously on a rotary shaker for 48–72 hours at 28° C. providing primary inoculum. This primary inoculum was then used to inoculate one liter of the above sterile medium, which was then grown aerobically at 28° C. for 48 hours providing secondary inoculum.

EXAMPLE 2

Fermentation

A fermentation medium of the following formulation was prepared.

| | |
|---|---|
| Dextrin | 1.0% |
| Soya peptone | 1.0% |
| Molasses | 2.0% |
| Calcium carbonate | 0.1% |
| Water qs | 100% |

This medium was sterilized and then a 30 liter portion was inoculated with one liter of secondary inoculum prepared as described in Example 1. The fermentation was conducted at 30° C., with a sterile air flow of 30 liters per minute, backpressure of 8 psig and agitation by an impeller operated at 500 rpm for 91 hours at which time the mash was harvested.

EXAMPLE 3

Isolation of LL-F28249α, β and γ

A total of 26 liters of whole harvest mash, prepared as described in Example 2 was mixed with 1500 g of diatomaceous earth and filtered. The mycelial cake was washed with 5 liters of water and the filtrate and wash discarded. The mycelial cake was mixed with 10 liters of methanol for one hour, then filtered and washed with 5 liters of methanol. The methanol extract and methanol wash were combined and evaporated to an aqueous residue of about 1–2 liters. This aqueous residue was mixed with twice its volume of methylene chloride and mixed for ½ hour. The methylene chloride phase was separated and then concentrated to a syrup giving 27 g of crude material.

This 27 g of crude material was dissolved in a mixture of methylene chloride and methanol, filtered through cotton and anhydrous sodium sulfate and then evaporated, giving 7.0 g of an oil.

A 170 g portion of silica gel was slurried in 12.5% ethyl acetate in methylene chloride and poured to form a column 2.5×58 cm. The oil was dissolved in 12.5% ethyl acetate in methylene chloride and applied to the column. The column was developed with the same solvent mixture. The mobile phase was run at 1.3 ml/minute initially and 15 minute fractions were collected. The flow rate slowed to about 0.5 ml/minute after 10 fractions, so fractions 1–10 were 20 ml decreasing to about 10 ml uniformly and fractions 11–98 were about 7 ml. At fraction 99 the flow rate was increased to give 25 ml fractions in 10 minutes. A total of 105 fractions were collected. These fractions were tested by thin layer chromatography in ethyl acetate:methylene chloride (1:1).

Fractions 30–54 were combined and evaporated giving 1.08 g of an oil containing LL-F28249γ.

Fractions 55–62 were combined and evaporated giving 150 mg of solid containing LL-F28249α and β.

The 150 mg of solid containing LL-F28249 α and β was chromatographed by preparative HPLC using a reverse-phase column (Whatman C8, 2.2×50 cm) developed with 80% (v/v) methanol in water. The flow rate was about 10 ml/-minute and 2 minute fractions were collected.

Fractions 58–69 were combined, the methanol was evaporated, r-butanol was added and the mixture was lyophilized, giving 60 mg of pure LL-F28249α.

Fractions 40–43 were combined, the methanol was evaporated and the residual aqueous suspension was extracted with methylene chloride which, upon evaporation, gave 10 mg of pure LL-F28249β.

The 1.08 g of oil containing LL-F28249γ was dissolved in 10% ethyl acetate in methylene chloride and applied to a column (2.5×50 cm) packed with silica gel. The column was developed with 10g ethyl acetate in methylene chloride, eluting at a flow rate of 2 ml/minute and collecting 12 minute fractions. Fractions 19–29 were combined and evaporated to a residue. This residue was purified by preparative reverse-phase chromatography as described for the α and β components. Fractions 55–62 were combined, the methanol was evaporated in vacuo, t-butanol was added and the mixture was lyophilized giving 60 mg of pure LL-F28249γ.

EXAMPLE 4

LARGE SCALE FERMENTATION

An inoculum of *Streptomyces cyaneogriseus noncyanogenus*, NRRL 15773 was prepared as described in Example 1, using 100 ml of primary inoculum to produce 10 liters of secondary inoculum.

Two 300 liter fermentations were conducted as described in Example 2 using 10 liters of the above secondary inoculum for each 300 liters of fermentation medium. At the end of 118 hours the mashes were harvested.

EXAMPLE 5

Isolation of LL-F28249ω

A total of 450 liters of harvest mash from the two 300 liter fermentations described in Example 4 was treated as described in the first portion of Example 3 giving crude material as a syrup.

This syrupy residue was washed with hexane to remove non-polar materials and the remaining 9 g of insoluble material was subjected to Sephadex LH-20 partition chromatography.

The chromatographic column was prepared with 9 liters of Sephadex LH-20, previously swelled in methanol, to form a column 10×110 cm. The column was equilibrated by passing about 4800 ml of mobile phase [methylene chloride:hexane:methanol (10:10:1)] through it at a flow rate of 5 ml/minute. The 9 g of insoluble material was charged onto the column in 50 ml of the mobile phase. An initial forerun of 2150 ml was obtained at a flow rate of 5 ml/minute. The flow rate was then increased to 8 ml/minute and fractions were collected every 45 minutes. Fractions 9–12 were combined and the solvents evaporated in vacuo giving 4.9 g of residue.

This residue was dissolved in a 1:1 mixture of cyclohexane and ethyl acetate and allowed to evaporate slowly at room temperature. The addition of n-hexane gave a precipitate which was collected, giving 3.1 g of solid.

A 3.0 g portion of this solid was further purified by precipitation from 25 m of methylene chloride using 50 ml of n-hexane.

The precipitate thus obtained was redissolved in 15 ml of methylene chloride and precipitated with 25 ml of n-hexane, giving 510 mg of pure LL-F28249ω.

EXAMPLE 6

Isolation of LL-F28249δ,ε,ζ,η,θ and ι

Fractions 4–7 from the Sephadex LH-20 column described in Example 5 were combined and the solvents evaporated in vacuo to give 1.9 g of residue.

This residue was chromatographed on a 200 g silica gel column (2.5 cm×83 cm) using 10% ethyl acetate in methylene chloride as the eluant. The flow rate was approximately 2 ml/minute and fractions were collected every 12 minutes.

Fractions 65–67 and 73–79 were combined together and the solvents were evaporated in vacuo to yield 250 mg of residue.

This 250 mg of residue was subjected to preparative reverse-phase chromatography as described in Example 3 except using 75% methanol in water as the mobile phase. The flow rate was about 10 ml/minute. The first 2000 ml portion of eluate was diverted to waste then 72 fractions were collected at 2.0 minute intervals. After diverting another portion of eluate to waste (between 300–400) fractions were collected again but at 2.5 minute intervals.

Fractions were combined as indicated below. The combined fractions were allowed to evaporate in a fume hood overnight, then the components were extracted into methylene chloride. Following evaporation of the solvent about 1 mg each of the pure components were obtained.

| Fractions Combined | Compound |
| --- | --- |
| 7–10 | LL-F28249 δ |
| 19–22 | LL-F28249 ε |
| 28–31 | LL-F28249 ζ |
| 81–83 | LL-F28249 η |
| 86–88 | LL-F28249 θ |
| 93–95 | LL-F28249 ι |

EXAMPLE 7

Isolation of LL-F28249κ,λ,μ and ν

A total of 390 liters of fermentation mash, harvested from fermentations conducted as described in Example 2, was processed essentially as described in the first paragraph of Example 3, giving 120 ml of methylene chloride concentrate. This concentrate was diluted with 200 ml of hexane and chilled overnight at 4° C. The resulting precipitate was removed by filtration and discarded. The filtrate was diluted with 300 ml of hexane. The resulting precipitate (A) was collected by filtration and saved. This filtrate was evaporated to dryness and the oily residue was then dissolved in 200 ml of methylene chloride and diluted with 1700 ml of hexane. The resulting precipitate (B) was collected by filtration and saved. This filtrate was concentrated to an oily residue which was then redissolved in 50 ml of methylene chloride, 950 ml of methanol was added and this solution was stored at 4° C. for 3 days. The resulting precipitate was removed by filtration and discarded. The filtrate was evaporated to dryness and the residue (C) combined with (A) and (B) and subjected to chromatography as follows: The 5.0×109 cm column was slurry-packed with Woelm TSC silica gel in ethyl acetate:-methylene chloride (1:9). The column was developed with the same solvent mixture at a rate of 25 ml/minute. The first 2 liters of effluent were discarded, then sixteen 400 ml fractions were collected.

Fractions 2 and 3 were combined and evaporated giving 3.9 g of oily material (D).

Fractions 4 through 7 were combined and evaporated giving 9.5 g of oily material which was dissolved in hexane and chromatographed on a 2.5×110cm column slurry-packed with 300 g of Woelm silica gel in ethyl acetate, hexane (1:4). The column was developed with the same solvent system at a rate of 4 ml/minute, collecting fractions at 7 minute intervals.

Fractions 45–54 were combined and evaporated, giving 0.3 g of material (E).

Fractions 63–135 were combined, evaporated to dryness, then redissolved in t-butanol and lyophilized giving 4.6 g of off-white solid (F).

LL-F28249κ and μ

Material (D) and (E) were combined and chromatographed on a 2.5×110 cm column packed with 300 g of Woelm silica gel, developing with ethyl acetate hexane (1:9). The flow rate was maintained at 4 ml/minute and fractions were collected at 7 minute intervals.

Fractions 67-115 were combined and evaporated to dryness, giving 920 mg of residue (G).

This residue (G) was chromatographed by preparative HPLC using a reverse phase column (Whatman C8, 2.2×50 cm) and developing with 85% (v/v) methanol in water The flow rate was about 10 ml/minute and fractions were collected at 2.5 minute intervals.

Fractions 33-40 were combined, concentrated to remove the methanol, then extracted with methylene chloride. The residue obtained upon evaporation was dissolved in t-butanol and then lyophilized, giving 60 mg of LLF-28249κ.

Fractions 52-58 were similarly processed giving a small quantity of LL-F28249μ.

LL-F28249λ

A one gram portion of material (F) was chromatographed by reverse phase HPLC, as described above, except that 80% (v/v) methanol in water was used as euent.

Fractions 61-75were combined and processed as giving 100 mg of LL-F28249λ.

LL-F28249ν

A 396 g portion of material essentially the same as material (D) above, was dissolved in 500 ml of methanol and then chiled at 40° for several hours The resulting precipitate was removed by filtration, washed with cod methanol and discarded. The combined filtrate and wash was evaporated. The residual oil was dissolved in hexane and charged on a 5×50 cm dry-packed silica gel column (Mallinkrodt SilicAR cc-7). The column was eluted with ethyl acetate:hexane (1.5:8.5) at a rate of about 50 ml/-minute.

| Four fractions were collected. | |
| --- | --- |
| Fraction | Volume (liters) |
| 1 | 1 |
| 2 | 4 |
| 3 | 1 |
| 4 | 2 |

Fraction 3 was evaporated, giving 5.0 g of residue which was purified by preparative reverse phase HPLC (Waters $C_{18}$, 5×60 cm). The column was initially developed with 16 liters of 80% methanol in water (v/v) at 100 ml/minute, then with 6.4 liters of 84% methanol in water (v/v). The first liter of effluent was discarded and then fractions of 400 ml were collected.

Fractions 44-47 were combined and processed as described above, giving 390 mg of LLF28249ν as a pale yellow solid.

What is claimed is:

1. The compound designated LL-F28294ω or a pharmaceutically acceptable salt through the compound has:
    a) a molecular weight of 806 (FAB-MS);
    b) a molecular formula, $C_{45}H_{74}O_{12}$;
    c) a specific optical rotation: $[\alpha]_D^{26} = -49 \pm 4°$ (C 0.35, methanol);
    d) a characteristic ultraviolet adsorption spectrum as shown in FIG. XV of the attached drawings;
    e) a characteristic infrared adsorption spectrum as shown in FIG. XVI of the attached drawings;
    f) a characteristic proton nuclear magnetic resonance spectrum as shown in FIG. XVII of the attached drawings;
    g) a characteristic carbon-13 nuclear resonance spectrum as shown in FIG. XVIII of the attached drawings with significant peaks at, 220.7; 219.6; 165.2; 148.7; 133.1; 132.3; 130.2; 122.3; 100.0; 82.9; 75.9; 73.0; 72.7; 72.6; 72.1; 69.0; 67.3; 63.6; 51.4; 46.2; 45.7; 42.2; 40.4; 38.3; 37.6; 36.1; 34.8; 33.5; 30.1; 26.6; 25.4; 24.5; 23.0; 21.1; 17.9; 14.3; 14.2; 12.1; 11.5; 10.9; 8.7; 8.3; 5.7; and
    h) a characteristic electron impact mass spectrum as shown in FIG. XIX of the attached drawings with measured m/z values and proposed elemental compositions as indicated below obtained by high resolution mass measurements,

| | | | |
| --- | --- | --- | --- |
| 462.3350 | $C_{28}H_{46}O_5$ | 253.1797 | $C_{15}H_{25}O_3$ |
| 444.3237 | $C_{28}H_{44}O_4$ | 235.1697 | $C_{15}H_{23}O_2$ |
| 425.2534 | $C_{23}H_{37}O_7$ | 224.1754 | $C_{14}H_{24}O_2$ |
| 407.2439 | $C_{23}H_{35}O_6$ | 209.1530 | $C_{13}H_{21}O_2$ |
| 406.3046 | $C_{25}H_{42}O_4$ | 207.1744 | $C_{14}H_{23}O$ |
| 387.2895 | $C_{25}H_{39}O_3$ | 184.1458 | $C_{11}H_{20}O_2$ |
| 337.2010 | $C_{19}H_{29}O_5$ | 179.1048 | $C_{11}H_{15}O_2$ |
| 297.2031 | $C_{17}H_{29}O_4$ | 173.1205 | $C_9H_{17}O_3$ |
| 279.1944 | $C_{17}H_{27}O_3$ | 167.1051 | $C_{10}H_{15}O_2$ |
| 261.1851 | $C_{17}H_{25}O_2$ | 155.1069 | $C_9H_{15}O_2$. |

2. The compound designated LL-F28249η or a pharmaceutically acceptable salt thereof the compound has:
    a) a molecular weight of 612 (EI-MS);
    b) a molecular formula, $C_{36}H_{52}O_8$;
    c) a HPLC retention value of 23.5 ml;
    d) a characteristic ultraviolet absorption spectrum as shown in FIG. XXVIII of the attached drawings;
    e) a characteristic proton nuclear magnetic resonance spectrum as shown in FIG. XXIX of the attached drawings; and
    f) a characteristic electron impact mass spectrum as shown in FIG. XXX of the attached drawings.

3. The compound designated LL-F28249κ or a pharmaceutically acceptable salt thereof the compound has:
    a) molecular weight 584 (EI-MS);
    b) molecular formula: $C_{35}H_{52}O_7$;
    c) Specific optical rotation: $[\alpha]_D^{26} = +189° - (C\ 0.165\ acetone)$;
    d) Ultraviolet absorption spectrum: as shown in FIG. XXXVIII UV $_{MAX}{}^{CH3OH}$241 nm (E20,400);
    e) Infrared absorption spectrum: as shown in FIG. XXXIX (KBr disc);
    f) Electron impact mass spectrum: as shown in FIG. XL;
    g) Proton nuclear magnetic resonance spectrum ($CDCl_3$); as shown in FIG. XLI; and
    h) Carbon-13 nuclear magnetic resonance spectrum ($CDCl_3$); as shown in FIG. XLII and described in Table IX.

4. The compound designated LL-F28249μ or a pharmaceutically acceptable salt thereof the compound has:
    a) molecular weight: 612 (EI-MS);
    molecular formula: $C_{37}H_{56}O_7$;
    c) Ultraviolet absorption spectrum: as shown in FIG. XLVIII UV $_{MAX}{}^{CH3OH}=241$ nm (E16,800);
    d) Infrared absorption spectrum: as shown in FIG. XLIX (Kbr disc);
    e) Electron impact mass spectrum: as shown in FIG. L,
    f) Proton nuclear magnetic resonance spectrum ($CDCl_3$); as shown in FIG. LI.

5. The compound designated LL-F28249ν or a pharmaceutically acceptable salt thereof wherein the compound has:

a) molecular weight: 592 (EI-MS);
b) molecular formula: $C_{36}H_{48}O_7$;
c) specific optical rotation: $[\alpha]_D^{26} +131°$ (C 0.325, acetone):
d) Ultraviolet absorption spectrum, as shown in FIG. LII UV $_{MAX}^{CH3OH}$ = 256 (E20,500); 358 (E8,830);
e) Infrared absorption spectrum: as shown in FIG. LIII (KBr disc);
f) Electron impact mass spectrum: as shown in FIG. LIV;
g) Proton nuclear magnetic resonance spectrum (CDCl$_3$); as shown in FIG. LV; and
h) Carbon-13 nuclear magnetic resonance spectrum (C-DCl$_3$); as shown in FIG. LVI, and described in Table XI.

* * * * *